(12) United States Patent
Li et al.

(10) Patent No.: US 10,246,475 B2
(45) Date of Patent: Apr. 2, 2019

(54) MULTIDENTATE DINUCLEAR CYCLOMETALLATED PLATINUM COMPLEXES CONTAINING N-(PYRIMIDIN-2-YL)-CARBAZOLE AND ITS ANALOGUES

(71) Applicants: Zhejiang University of Technology, Hangzhou (CN); AAC Microtech (Changzhou) Co., Ltd., Changzhou (CN)

(72) Inventors: Guijie Li, Hangzhou (CN); Yuanbin She, Hangzhou (CN); Xiangdong Zhao, Hangzhou (CN); Shaohai Chen, Saratoga, CA (US)

(73) Assignees: ZHEJIANG UNIVERSITY OF TECHNOLOGY, Hangzhou, Zhejiang Province (CN); AAC MICROTECH(CHANGZHOU)CO., LTD., Changzhou, Jiangsu Province (CN)

( * ) Notice: Subject to any disclaimer, the term of this patent is extended or adjusted under 35 U.S.C. 154(b) by 0 days.

(21) Appl. No.: 15/709,303

(22) Filed: Sep. 19, 2017

(65) Prior Publication Data
US 2019/0010179 A1 Jan. 10, 2019

(30) Foreign Application Priority Data
Jul. 4, 2017 (CN) .......................... 2017 1 0537914

(51) Int. Cl.
| | |
|---|---|
| *C09K 11/06* | (2006.01) |
| *C07F 15/00* | (2006.01) |
| *H01L 51/00* | (2006.01) |
| *C09K 11/02* | (2006.01) |
| *H01L 51/50* | (2006.01) |

(52) U.S. Cl.
CPC ........ *C07F 15/0086* (2013.01); *C09K 11/025* (2013.01); *C09K 11/06* (2013.01); *H01L 51/009* (2013.01); *C09K 2211/1029* (2013.01); *C09K 2211/1044* (2013.01); *C09K 2211/185* (2013.01); *H01L 51/5016* (2013.01)

(58) Field of Classification Search
CPC ..... H01L 51/009; C09K 11/06; C09K 11/025; C07F 15/0086
USPC ........................................................ 544/225
See application file for complete search history.

(56) References Cited

U.S. PATENT DOCUMENTS 9,879,039 B2 * 1/2018 Li ....................... H01L 51/0087

* cited by examiner

*Primary Examiner* — Kahsay Habte
(74) *Attorney, Agent, or Firm* — Na Xu; IPro, PLLC

(57) ABSTRACT

Disclosed herein are multidentate dinuclear cyclometallated platinum complexes. The complexes are suitable as emitting materials or host materials in OLED devices, the materials having one of the following structures:

Formula I

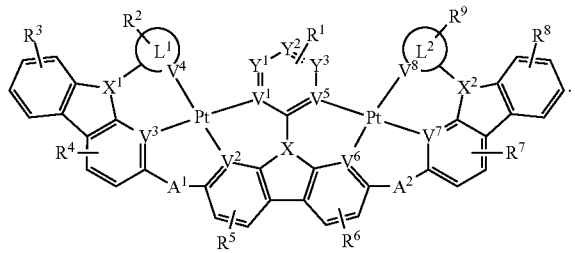

13 Claims, 3 Drawing Sheets

Formula I

Up: experimental data;   Down: theoretical data.

MULTIDENTATE DINUCLEAR CYCLOMETALLATED PLATINUM COMPLEXES CONTAINING N-(PYRIMIDIN-2-YL)-CARBAZOLE AND ITS ANALOGUES

TECHNICAL FIELD

The present disclosure relates to multidentate dinuclear cyclometallated platinum complexes. The complexes are suitable as emitting materials or host materials in OLED devices.

BACKGROUND

Compounds capable of absorbing and/or emitting light can be ideally suited for use in a wide variety of optical and electroluminescent devices, including, for example, photo-absorbing devices such as solar- and photo-sensitive devices, organic light emitting diodes (OLEDs), photo-emitting devices, or devices capable of both photo-absorption and emission and as markers for bio-applications. Much research has been devoted to the discovery and optimization of organic and organometallic materials for using in optical and electroluminescent devices. Generally, research in this area aims to accomplish a number of goals, including improvements in absorption and emission efficiency, improvements in the stability of devices, as well as improvements in processing ability.

Despite significant advances in research devoted to optical and electro-optical materials, for example, red and green phosphorescent organometallic materials are commercial, and they have been used as phosphors in organic light emitting diodes (OLEDs), lighting and advanced displays. Many currently available materials exhibit a number of disadvantages, including poor processing ability, inefficient emission or absorption, and less than ideal stability, among others.

Especially, good blue emitters are very scarce. One big challenge is the stability of the blue devices. And the choice of the host materials has a great effect on the stability and the efficiency of the devices. The lowest triplet excited state energy of the blue phosphors is very high compared with that of the red and green phosphors, which means that the lowest triplet excited state energy of host materials for the blue devices should be even higher. So one of the problems is that there are very limited host materials to be used for the blue devices.

Generally, a chemical structural change will affect the electronic structure of the compounds, which thereby affects the optical properties of the compounds, for example, emission and absorption spectra. Thus, the compounds of this present invention can be tailored or tuned to a specific application that desires a particular emission or absorption characteristic. The optical properties of the metal compounds in this disclosure can be tuned by varying the structure of the ligand surrounding the metal center. For example, the metal compounds having a ligand with electron donating substituents or electron withdrawing substituents can be generally exhibit different optical properties, including emission and absorption spectra.

Owing to the potential of phosphorescent multidentate platinum complexes for harvesting both electrogenerated singlet and triplet excitions to achieve 100% internal quantum efficiency, these complexes are good candidate for the emitting materials of OLEDs. Usually, there are "emitting portion" and "ancillary portion" in ligand of multidentate platinum complexe. If stabilizing substitution(s), such as conjugated group(s), aryl or heteroaromatic substitution(s) and so on, were introduced into the emitting portion. The "Highest Occupied Molecular Orbital" (HOMO) and/or "Lowest Unoccupied Molecular Orbital" (LUMO) energy level may be changed. So the energy gap between the HOMO and LUMO can be tuned. Thus the emission spectra of phosphorescent tetradentate platinum complexes can be modified to lesser or greater extents, such that the emission spectra can become narrower or broader, and/or such that the emission spectra can exhibit a blue shift or a red shift.

Thus, a need exists for new materials which exhibit improved performance in optical emitting and absorbing applications. Accordingly, such compounds, compositions, and devices comprising the same are disclosed herein.

SUMMARY

The present disclosure relates to multidentate dinuclear cyclometallated platinum complexes. The complexes are suitable as emitting materials or host materials in OLED devices.

Disclosed herein are compounds of Formula I:

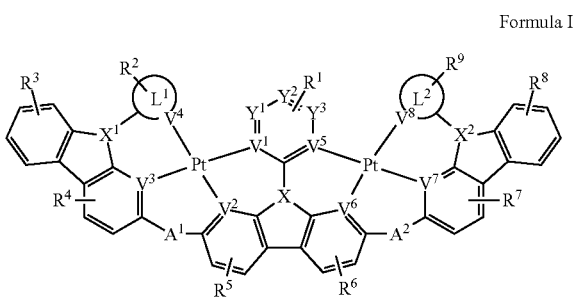

Formula I wherein each of $L^1$ and $L^2$ is independently a six-membered carbocyclic, heterocyclic, heteroaryl ring.

wherein $V^1$, $V^2$, $V^3$, $V^4$, $V^5$, $V^6$, $V^7$ and $V^8$ are coordinated with Pt and are each independently comprise N and C; and at least two of $V^1$, $V^2$, $V^3$ and $V^4$ are N, at least two of $V^5$, $V^6$, $V^7$ and $V^8$ are N.

wherein each of $A^1$ and $A^2$ is independently selected from the group consisting O, S, $CH_2$, $CD_2$, $CR^aR^b$, C=O, $SiR^aR^b$, $GeH_2$, $GeR^aR^b$, NH, $NR^c$, PH, $PR^c$, $R^cP$=O, $AsR^c$, $R^cAs$=O, S=O, $SO_2$, Se, Se=O, $SeO_2$, BH, $BR^c$, $R^cBi$=O, BiH, or $BiR^c$.

wherein each of X, $X^1$ and $X^2$ is independently selected from the group consisting N, B, CH, CD, $CR^a$, SiH, SiD, $SiR^a$, GeH, GeD, $GeR^d$, P, P=O, As, As=O, Bi or Bi=O.

wherein $R^1$, $R^2$, $R^3$, $R^4$, $R^5$, $R^6$, $R^7$, $R^8$ and $R^9$ may represent mono-, di, tri, tetra-substitutions, or no substitution, and $R^1$, $R^2$, $R^3$, $R^4$, $R^5$, $R^6$, $R^7$, $R^8$, $R^9$, $R^a$, $R^b$, $R^c$ and $R^d$ are independently selected from the group consisting hydrogen, deuterium, aryl, cycloalkyl, cycloalkenyl, heterocyclyl, heteroaryl, alkyl, alkenyl, alkynyl, halogen, hydroxyl, thiol, nitro, cyano, amino, a mono- or di-alkylamino, a mono- or diaryl amino, alkoxy, aryloxy, haloalkyl, aralkyl, ester, nitrile, isonitrile, heteroary, alkoxycarbonyl, acylamino, alkoxycarbonylamino, aryloxycarbonylamino, sulfonylamino, sulfamoyl, carbamoyl, alkylthio, sulfinyl, ureido, phosphoramide, amercapto, sulfo, carboxyl, hydrzino, substituted silyl, or polymerizable, or any conjugate or combination thereof. Two or more adjacent $R^1$, $R^2$, $R^3$, $R^4$, $R^5$, $R^6$, $R^7$, $R^8$ and $R^9$ are optionally joined to form a fused ring.

wherein $R^a$, $R^b$, $R^c$ and $R^d$ may represent mono-, di, tri, tetra-substitutions, or no substitution, and $R^a$, $R^b$, $R^c$ and $R^d$ are independently selected from the group consisting hydrogen, deuterium, aryl, cycloalkyl, cycloalkenyl, heterocyclyl, heteroaryl, alkyl, alkenyl, alkynyl, halogen, hydroxyl, thiol, nitro, cyano, amino, a mono- or di-alkylamino, a mono- or diaryl amino, alkoxy, aryloxy, haloalkyl, aralkyl, ester, nitrile, isonitrile, heteroary, alkoxycarbonyl, acylamino, alkoxycarbonylamino, aryloxycarbonylamino, sulfonylamino, sulfamoyl, carbamoyl, alkylthio, sulfinyl, ureido, phosphoramide, amercapto, sulfo, carboxyl, hydrzino, substituted silyl, or polymerizable, or any conjugate or combination thereof.

In one aspect,

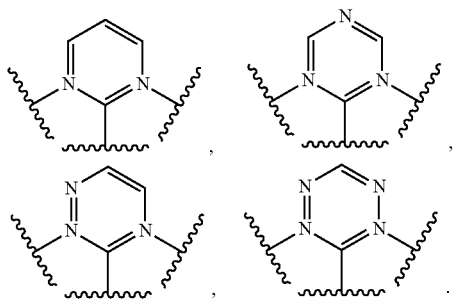

is selected from the group consisting

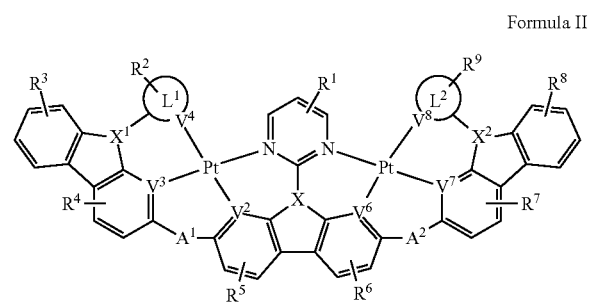

In one aspect, the compound has the structure of Formula II, Formula III, Formula IV and Formula V:

Formula II

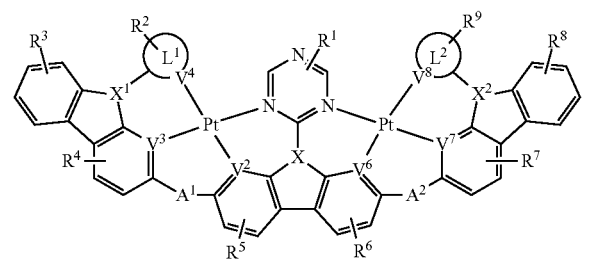

Formula III

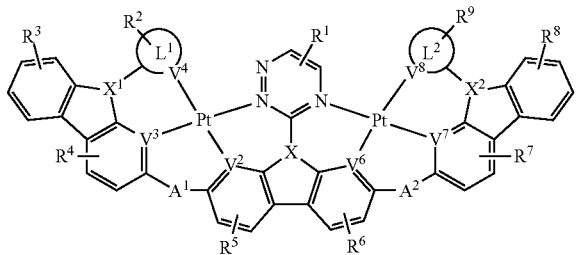

Formula IV

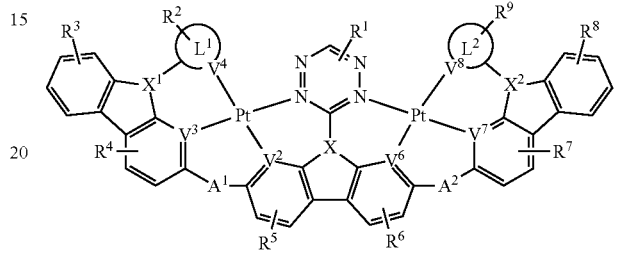

Formula V

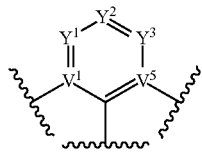

Also disclosed herein are compositions comprising one or more compounds disclosed herein.

Also disclosed herein are devices, such as OLEDs, comprising one or more compounds or compositions disclosed herein.

BRIEF DESCRIPTION OF THE FIGURES

The accompanying figures, which are incorporated in and constitute a part of this specification, illustrate several non-limiting aspects and together with the description serve to explain the principles of the invention.

Figure 1:
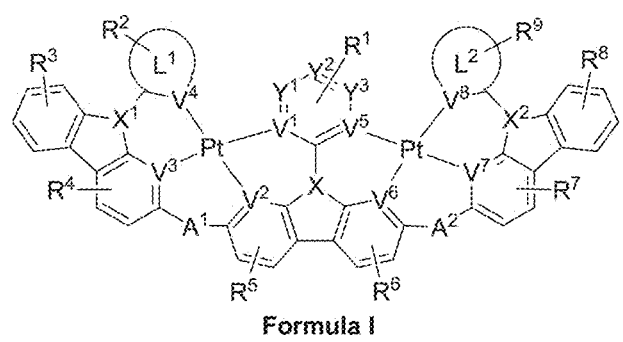
FIG. 1 shows a compound of Formula I.
Figure 2:
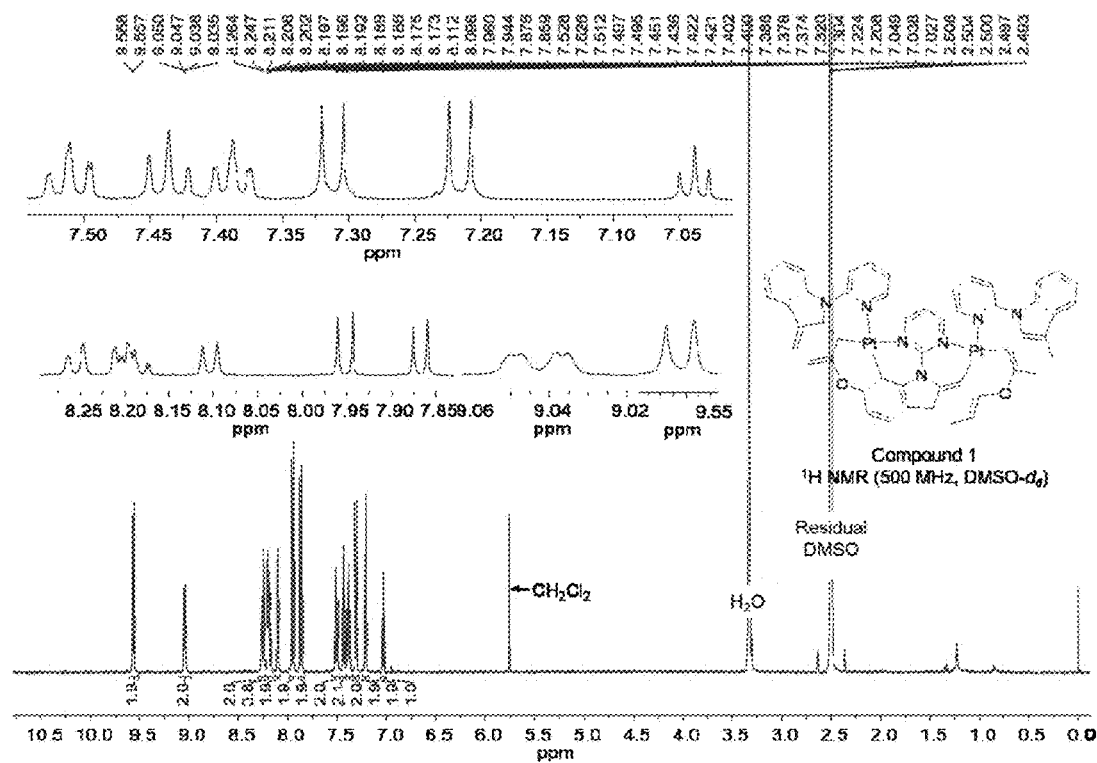
FIG. 2 shows the $^1$H NMR spectrum of Compound 1 in MDSO-$d_6$.
Figure 3:
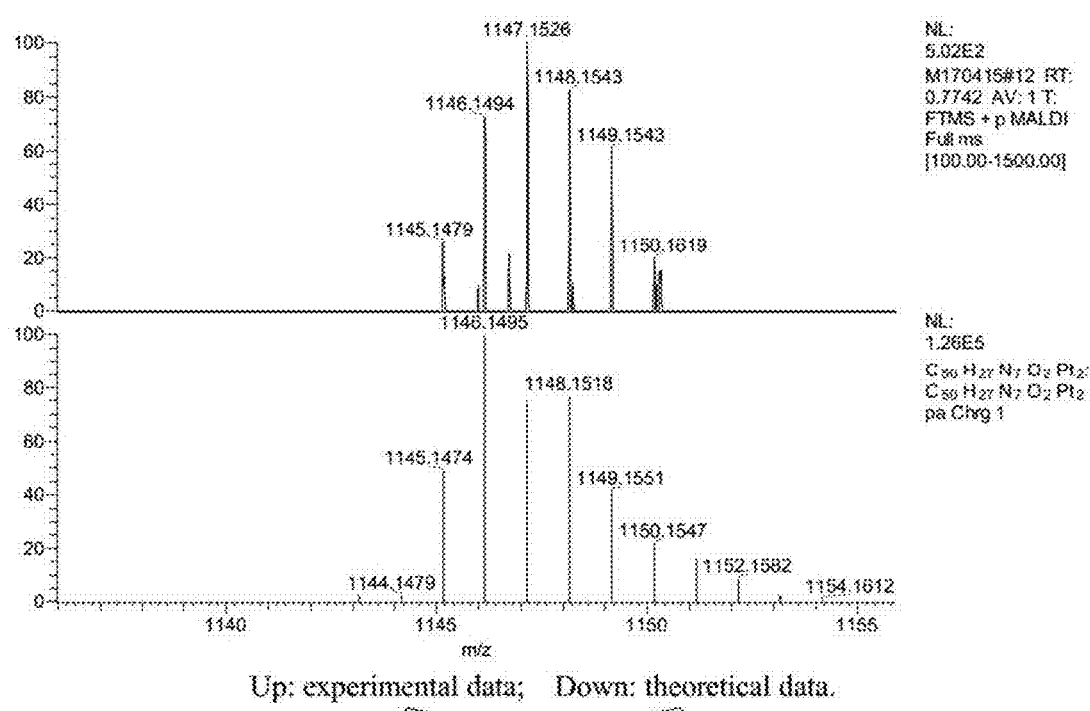
FIG. 3 shows the High Resolution MS of Compound 1.
Figure 3:
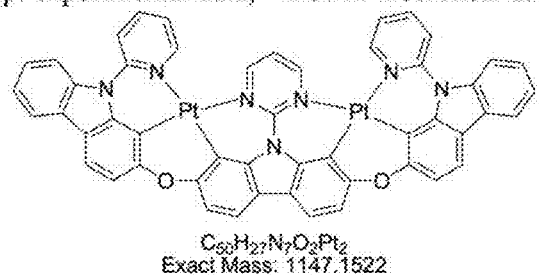

Additional aspects of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

The present invention can be understood more readily by reference to the following detailed description of the invention and the Examples included therein.

Before the present compounds, devices, and/or methods are disclosed and described, it is to be understood that they are not limited to specific synthetic methods unless otherwise specified, or to particular reagents unless otherwise specified, as such can, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

As used in the specification and the appended claims, the singular forms "a", "an", and "the" include plural referents unless the context clearly dictates otherwise. Thus, for example, reference to "a component" includes mixtures of two or more components.

As used herein, the terms "optional" or "optionally" means that the subsequently described event or circumstance can or cannot occur, and that the description includes instances where said event or circumstance occurs and instances where it does not.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

As referred to herein, a linking atom can connect two groups such as, for example, an N and C group. A linking group is in one aspect disclosed as A, $A^1$, and/or $A^3$ herein. The linking atom can optionally, if valency permits, have other chemical moieties attached. For example, in one aspect, an oxygen would not have any other chemical groups attached as the valency is satisfied once it is bonded to two groups (e.g., N and/or C groups). In another aspect, when carbon is the linking atom, two additional chemical moieties can be attached to the carbon. Suitable chemical moieties includes, but are not limited to, hydrogen, hydroxyl, alkyl, alkoxy, =O, halogen, nitro, amine, amide, thiol, aryl, heteroaryl, cycloalkyl, and heterocyclyl.

The term "cyclic structure" or the like terms used herein refer to any cyclic chemical structure which includes, but is not limited to, aryl, heteroaryl, cycloalkyl, cycloalkenyl, heterocyclyl, carbene, and N-heterocyclic carbene.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$R^1$," "$R^2$," "$R^3$," and "$R^4$" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The term "polyalkylene group" as used herein is a group having two or more $CH_2$ groups linked to one another. The polyalkylene group can be represented by the formula $-(CH_2)_a-$, where "a" is an integer of from 2 to 500.

The terms "alkoxy" and "alkoxyl" as used herein to refer to an alkyl or cycloalkyl group bonded through an ether linkage; that is, an "alkoxy" group can be defined as $-OR^1$ where $R^1$ is alkyl or cycloalkyl as defined above. "Alkoxy" also includes polymers of alkoxy groups as just described; that is, an alkoxy can be a polyether such as $-OR^1-OR^2$ or $-OR^1-(OR^2)_a-OR^3$, where "a" is an integer of from 1 to 200 and $R^1$, $R^2$, and $R^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(R^1R^2)C=C(R^3R^4)$ are intended to include both the E and Z isomers. This can be presumed in structural formulae herein wherein an asymmetric alkene is present, or it can be explicitly indicated by the bond symbol $C=C$. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., $C=C$. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl." where at least one of the carbon atoms of the ring is replaced with a heteroatom such as, but not limited to, nitrogen, oxygen, sulfur, or phosphorus. The cycloalkenyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl." defines a group that contains an aromatic group that does not contain a heteroatom. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by the formula $-C(O)H$. Throughout this specification "C(O)" is a short hand notation for a carbonyl group, i.e., $C=O$.

The terms "amine" or "amino" as used herein are represented by the formula $-NR^1R^2$, where $R^1$ and $R^2$ can be, independently, hydrogen or alkyl, cycloalkyl, alkenyl, cycloalkenyl, alkynyl, cycloalkynyl, aryl, or heteroaryl group as described herein.

The term "alkylamino" as used herein is represented by the formula $-NH(-alkyl)$ where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl)amino group, hexylamino group, and the like.

The term "dialkylamino" as used herein is represented by the formula $-N(-alkyl)_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —OC(O)R¹ or —C(O)OR¹, where R¹ can be alkyl, cycloalkyl, alkenyl, cycloalkenyl, alkynyl, cycloalkynyl, aryl, or heteroaryl group as described herein. The term "polyester" as used herein is represented by the formula —(R¹O(O)C—R²—C(O)O)$_a$— or —(R¹O(O)C—R²—OC(O))$_a$—, where R¹ and R² can be, independently, an alkyl, cycloalkyl, alkenyl, cycloalkenyl, alkynyl, cycloalkynyl, aryl, or heteroaryl group described herein and "a" is an interger from 1 to 500. "Polyester" is as the term used to describe a group that is produced by the reaction between a compound having at least two carboxylic acid groups with a compound having at least two hydroxyl groups.

The term "ether" as used herein is represented by the formula R¹OR², where R¹ and R² can be, independently, an alkyl, cycloalkyl, alkenyl, cycloalkenyl, alkynyl, cycloalkynyl, aryl, or heteroaryl group described herein. The term "polyether" as used herein is represented by the formula —(R¹O—R²O)$_a$—, where R¹ and R² can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The term "halide" as used herein refers to the halogens fluorine, chlorine, bromine, and iodine.

The term "heterocyclyl," as used herein refers to single and multi-cyclic non-aromatic ring systems and "heteroaryl as used herein refers to single and multi-cyclic aromatic ring systems: in which at least one of the ring members is other than carbon. The terms includes azetidine, dioxane, furan, imidazole, isothiazole, isoxazole, morpholine, oxazole, oxazole, including, 1,2,3-oxadiazole, 1,2,5-oxadiazole and 1,3,4-oxadiazole, piperazine, piperidine, pyrazine, pyrazole, pyridazine, pyridine, pyrimidine, pyrrole, pyrrolidine, tetrahydrofuran, tetrahydropyran, tetrazine, including 1,2,4,5-tetrazine, tetrazole, including 1,2,3,4-tetrazole and 1,2,4,5-tetrazole, thiadiazole, including, 1,2,3-thiadiazole, 1,2,5-thiadiazole, and 1,3,4-thiadiazole, thiazole, thiophene, triazine, including 1,3,5-triazine and 1,2,4-triazine, triazole, including, 1,2,3-triazole, 1,3,4-triazole, and the like.

The term "hydroxyl" as used herein is represented by the formula —OH.

The term "ketone" as used herein is represented by the formula R¹C(O)R², where R¹ and R² can be, independently, an alkyl, cycloalkyl, alkenyl, cycloalkenyl, alkynyl, cycloalkynyl, aryl, or heteroaryl group as described herein.

The term "azide" as used herein is represented by the formula —N₃.

The term "nitro" as used herein is represented by the formula —NO₂.

The term "nitrile" as used herein is represented by the formula —CN.

The term "silyl" as used herein is represented by the formula —SiR¹R²R³, where R¹, R², and R³ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —S(O)R¹, —S(O)₂R¹, —OS(O)₂R¹, or —OS(O)₂OR¹, where R¹ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —S(O)₂R¹, where R¹ can be hydrogen or an alkyl, cycloalkyl, alkenyl, cycloalkenyl, alkynyl, cycloalkynyl, aryl, or heteroaryl group as described herein. The term "sulfone" as used herein is represented by the formula R¹S(O)₂R², where R¹ and R² can be, independently, an alkyl, cycloalkyl, alkenyl, cycloalkenyl, alkynyl, cycloalkynyl, aryl, or heteroaryl group as described herein. The term "sulfoxide" as used herein is represented by the formula R¹S(O)R², where R¹ and R² can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

"R¹," "R²," "R³," "Rⁿ," where n is an integer, as used herein can, independently, possess one or more of the groups listed above. For example, if R¹ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

In some aspects, a structure of a compound can be represented by a formula:

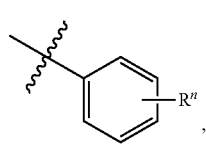

, which is understood to be equivalent to a formula:

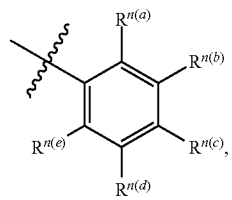

wherein n is typically an integer. That is, $R''$ is understood to represent five independent substituents, $R''^{(a)}$, $R''^{(b)}$, $R''^{(c)}$, $R''^{(d)}$, $R''^{(e)}$. By "independent substituents," it is meant that each R substituent can be independently defined. For example, if in one instance $R''^{(a)}$ is halogen, then $R''^{(b)}$ is not necessarily halogen in that instance.

Several references to $R^1$, $R^2$, $R^3$, $R^4$, $R^5$, $R^6$, etc. are made in chemical structures and moieties disclosed and described herein. Any description of $R^1$, $R^2$, $R^3$, $R^4$, $R^5$, $R^6$, etc. in the specification is applicable to any structure or moiety reciting $R^1$, $R^2$, $R^3$, $R^4$, $R^5$, $R^6$, etc. respectively.

1. Compounds

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

Excitons decay from singlet excited states to ground state to yield prompt luminescence, which is fluorescence. If Excitons decay from triplet excited states to ground state to generate luminescence, which is phosphorescence. Because the strong spin-orbit coupling of the heavy metal atom enhances intersystem crossing (ISC) very efficiently between singlet and triplet excited state, phosphorescent metal complexes, such as platinum complexes, have demonstrated their potential to harvest both the singlet and triplet excitons to achieve 100)% internal quantum efficiency. Thus phosphorescent metal complexes are good candidates as dopants in the emissive layer of organic light emitting devices (OLEDs) and a great deal of attention has been received both in the academic and industrial fields. And much achievement has been made in the past decade to led to the lucrative commercialization of the technology, for example, OLEDs have been used in advanced displays in smart phones, televisions and digital cameras.

However, to date, blue electroluminescent devices remain the most challenging area of this technology, one big problem is the stability of the blue devices. It has been proved that the choice of host materials is very important to the stability of the blue devices. But the lowest triplet excited state ($T_1$) energy of the blue phosphors is very high, which means that the lowest triplet excited state ($T_1$) energy of host materials for the blue devices should be even higher. This leads to much difficulty in the development of the host materials for the blue devices.

The metal complexes of this present invention can be tailored or tuned to a specific application that desires a particular emission or absorption characteristic. The optical properties of the metal complexes in this disclosure can be tuned by varying the structure of the ligand surrounding the metal center or varying the structure of fluorescent luminophore(s) on the ligands. For example, the metal complexes having a ligand with electron donating substituents or electron withdrawing substituents can be generally exhibit different optical properties, including emission and absorption spectra. The color of the metal complexes can be tuned by modifying the conjugated groups on the fluorescent luminophores and ligands.

The emission of such inventive complexes can be tuned, for example, from the ultraviolet to near-infrared, by, for example, modifying the ligand or fluorescent luminophore structure. A fluorescent luminophore is a group of atoms in an organic molecule, which can absorb energy to generate singlet excited state(s), the singlet exciton(s) produce(s) decay rapidly to yield prompt luminescence. In another aspect, the inventive complexes can provide emission over a majority of the visible spectrum. In a specific example, the inventive complexes can emit light over a range of from about 400 nm to about 700 nm. In another aspect, the inventive complexes have improved stability and efficiency over traditional emission complexes. In yet another aspect, the inventive complexes can be useful as luminescent labels in, for example, bio-applications, anti-cancer agents, emitters in organic light emitting diodes (OLED), or a combination thereof. In another aspect, the inventive complexes can be useful in light emitting devices, such as, for example, compact fluorescent lamps (CFL), light emitting diodes (LED), incandescent lamps, and combinations thereof.

Disclosed herein are compounds or compound complexes comprising platinum. The terms compound or compound complex are used interchangeably herein. In one aspect, the compounds discloses herein have a neutral charge.

The compounds disclosed herein, can exhibit desirable properties and have emission and/or absorption spectra that can be tuned via the selection of appropriate ligands. In another aspect, the present invention can exclude any one or more of the compounds, structures, or portions thereof, specifically recited herein.

The compounds disclosed herein are suited for use in a wide variety of optical and electro-optical devices, including, but not limited to, photo-absorbing devices such as solar- and photo-sensitive devices, organic light emitting diodes (OLEDs), photo-emitting devices, or devices capable of both photo-absorption and emission and as markers for bio-applications.

As briefly described above, the disclosed compounds are platinum complexes. In one aspect, the compounds disclosed herein can be used as host materials for OLED applications, such as full color displays.

The compounds disclosed herein are useful in a variety of applications. As light emitting materials, the compounds can be useful in organic light emitting diodes (OLED)s, luminescent devices and displays, and other light emitting devices.

In another aspect, the compounds can provide improved efficiency and/or operational lifetimes in lighting devices, such as, for example, organic light emitting devices, as compared to conventional materials.

The compounds of the invention can be made using a variety of methods, including, but not limited to those recited in the examples provided herein.

The compound disclosed herein can be a delayed fluorescent and/or phosphorescent emitter. In one aspect, the compounds disclosed herein can be a delayed fluorescent emitter. In another aspect, the compounds disclosed herein can be a phosphorescent emitter. In yet another aspect, the compounds disclosed herein can be a delayed fluorescent emitter and a phosphorescent emitter.

The present disclosure relates to multidentate dinuclear cyclometallated platinum complexes. The complexes are suitable as emitting materials or host materials in OLED devices.

Disclosed herein are compounds of Formula I:

Formula I

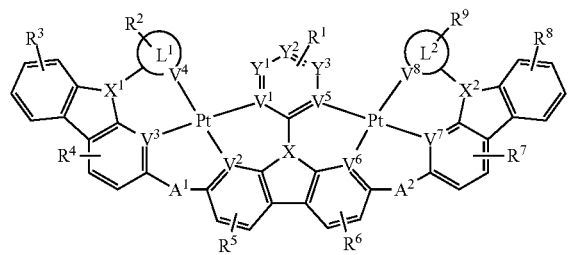

wherein each of $L^1$ and $L^2$ is independently a six-membered carbocyclic, heterocyclic, heteroaryl ring.

wherein $V^1$, $V^2$, $V^3$, $V^4$, $V^5$, $V^6$, $V^7$ and $V^8$ are coordinated with Pt and are each independently comprise N and C; and at least two of $V^1$, $V^2$, $V^3$ and $V^4$ are N, at least two of $V^5$, $V^6$, $V^7$ and $V^8$ are N.

wherein each of $A^1$ and $A^2$ is independently selected from the group consisting O, S, $CH_2$, $CD_2$, $CR^aR^b$, C=O, $SiR^aR^b$, $GeH_2$, $GeR^aR^b$, NH, $NR^c$, PH, $PR^c$, $R^cP$=O, $AsR^c$, $R^cAs$=O, S=O, $SO_2$, Se, Se=O, $SeO_2$, BH, $BR^c$, $R^cBi$=O, BiH, or $BiR^c$.

wherein each of X, $X^1$ and $X^2$ is independently selected from the group consisting N, B, CH, CD, $CR^a$, SiH, SiD, $SiR^a$, GeH, GeD, $GeR^d$, P, P=O, As, As=O, Bi or Bi=O.

wherein $R^1$, $R^2$, $R^3$, $R^4$, $R^5$, $R^6$, $R^7$, $R^8$ and $R^9$ may represent mono-, di, tri, tetra-substitutions, or no substitution, and $R^1$, $R^2$, $R^3$, $R^4$, $R^5$, $R^6$, $R^7$, $R^8$, $R^9$, $R^a$, $R^b$, $R^c$ and $R^d$ are independently selected from the group consisting hydrogen, deuterium, aryl, cycloalkyl, cycloalkenyl, heterocyclyl, heteroaryl, alkyl, alkenyl, alkynyl, halogen, hydroxyl, thiol, nitro, cyano, amino, a mono- or di-alkylamino, a mono- or diaryl amino, alkoxy, aryloxy, haloalkyl, aralkyl, ester, nitrile, isonitrile, heteroary, alkoxycarbonyl, acylamino, alkoxycarbonylamino, aryloxycarbonylamino, sulfonylamino, sulfamoyl, carbamoyl, alkylthio, sulfinyl, ureido, phosphoramide, amercapto, sulfo, carboxyl, hydrzino, substituted silyl, or polymerizable, or any conjugate or combination thereof. Two or more adjacent $R^1$, $R^2$, $R^3$, $R^4$, $R^5$, $R^6$, $R^7$, $R^8$ and $R^9$ are optionally joined to form a fused ring.

wherein $R^a$, $R^b$, $R^c$ and $R^d$ may represent mono-, di, tri, tetra-substitutions, or no substitution, and $R^a$, $R^b$, $R^c$ and $R^d$ are independently selected from the group consisting hydrogen, deuterium, aryl, cycloalkyl, cycloalkenyl, heterocyclyl, heteroaryl, alkyl, alkenyl, alkynyl, halogen, hydroxyl, thiol, nitro, cyano, amino, a mono- or di-alkylamino, a mono- or diaryl amino, alkoxy, aryloxy, haloalkyl, aralkyl, ester, nitrile, isonitrile, heteroary, alkoxycarbonyl, acylamino, alkoxycarbonylamino, aryloxycarbonylamino, sulfonylamino, sulfamoyl, carbamoyl, alkylthio, sulfinyl, ureido, phosphoramide, amercapto, sulfo, carboxyl, hydrzino, substituted silyl, or polymerizable, or any conjugate or combination thereof.

In one aspect,

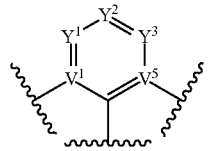

is selected from the group consisting

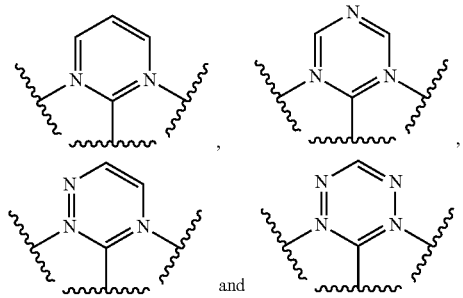

and            .

In one aspect, the compound has the structure of Formula II, Formula III, Formula IV and Formula V:

Formula II

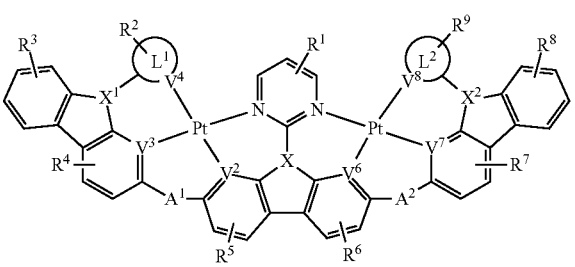

Formula III

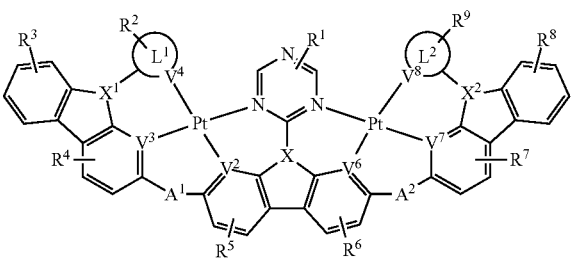

Formula IV

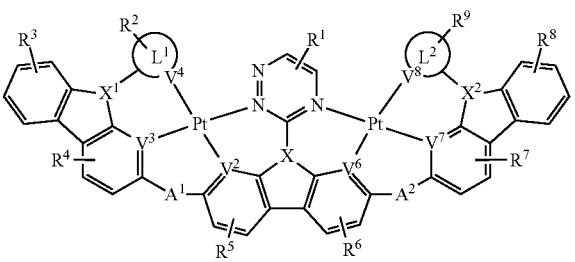

-continued

Formula V

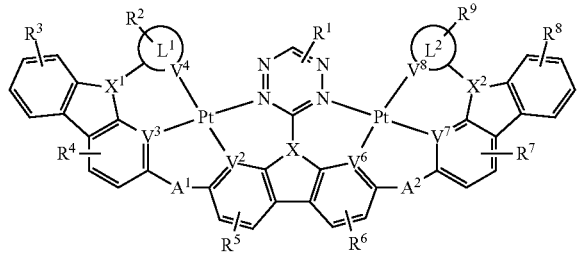

A. L Groups

In one aspect, $L^1$ is a six-membered carbocyclic, heterocyclic, heteroaryl ring.

In another aspect, $L^2$ is a six-membered carbocyclic, heterocyclic, heteroaryl ring.

B. V Groups

In one aspect, $V^1$, $V^2$, $V^3$, $V^4$, $V^5$, $V^6$, $V^7$ and $V^8$ are coordinated with $M^1$ or $M^2$ and are each independently comprise N and C; and at least two of $V^1$, $V^2$, $V^3$ and $V^4$ are N, at least two of $V^5$, $V^6$, $V^7$ and $V^8$ are N.

In another aspect, $V^1$ and $V^4$ are N, $V^2$ and $V^3$ are C, $V^5$ and $V^8$ are N, $V^6$ and $V^7$ are C.

In yet another aspect. $V^1$, $V^2$ and $V^3$ are C, and $V^4$ is N, $V^5$ and $V^8$ are N, $V^6$ and $V^7$ are C.

In yet another aspect, $V^1$ and $V^3$ are C, $V^2$ and $V^4$ are N, $V^5$ and $V^7$ are C, $V^6$ and $V^8$ are N.

C. A Groups

In one aspect, each of $A^1$ and $A^2$ is independently selected from the group consisting O, S, $CH_2$, $CD_2$, $CR^aR^b$, C=O, $SiR^aR^b$, $GeH_2$, $GeR^aR^b$, NH, $NR^c$, PH, $PR^c$, $R^cP$=O. $AsR^c$, $R^cAs$=O, S=O, $SO_2$, Se, Se=O, $SeO_2$, BH, $BR^c$, $R^cBi$=O, BiH, or $BiR^c$.

In another aspect, $A^1$ is O, $A^2$ is O.

In another aspect, $A^1$ is O, $A^2$ is S.

In another aspect, $A^1$ is $CR^aR^b$, $A^2$ is $CR^aR^b$.

In another aspect, $A^1$ is $NR^c$, $A^2$ is $NR^c$.

In another aspect, $A^1$ is O, $A^2$ is $NR^c$.

In another aspect, $A^1$ is $CR^aR^b$, $A^2$ is $NR^c$.

In yet another aspect, $A^1$ is $BR^c$, $A^2$ is $BR^c$.

D. X Groups

In one aspect, each of X, $X^1$ and $X^2$ is independently selected from the group consisting N, B, CH, CD, $CR^a$, SiH, SiD, $SiR^a$, GeH, GeD, $GeR^d$, P, P=O, As, As=O, Bi or Bi=O.

In another aspect, X is N, $X^1$ is N, $X^2$ is N.
In another aspect, X is B, $X^1$ is B, $X^2$ is B.
In another aspect, X is B, $X^1$ is N, $X^2$ is N.
In another aspect, X is N, $X^1$ is B, $X^2$ is N.
In another aspect, X is N, $X^1$ is N, $X^2$ is B.
In another aspect, X is P=O, $X^1$ is N, $X^2$ is N.
In another aspect, X is N, $X^1$ is P=O, $X^2$ is N.
In another aspect, X is N, $X^1$ is N, $X^2$ is P=O.
In another aspect, X is N, $X^1$ is B, $X^2$ is B.
In another aspect, X is B, $X^1$ is N, $X^2$ is B.
In another aspect, X is B, $X^1$ is B, $X^2$ is N.
In another aspect, X is P=O, $X^1$ is N, $X^2$ is P=O.
In another aspect, X is $CR^a$, $X^1$ is $CR^a$, $X^2$ is $CR^a$.
In another aspect, X is $CR^a$, $X^1$ is N, $X^2$ is N.
In another aspect, X is N, $X^1$ is $CR^a$, $X^2$ is N.
In another aspect, X is N, $X^1$ is N, $X^2$ is $CR^a$.
In another aspect, X is $CR^a$, $X^1$ is N, $X^2$ is $CR^a$.
In another aspect, X is N, $X^1$ is $CR^a$, $X^2$ is $CR^a$.
In another aspect, X is $CR^a$, $X^1$ is $CR^a$, $X^2$ is N.

In another aspect, X is N, $X^1$ is $SiR^a$, $X^2$ is N.
In another aspect, X is N, $X^1$ is N, $X^2$ is $SiR^a$.
In another aspect, X is $SiR^a$, $X^1$ is N, $X^2$ is $SiR^a$.
In another aspect, X is N, $X^1$ is $SiR^a$, $X^2$ is $SiR^a$.
In yet another aspect, X is $SiR^a$, $X^1$ is $SiR^a$, $X^2$ is N.

E. R Groups

In one aspect, $R^1$ is present. In another aspect, $R^1$ is absent.

In one aspect, $R^1$ is a mono-substitution. In another aspect, $R^1$ is a di-substitution. In another aspect, $R^1$ is a tri-substitution. In yet another aspect, $R^1$ is a tetra-substitution.

In another aspect, $R^1$ is selected from the group consisting hydrogen, deuterium, aryl, cycloalkyl, cycloalkenyl, heterocyclyl, heteroaryl, alkyl, alkenyl, alkynyl, halogen, hydroxyl, thiol, nitro, cyano, amino, a mono- or di-alkylamino, a mono- or diaryl amino, alkoxy, aryloxy, haloalkyl, aralkyl, ester, nitrile, isonitrile, heteroary, alkoxycarbonyl, acylamino, alkoxycarbonylamino, aryloxycarbonylamino, sulfonylamino, sulfamoyl, carbamoyl, alkylthio, sulfinyl, ureido, phosphoramide, amercapto, sulfo, carboxyl, hydrzino, substituted silyl, or polymerizable, or any conjugate or combination thereof.

In one aspect, $R^2$ is present. In another aspect, $R^2$ is absent.

In one aspect, $R^2$ is a mono-substitution. In another aspect, $R^2$ is a di-substitution. In another aspect, $R^2$ is a tri-substitution. In yet another aspect, $R^2$ is a tetra-substitution.

In another aspect, $R^2$ is selected from the group consisting hydrogen, deuterium, aryl, cycloalkyl, cycloalkenyl, heterocyclyl, heteroaryl, alkyl, alkenyl, alkynyl, halogen, hydroxyl, thiol, nitro, cyano, amino, a mono- or di-alkylamino, a mono- or diaryl amino, alkoxy, aryloxy, haloalkyl, aralkyl, ester, nitrile, isonitrile, heteroary, alkoxycarbonyl, acylamino, alkoxycarbonylamino, aryloxycarbonylamino, sulfonylamino, sulfamoyl, carbamoyl, alkylthio, sulfinyl, ureido, phosphoramide, amercapto, sulfo, carboxyl, hydrzino, substituted silyl, or polymerizable, or any conjugate or combination thereof.

In one aspect, $R^3$ is present. In another aspect, $R^3$ is absent.

In one aspect, $R^3$ is a mono-substitution. In another aspect, $R^3$ is a di-substitution. In another aspect, $R^3$ is a tri-substitution. In yet another aspect, $R^3$ is a tetra-substitution.

In another aspect, $R^3$ is selected from the group consisting hydrogen, deuterium, aryl, cycloalkyl, cycloalkenyl, heterocyclyl, heteroaryl, alkyl, alkenyl, alkynyl, halogen, hydroxyl, thiol, nitro, cyano, amino, a mono- or di-alkylamino, a mono- or diaryl amino, alkoxy, aryloxy, haloalkyl, aralkyl, ester, nitrile, isonitrile, heteroary, alkoxycarbonyl, acylamino, alkoxycarbonylamino, aryloxycarbonylamino, sulfonylamino, sulfamoyl, carbamoyl, alkylthio, sulfinyl, ureido, phosphoramide, amercapto, sulfo, carboxyl, hydrzino, substituted silyl, or polymerizable, or any conjugate or combination thereof.

In one aspect, $R^4$ is present. In another aspect, $R^4$ is absent.

In one aspect, $R^4$ is a mono-substitution. In another aspect, $R^4$ is a di-substitution.

In another aspect, $R^4$ is selected from the group consisting hydrogen, deuterium, aryl, cycloalkyl, cycloalkenyl, heterocyclyl, heteroaryl, alkyl, alkenyl, alkynyl, halogen, hydroxyl, thiol, nitro, cyano, amino, a mono- or di-alkylamino, a mono- or diaryl amino, alkoxy, aryloxy, haloalkyl, aralkyl, ester, nitrile, isonitrile, heteroary, alkoxycarbonyl, acylamino, alkoxycarbonylamino, aryloxycarbonylamino, sulfonylamino, sulfamoyl, carbamoyl, alkylthio, sulfinyl, ureido, phosphoramide, amercapto, sulfo, carboxyl, hydrzino, substituted silyl, or polymerizable, or any conjugate or combination thereof.

In one aspect, $R^5$ is present. In another aspect, $R^5$ is absent.

In one aspect, $R^5$ is a mono-substitution. In another aspect, $R^5$ is a di-substitution.

In another aspect, $R^5$ is selected from the group consisting hydrogen, deuterium aryl, cycloalkyl, cycloalkenyl, heterocyclyl, heteroaryl, alkyl, alkenyl, alkynyl, halogen, hydroxyl, thiol, nitro, cyano, amino, a mono- or di-alkylamino, a mono- or diaryl amino, alkoxy, aryloxy, haloalkyl, aralkyl, ester, nitrile, isonitrile, heteroary, alkoxycarbonyl, acylamino, alkoxycarbonylamino, aryloxycarbonylamino, sulfonylamino, sulfamoyl, carbamoyl, alkylthio, sulfinyl, ureido, phosphoramide, amercapto, sulfo, carboxyl, hydrzino, substituted silyl, or polymerizable, or any conjugate or combination thereof.

In one aspect, $R^6$ is present. In another aspect, $R^6$ is absent.

In one aspect, $R^6$ is a mono-substitution. In another aspect, $R^6$ is a di-substitution.

In another aspect, $R^6$ is selected from the group consisting hydrogen, deuterium, aryl, cycloalkyl, cycloalkenyl, heterocyclyl, heteroaryl, alkyl, alkenyl, alkynyl, halogen, hydroxyl, thiol, nitro, cyano, amino, a mono- or di-alkylamino, a mono- or diaryl amino, alkoxy, aryloxy, haloalkyl, aralkyl, ester, nitrile, isonitrile, heteroary, alkoxycarbonyl, acylamino, alkoxycarbonylamino, aryloxycarbonylamino, sulfonylamino, sulfamoyl, carbamoyl, alkylthio, sulfinyl, ureido, phosphoramide, amercapto, sulfo, carboxyl, hydrzino, substituted silyl, or polymerizable, or any conjugate or combination thereof.

In one aspect, $R^7$ is present. In another aspect, $R^7$ is absent.

In one aspect, $R^7$ is a mono-substitution. In another aspect, $R^7$ is a di-substitution.

In another aspect, $R^7$ is selected from the group consisting hydrogen, deuterium, aryl, cycloalkyl, cycloalkenyl, heterocyclyl, heteroaryl, alkyl, alkenyl, alkynyl, halogen, hydroxyl, thiol, nitro, cyano, amino, a mono- or di-alkylamino, a mono- or diaryl amino, alkoxy, aryloxy, haloalkyl, aralkyl, ester, nitrile, isonitrile, heteroary, alkoxycarbonyl, acylamino, alkoxycarbonylamino, aryloxycarbonylamino, sulfonylamino, sulfamoyl, carbamoyl, alkylthio, sulfinyl, ureido, phosphoramide, amercapto, sulfo, carboxyl, hydrzino, substituted silyl, or polymerizable, or any conjugate or combination thereof.

In one aspect, $R^8$ is present. In another aspect, $R^8$ is absent.

In one aspect, $R^8$ is a mono-substitution. In another aspect, $R^8$ is a di-substitution. In another aspect, $R^8$ is a tri-substitution. In yet another aspect, $R^8$ is a tetra-substitution.

In another aspect, $R^8$ is selected from the group consisting hydrogen, deuterium, aryl, cycloalkyl, cycloalkenyl, heterocyclyl, heteroaryl, alkyl, alkenyl, alkynyl, halogen, hydroxyl, thiol, nitro, cyano, amino, a mono- or di-alkylamino, a mono- or diaryl amino, alkoxy, aryloxy, haloalkyl, aralkyl, ester, nitrile, isonitrile, heteroary, alkoxycarbonyl, acylamino, alkoxycarbonylamino, aryloxycarbonylamino, sulfonylamino, sulfamoyl, carbamoyl, alkylthio, sulfinyl, ureido, phosphoramide, amercapto, sulfo, carboxyl, hydrzino, substituted silyl, or polymerizable, or any conjugate or combination thereof.

In one aspect, $R^9$ is present. In another aspect, $R^9$ is absent.

In one aspect, $R^9$ is a mono-substitution. In another aspect, $R^9$ is a di-substitution. In another aspect, $R^9$ is a tri-substitution. In yet another aspect, $R^9$ is a tetra-substitution.

In another aspect, $R^9$ is selected from the group consisting hydrogen, deuterium, aryl, cycloalkyl, cycloalkenyl, heterocyclyl, heteroaryl, alkyl, alkenyl, alkynyl, halogen, hydroxyl, thiol, nitro, cyano, amino, a mono- or di-alkylamino, a mono- or diaryl amino, alkoxy, aryloxy, haloalkyl, aralkyl, ester, nitrile, isonitrile, heteroary, alkoxycarbonyl, acylamino, alkoxycarbonylamino, aryloxycarbonylamino, sulfonylamino, sulfamoyl, carbamoyl, alkylthio, sulfinyl, ureido, phosphoramide, amercapto, sulfo, carboxyl, hydrzino, substituted silyl, or polymerizable, or any conjugate or combination thereof.

In one aspect, $R^a$ is selected from the group consisting hydrogen, deuterium, aryl, cycloalkyl, cycloalkenyl, heterocyclyl, heteroaryl, alkyl, alkenyl, alkynyl, halogen, hydroxyl, thiol, nitro, cyano, amino, a mono- or di-alkylamino, a mono- or diaryl amino, alkoxy, aryloxy, haloalkyl, aralkyl, ester, nitrile, isonitrile, heteroary, alkoxycarbonyl, acylamino, alkoxycarbonylamino, aryloxycarbonylamino, sulfonylamino, sulfamoyl, carbamoyl, alkylthio, sulfinyl, ureido, phosphoramide, amercapto, sulfo, carboxyl, hydrzino, substituted silyl, or polymerizable, or any conjugate or combination thereof.

In another aspect, $R^b$ is selected from the group consisting hydrogen, deuterium, aryl, cycloalkyl, cycloalkenyl, heterocyclyl, heteroaryl, alkyl, alkenyl, alkynyl, halogen, hydroxyl, thiol, nitro, cyano, amino, a mono- or di-alkylamino, a mono- or diaryl amino, alkoxy, aryloxy, haloalkyl, aralkyl, ester, nitrile, isonitrile, heteroary, alkoxycarbonyl, acylamino, alkoxycarbonylamino, aryloxycarbonylamino, sulfonylamino, sulfamoyl, carbamoyl, alkylthio, sulfinyl, ureido, phosphoramide, amercapto, sulfo, carboxyl, hydrzino, substituted silyl, or polymerizable, or any conjugate or combination thereof.

In one aspect, $R^c$ is selected from the group consisting hydrogen, deuterium aryl, cycloalkyl, cycloalkenyl, heterocyclyl, heteroaryl, alkyl, alkenyl, alkynyl, halogen, hydroxyl, thiol, nitro, cyano, amino, a mono- or di-alkylamino, a mono- or diaryl amino, alkoxy, aryloxy, haloalkyl, aralkyl, ester, nitrile, isonitrile, heteroary, alkoxycarbonyl, acylamino, alkoxycarbonylamino, aryloxycarbonylamino, sulfonylamino, sulfamoyl, carbamoyl, alkylthio, sulfinyl, ureido, phosphoramide, amercapto, sulfo, carboxyl, hydrzino, substituted silyl, or polymerizable, or any conjugate or combination thereof.

In another aspect, $R^d$ is selected from the group consisting hydrogen, deuterium, aryl, cycloalkyl, cycloalkenyl, heterocyclyl, heteroaryl, alkyl, alkenyl, alkynyl, halogen, hydroxyl, thiol, nitro, cyano, amino, a mono- or di-alkylamino, a mono- or diaryl amino, alkoxy, aryloxy, haloalkyl, aralkyl, ester, nitrile, isonitrile, heteroary, alkoxycarbonyl, acylamino, alkoxycarbonylamino, aryloxycarbonylamino, sulfonylamino, sulfamoyl, carbamoyl, alkylthio, sulfinyl, ureido, phosphoramide, amercapto, sulfo, carboxyl, hydrzino, substituted silyl, or polymerizable, or any conjugate or combination thereof.

In one aspect, for any of the platinum complexes illustrated in this disclosure, can comprise one or more of the following structures. In another aspect, they can also comprise other structures or portions thereof not specifically recited herein, and the present invention is not intended to be limited to those structures or portions thereof specifically recited.

F. Exemplary Compounds

Compound 1

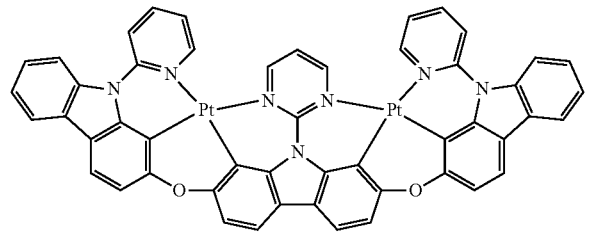

Compound 2

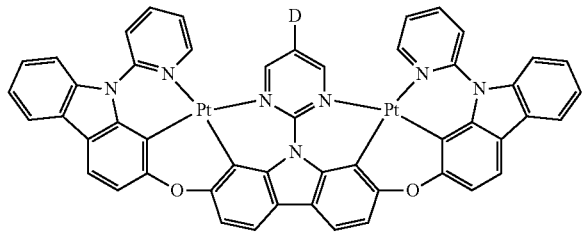

Compound 3

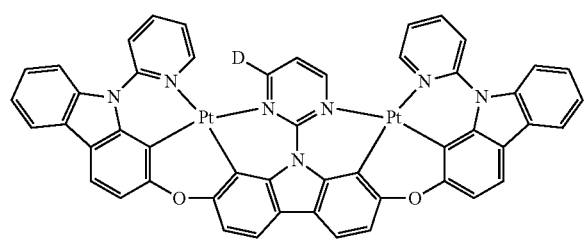

Compound 4

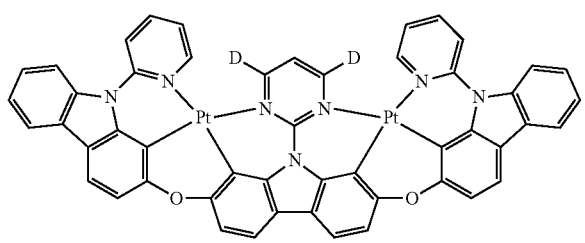

Compound 5

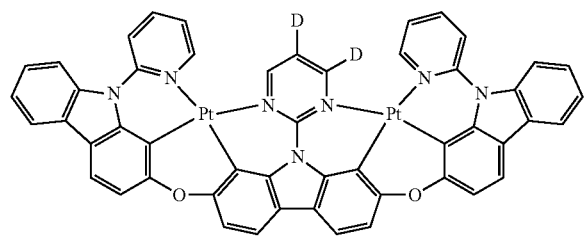

Compound 6

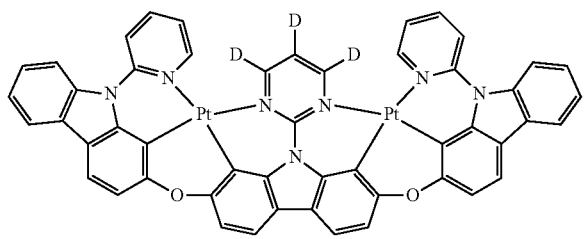

Compound 7

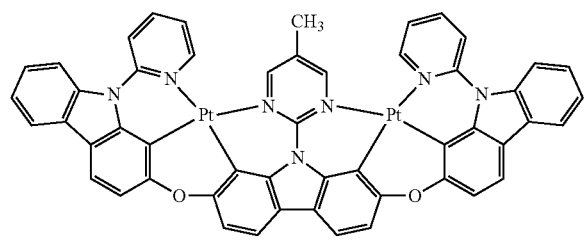

Compound 8

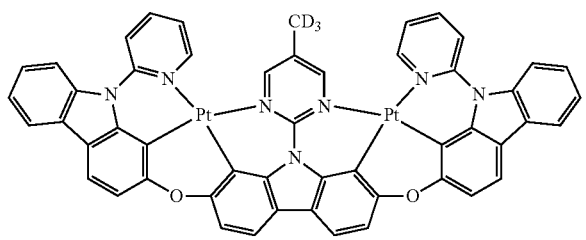

Compound 9

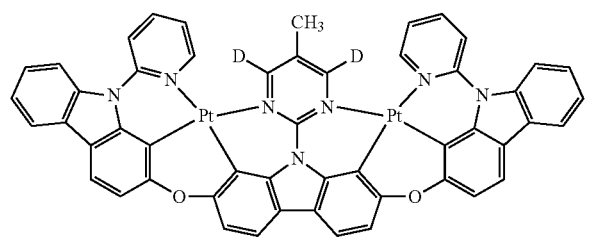

Compound 10

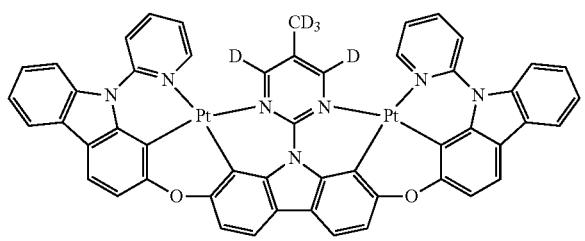

-continued
Compound 11
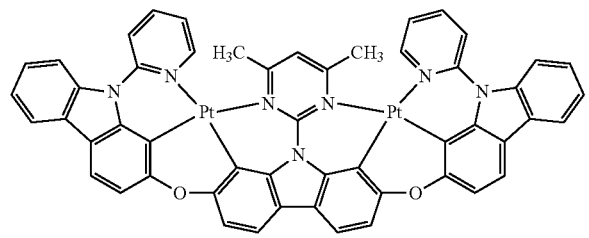
Compound 12
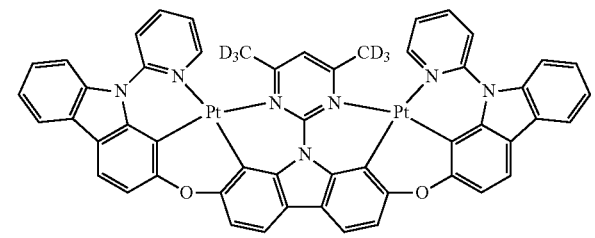
Compound 13
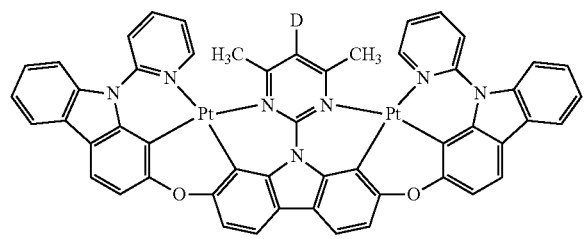
Compound 14
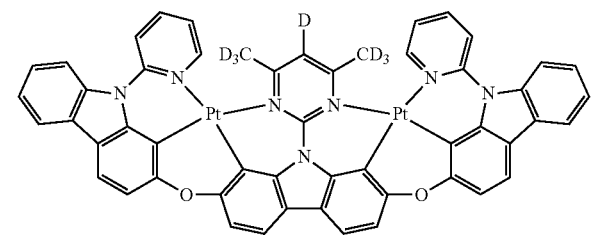
Compound 15
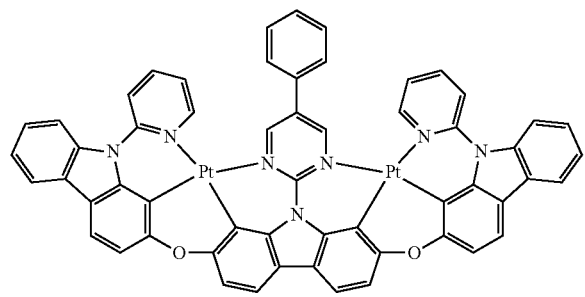
Compound 16
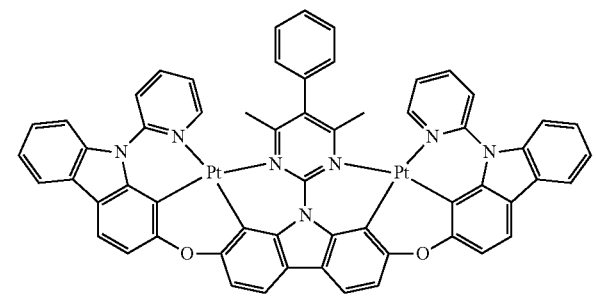
Compound 17
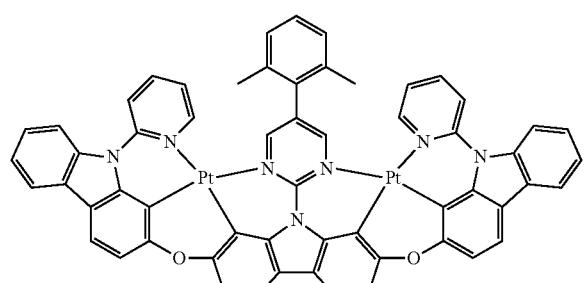
Compound 18
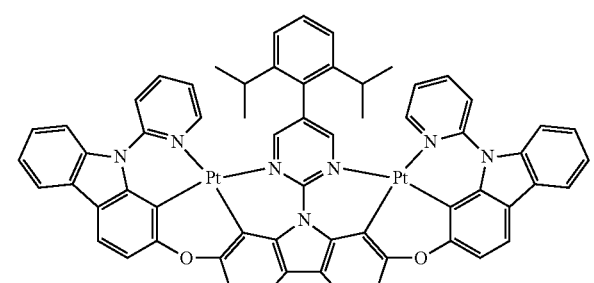
Compound 19
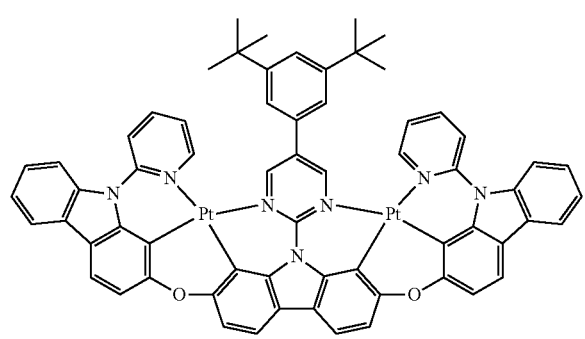
Compound 20
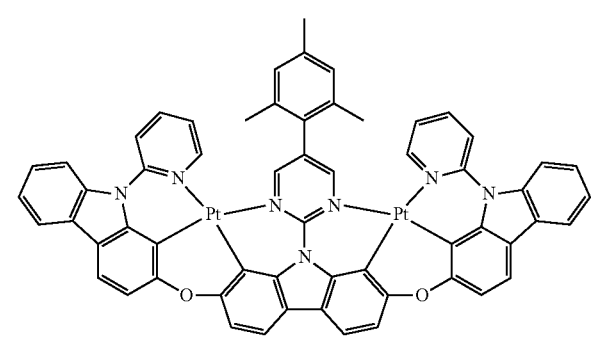

-continued
Compound 21
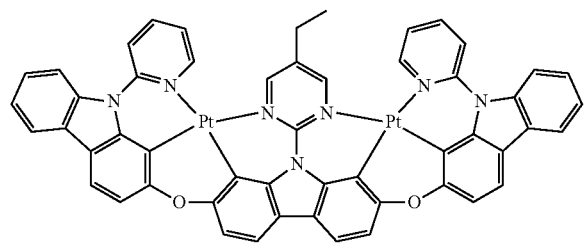
Compound 22
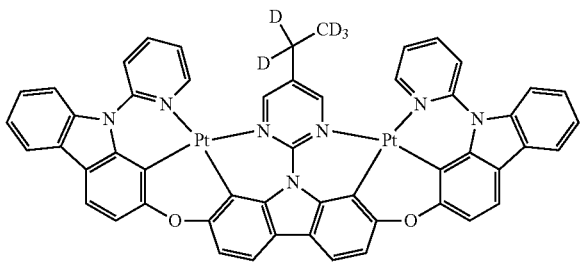
Compound 23
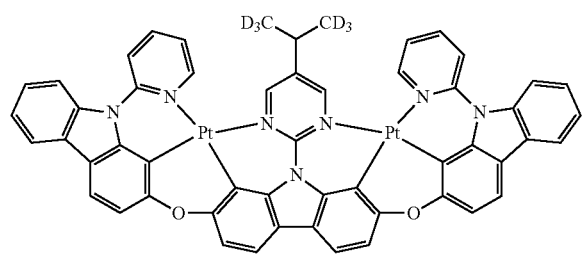
Compound 24
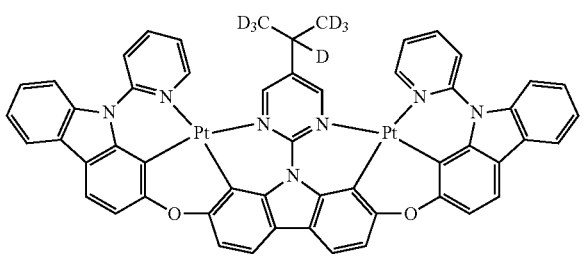
Compound 25
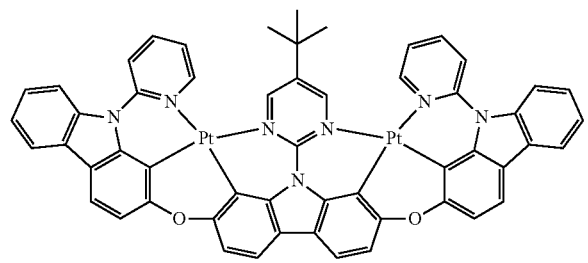
Compound 26
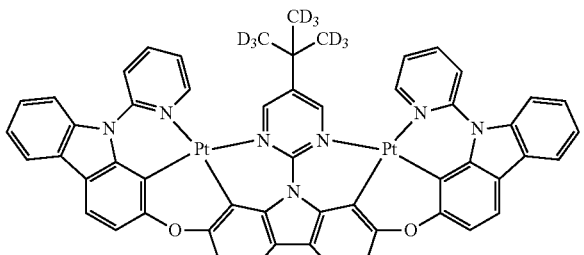
Compound 27
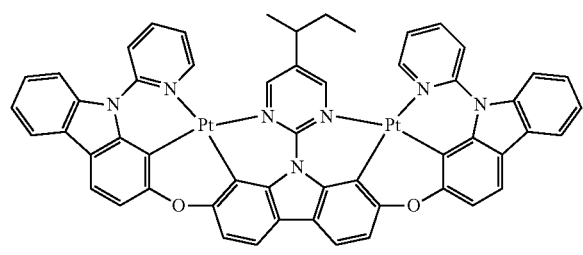
Compound 28
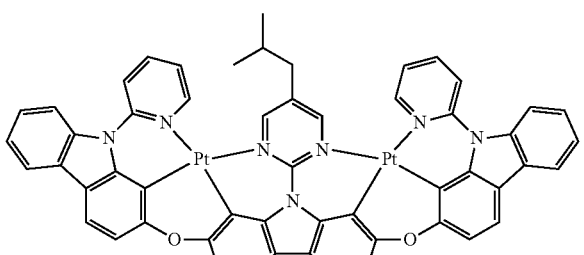
Compound 29
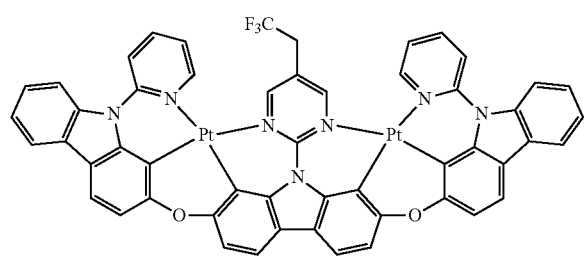
Compound 30
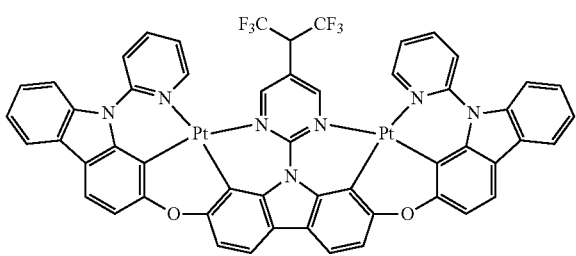

-continued
Compound 31
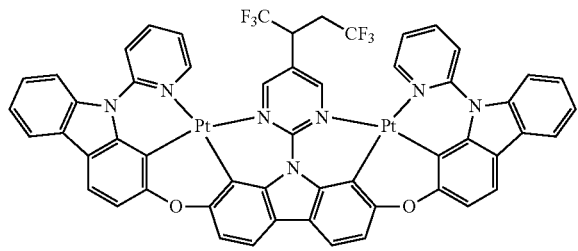
Compound 32
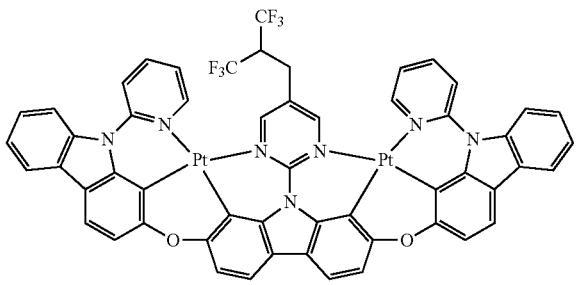
Compound 33
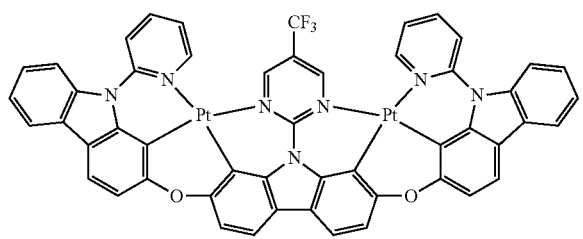
Compound 34
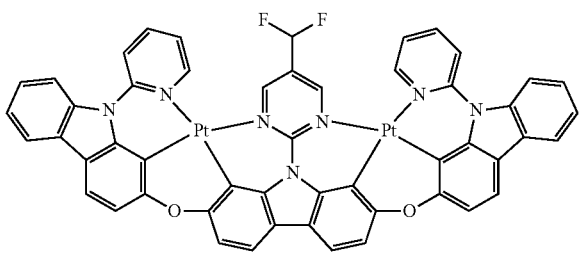
Compound 35
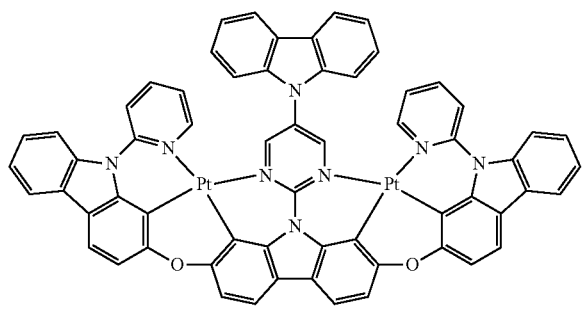
Compound 36
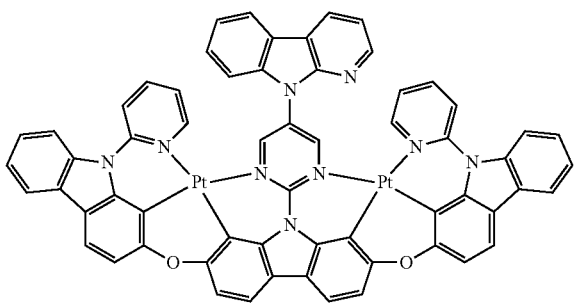
Compound 37
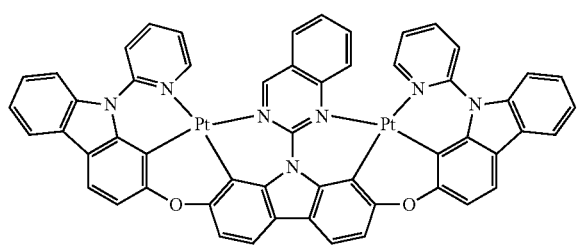
Compound 38
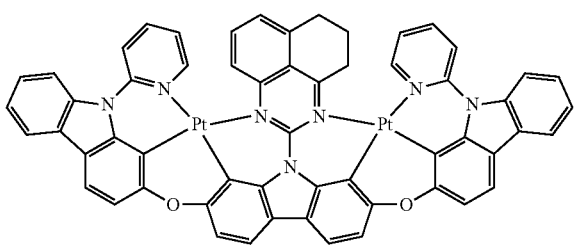
Compound 39
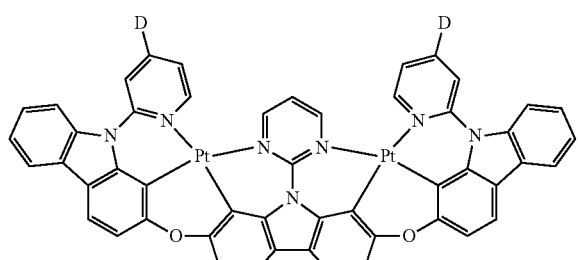
Compound 40
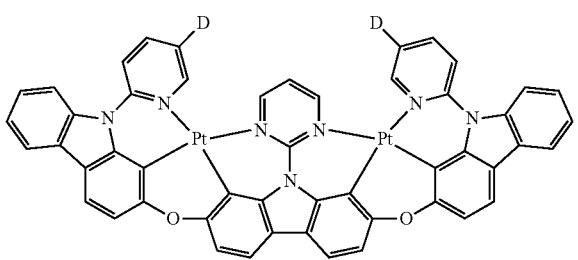

-continued
Compound 41
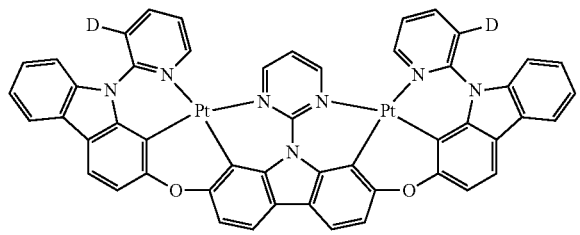
Compound 42
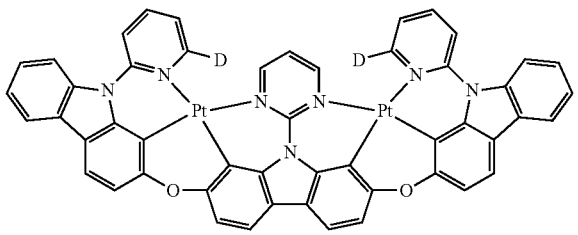
Compound 43
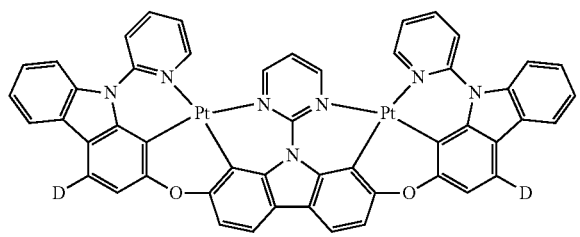
Compound 44
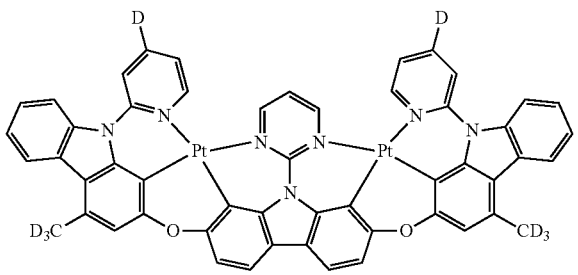
Compound 45
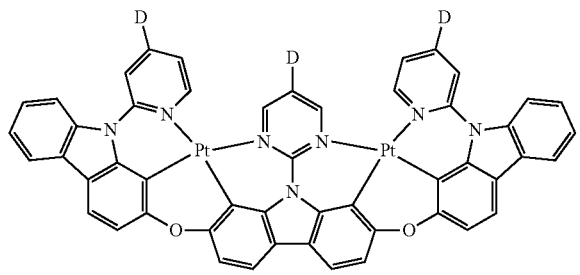
Compound 46
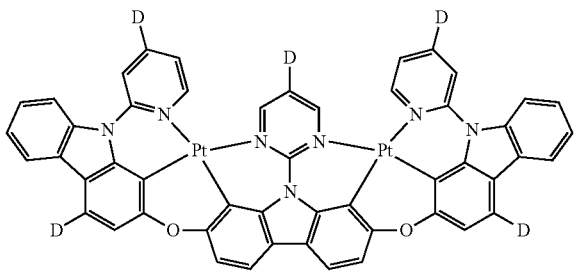
Compound 47
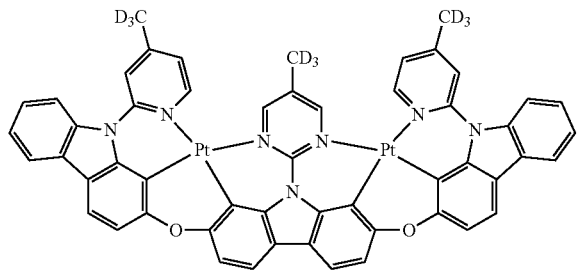
Compound 48
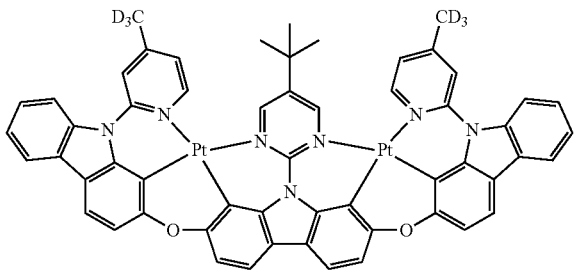
Compound 49
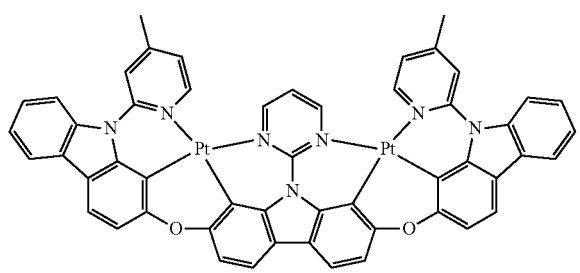
Compound 50
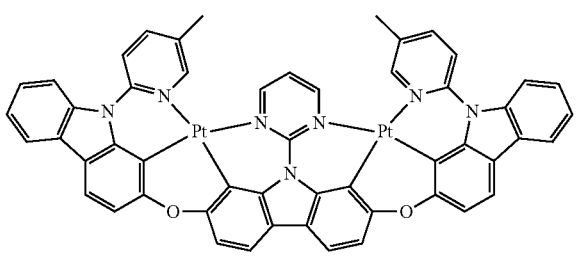

-continued
Compound 51
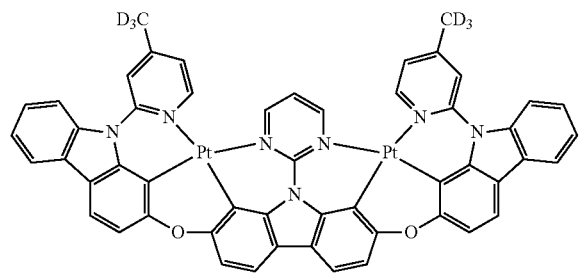
Compound 52
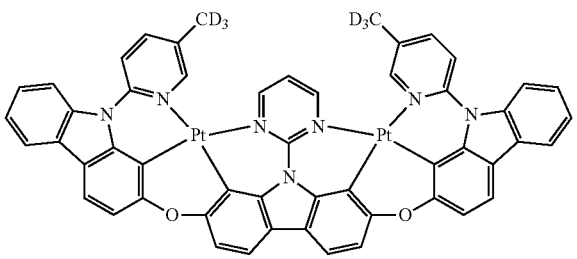
Compound 53
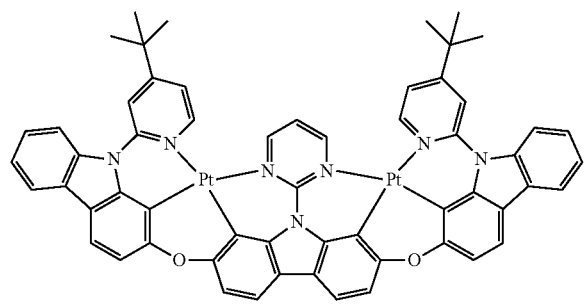
Compound 54
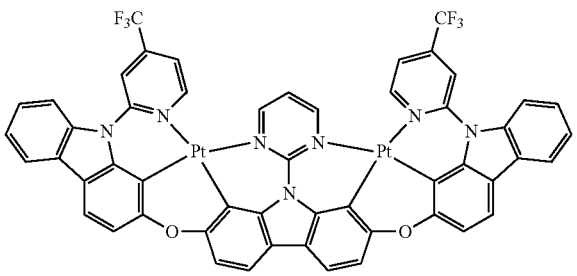
Compound 55
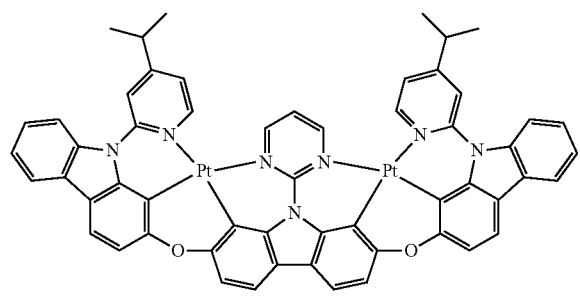
Compound 56
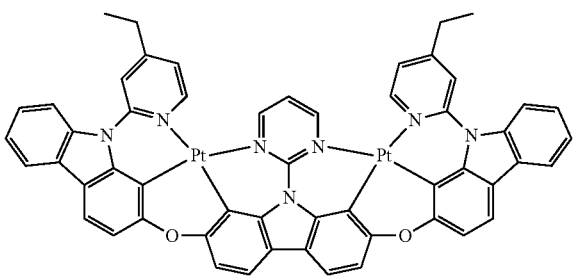
Compound 57
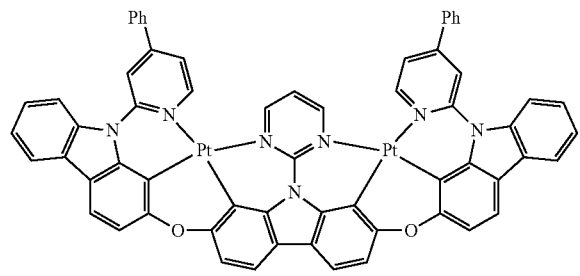
Compound 58
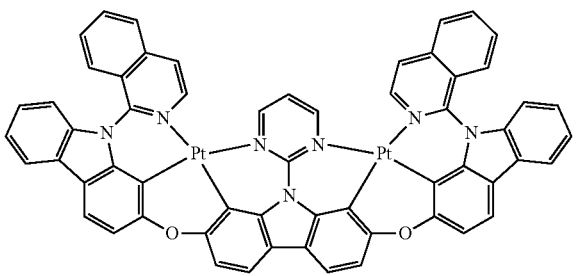
Compound 59
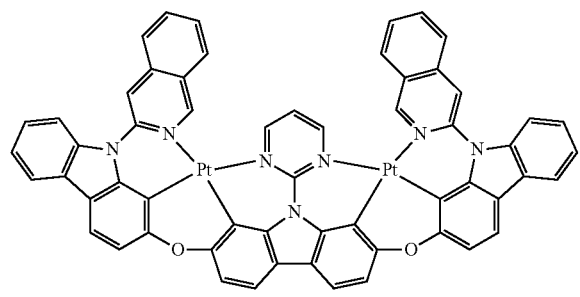
Compound 60
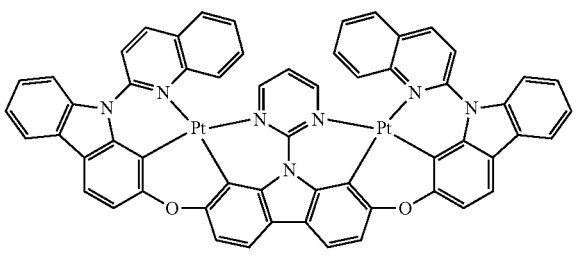

-continued
Compound 61
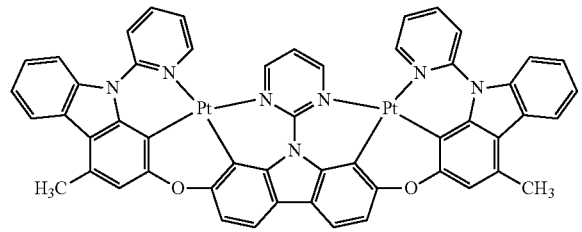
Compound 62
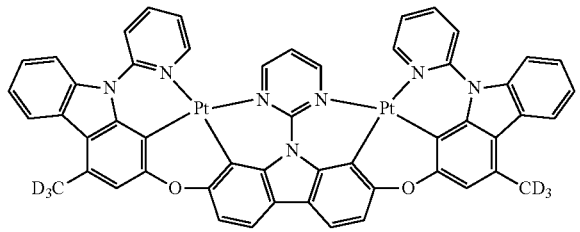
Compound 63
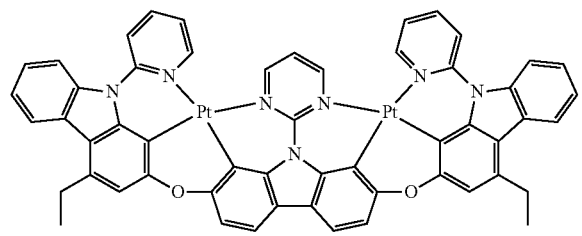
Compound 64
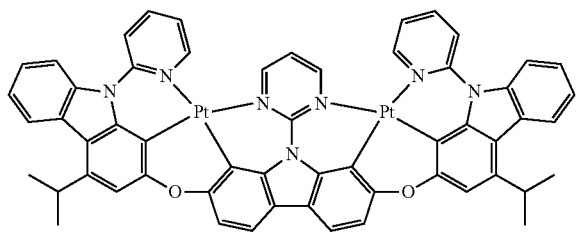
Compound 65
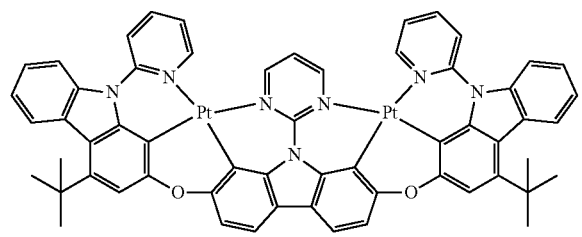
Compound 66
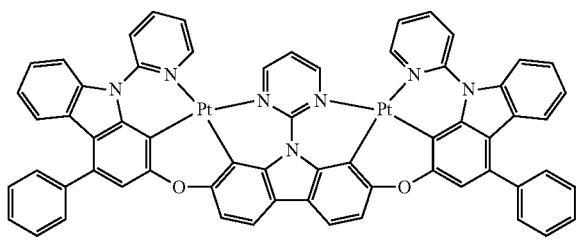
Compound 67
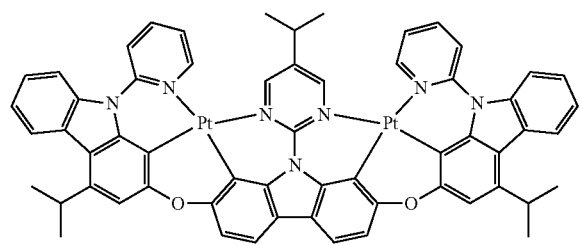
Compound 68
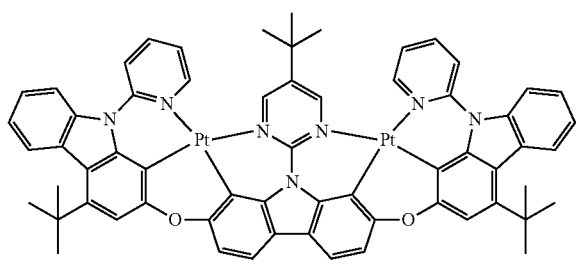
Compound 69
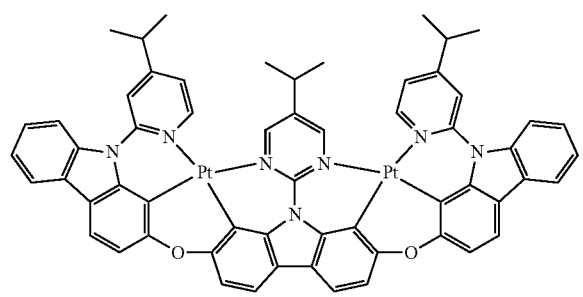
Compound 70
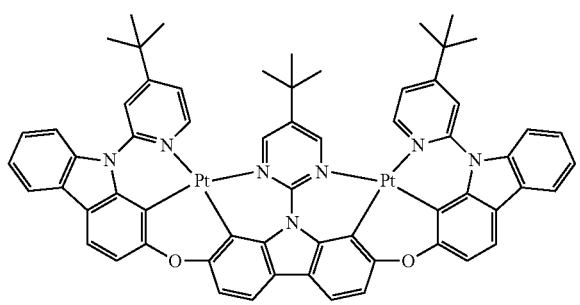

-continued
Compound 71
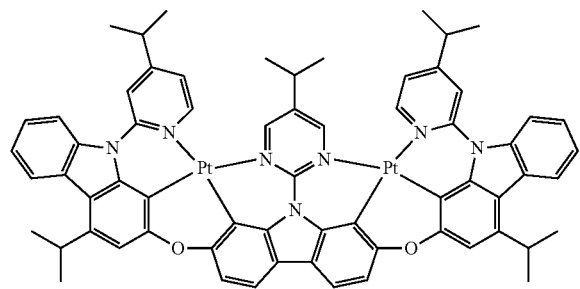
Compound 72
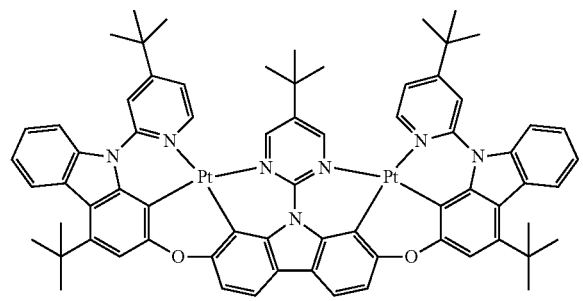
Compound 73
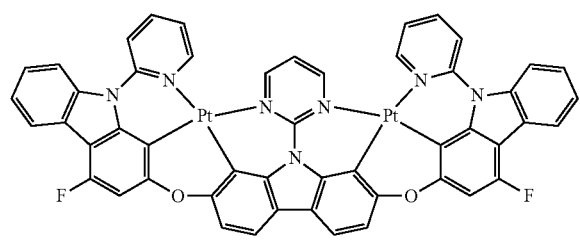
Compound 74
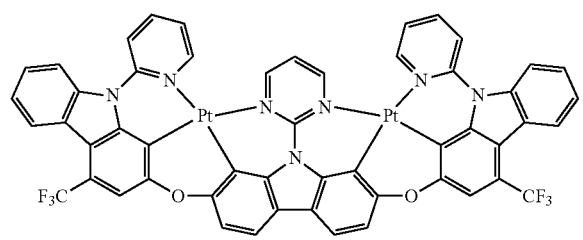
Compound 75
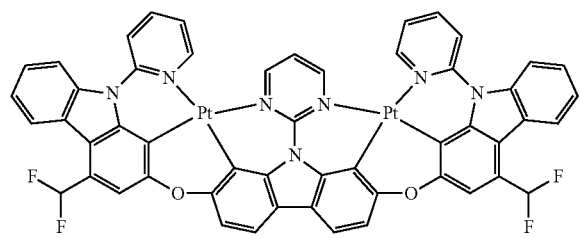
Compound 76
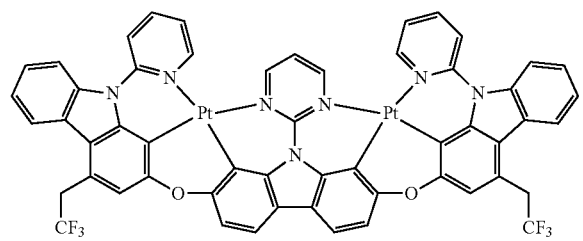
Compound 77
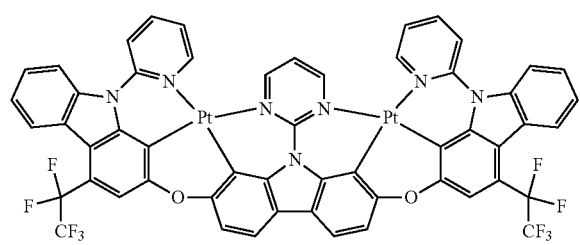
Compound 78
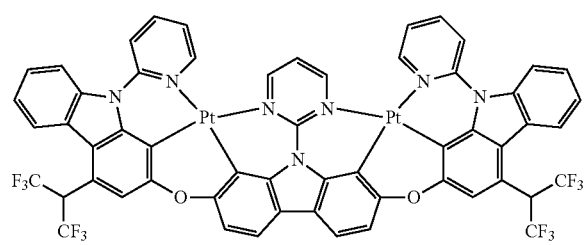
Compound 79
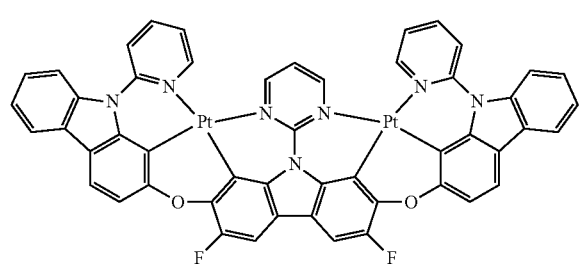
Compound 80
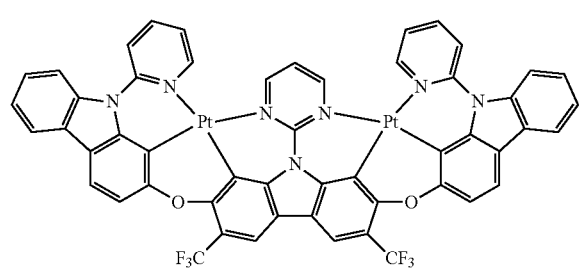

-continued
Compound 81
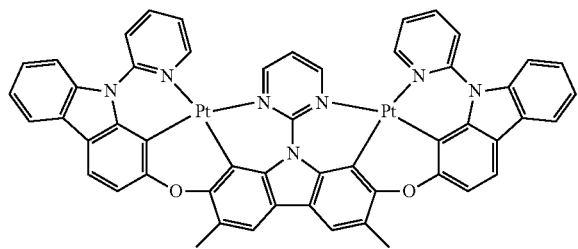
Compound 82
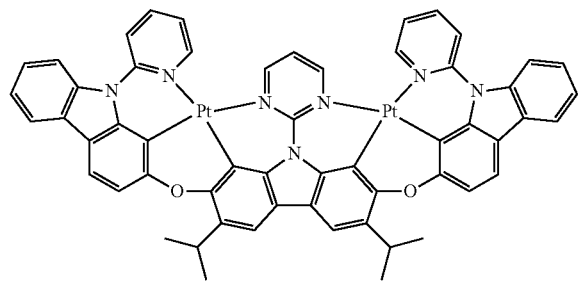
Compound 83
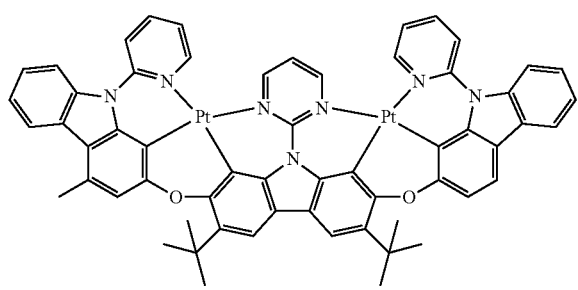
Compound 84
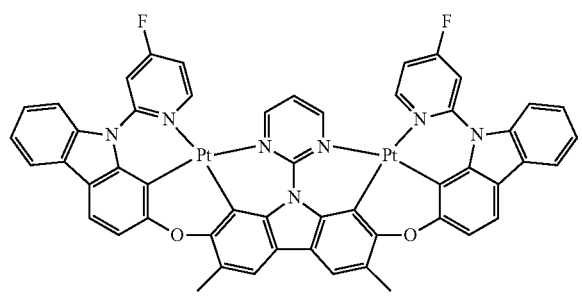
Compound 85
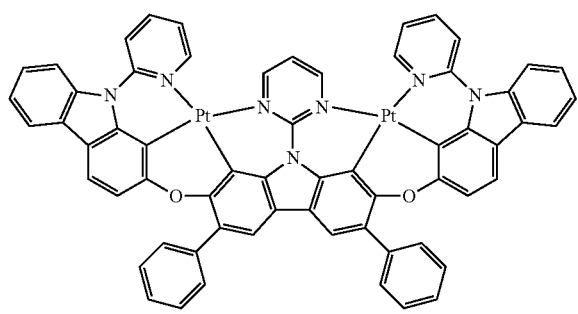
Compound 86
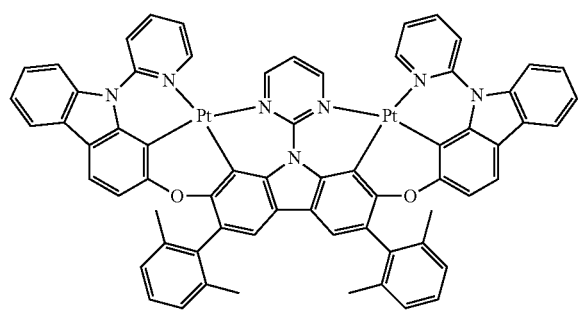
Compound 87
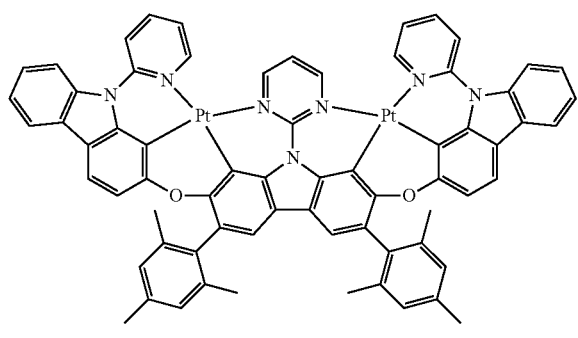
Compound 88
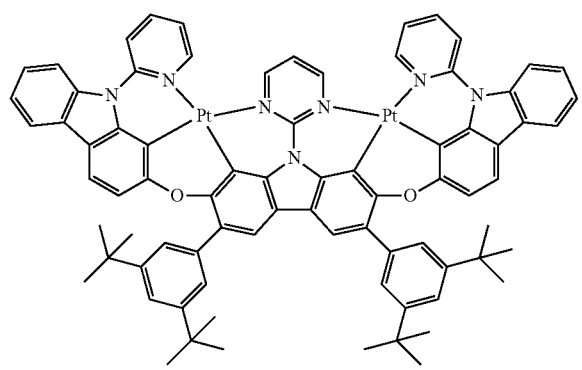

-continued
Compound 89
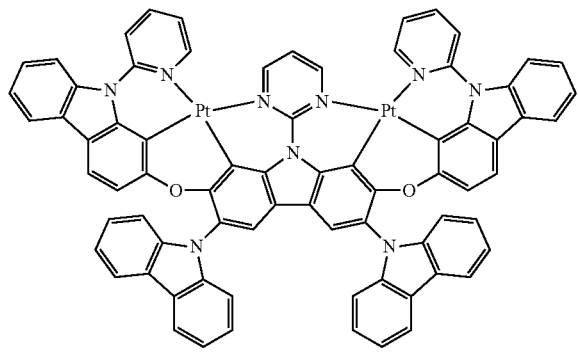
Compound 90
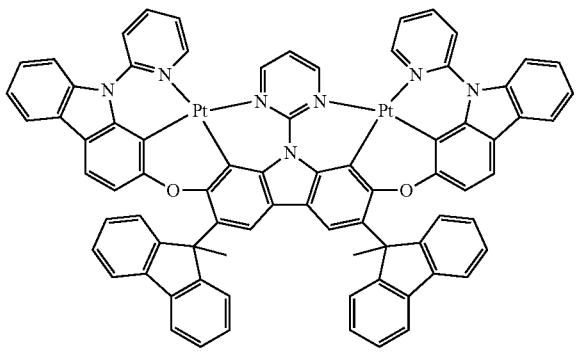
Compound 91
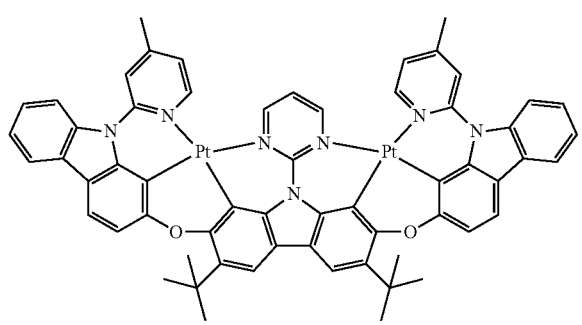
Compound 92
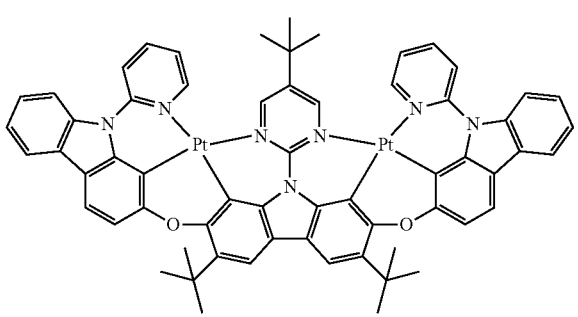
Compound 93
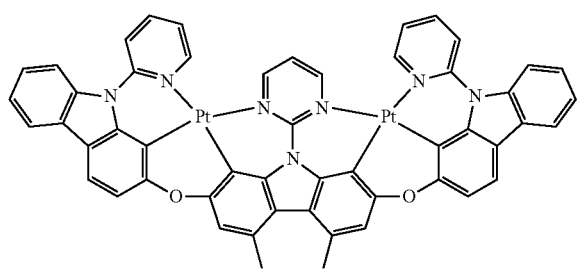
Compound 94
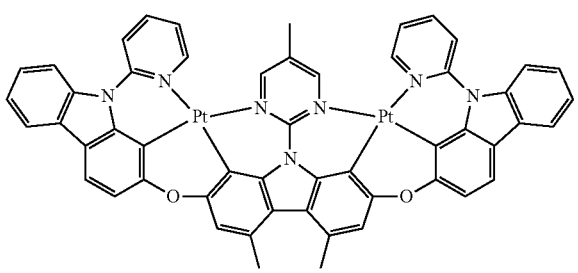
Compound 95
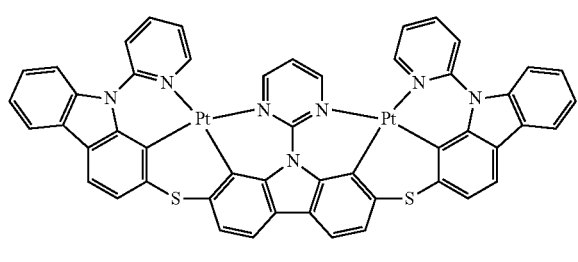
Compound 96
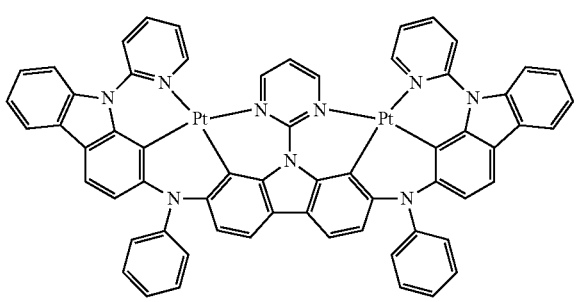
Compound 97
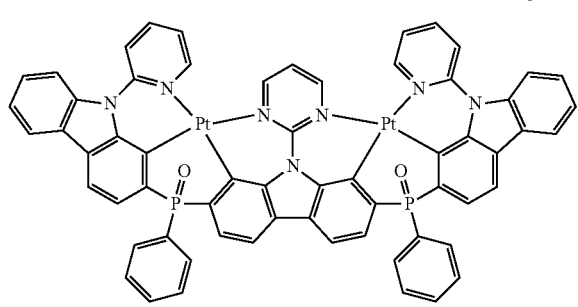
Compound 98
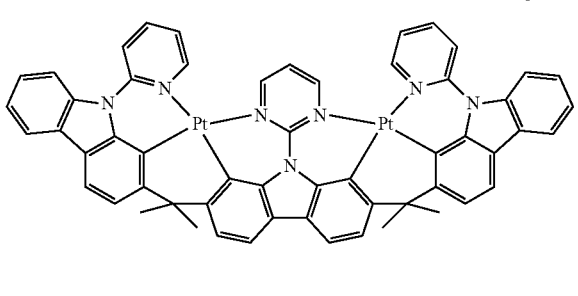

-continued
Compound 99
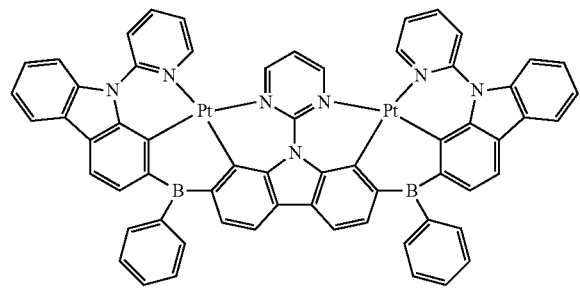
Compound 100
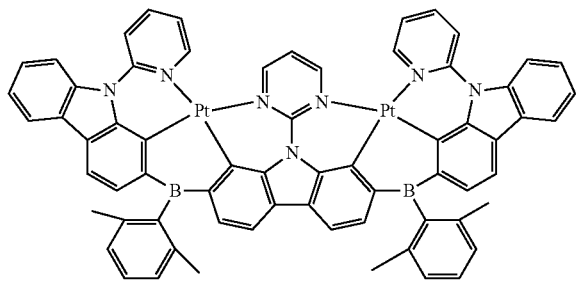
Compound 101
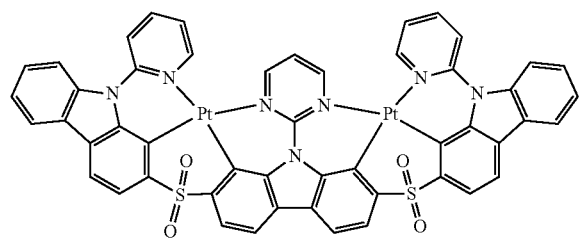
Compound 102
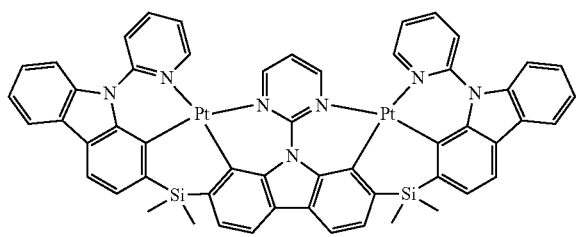
Compound 103
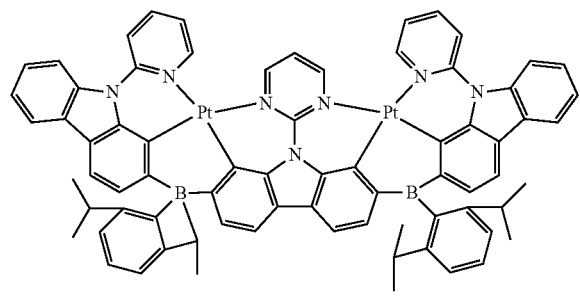
Compound 104
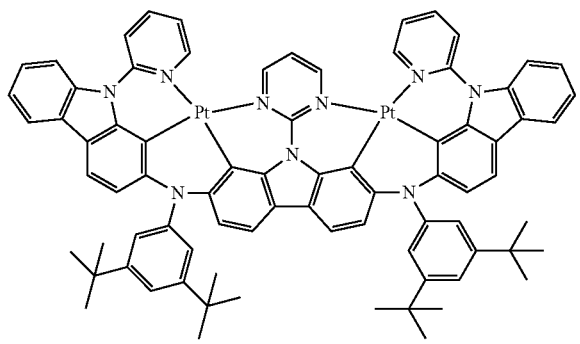
Compound 105
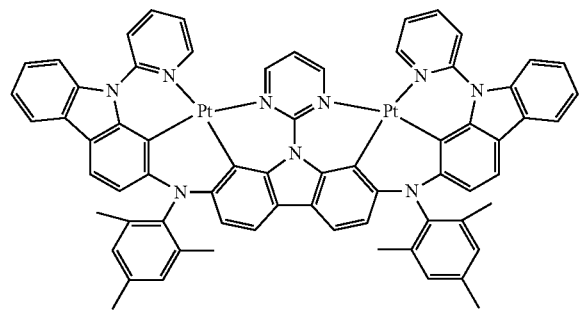
Compound 106
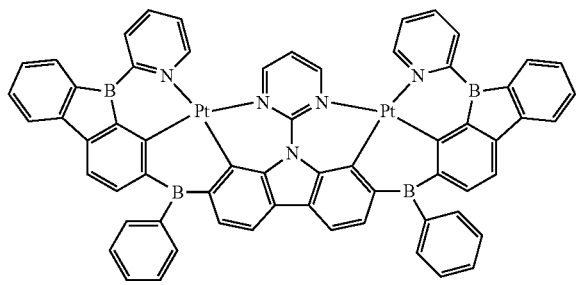
Compound 107
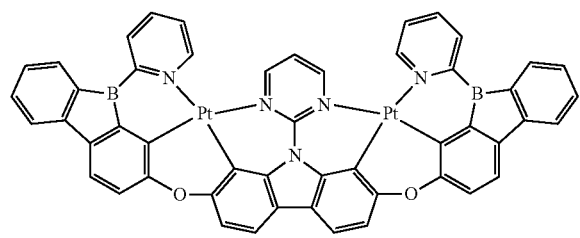
Compound 108
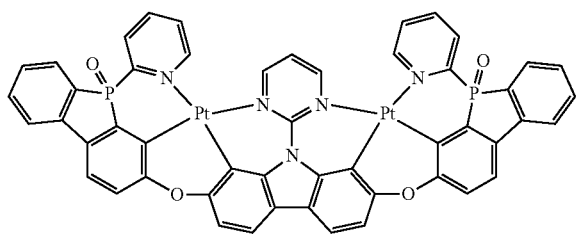

-continued
Compound 109
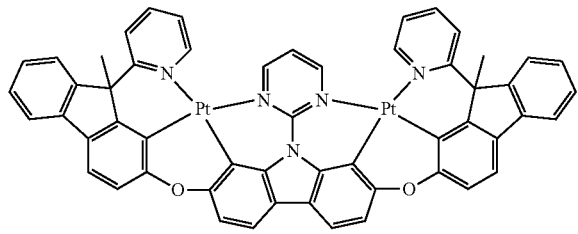
Compound 110
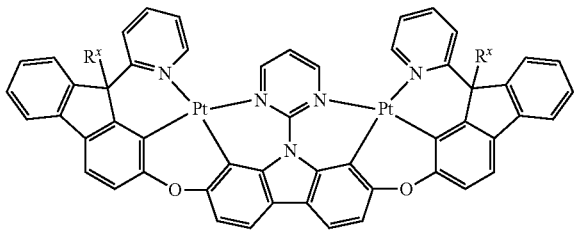
Compound 111
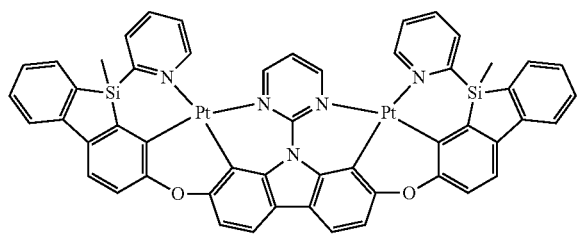
Compound 112
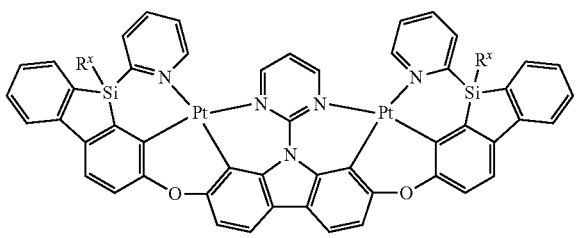
Compound 113
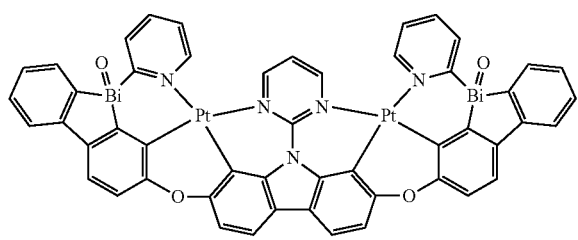
Compound 114
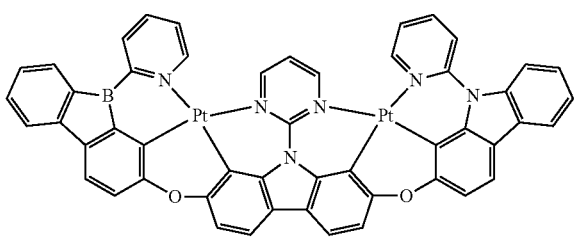
Compound 115
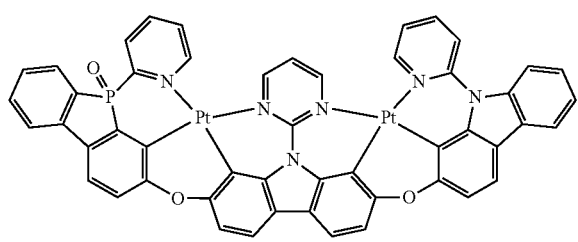
Compound 116
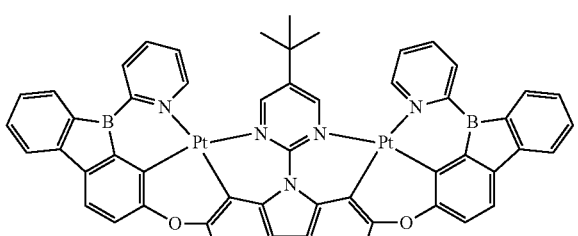
Compound 117
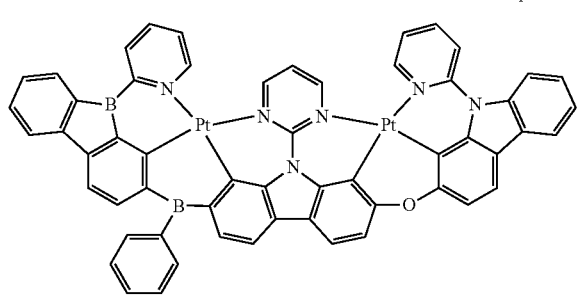
Compound 118
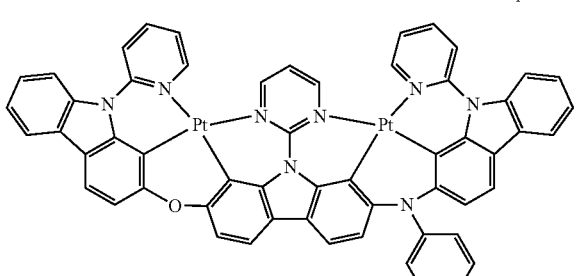
Compound 119
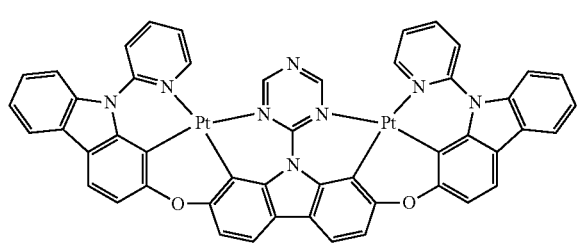
Compound 120
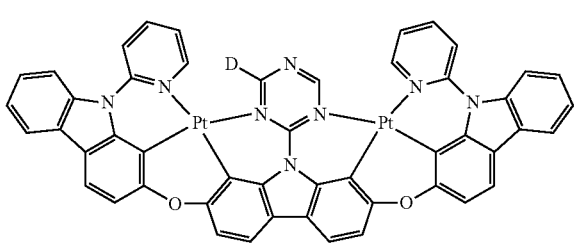

-continued
Compound 121
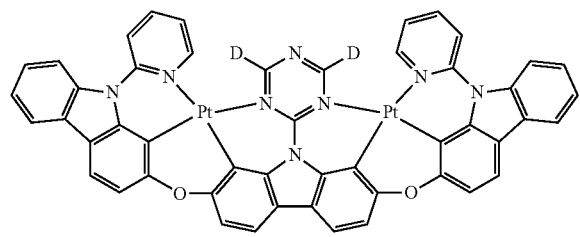
Compound 122
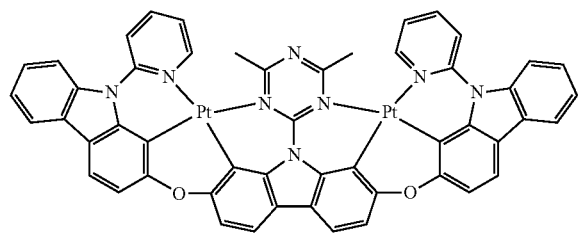
Compound 123
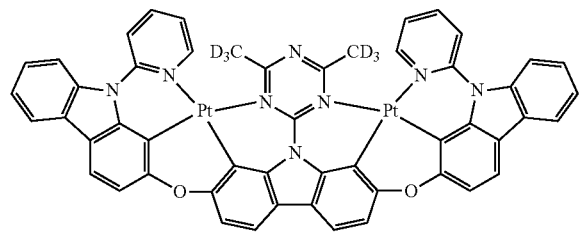
Compound 124
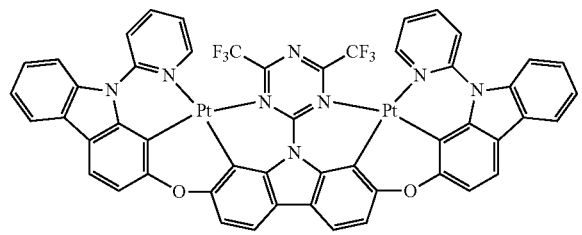
Compound 125
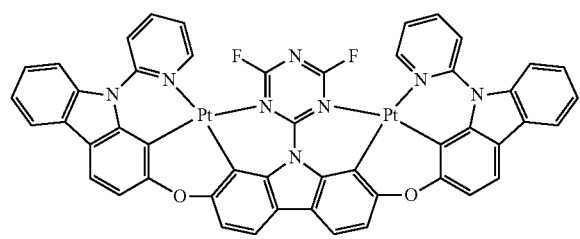
Compound 126
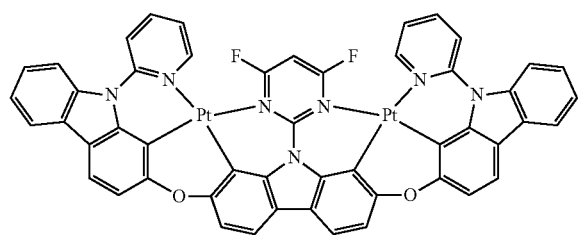
Compound 127
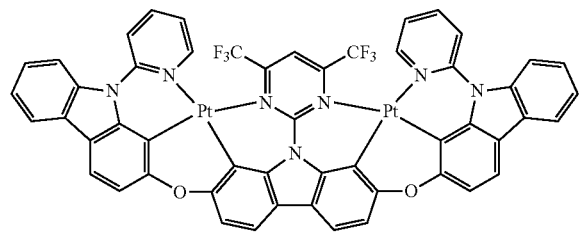
Compound 128
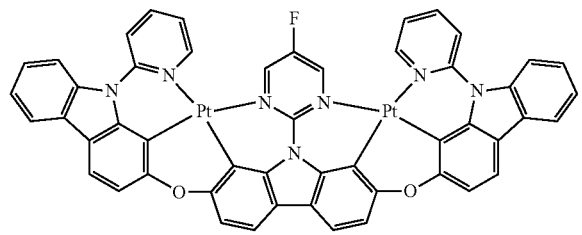
Compound 129
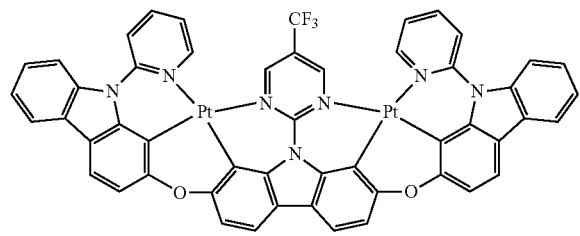
Compound 130
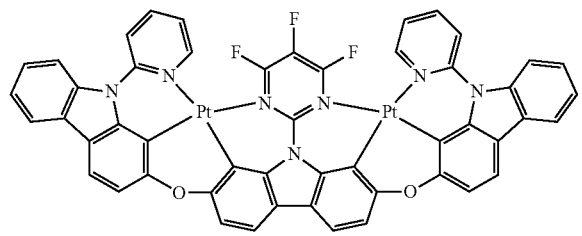
Compound 131
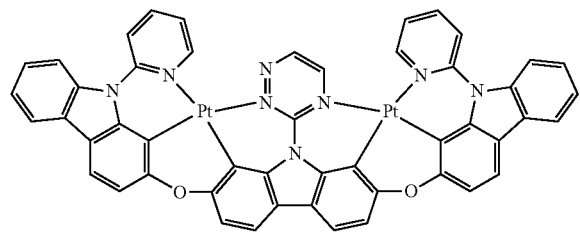
Compound 132
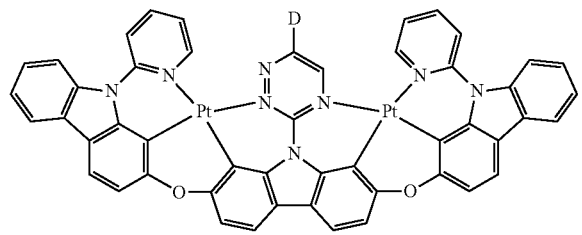

Compound 133
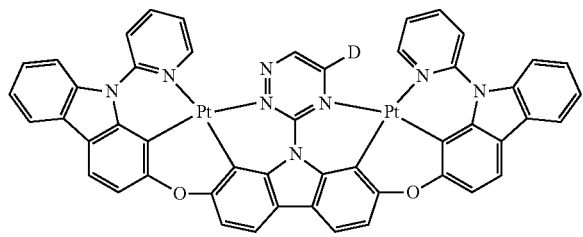
Compound 134
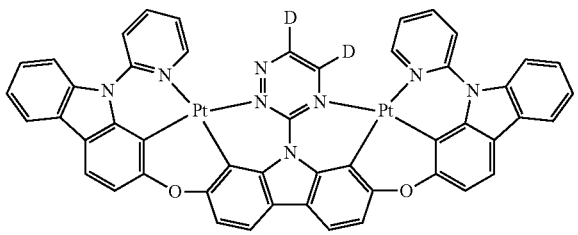
Compound 135
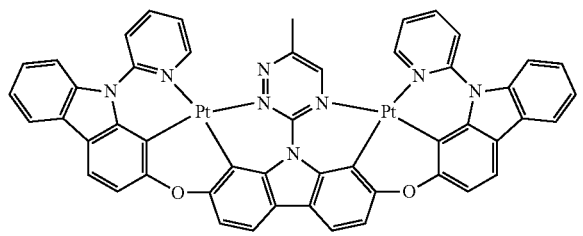
Compound 136
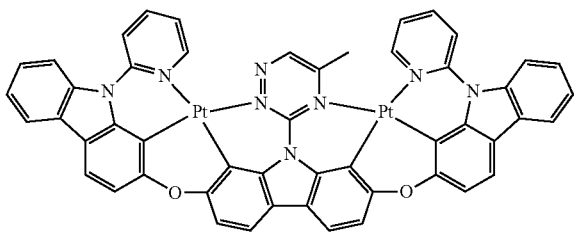
Compound 137
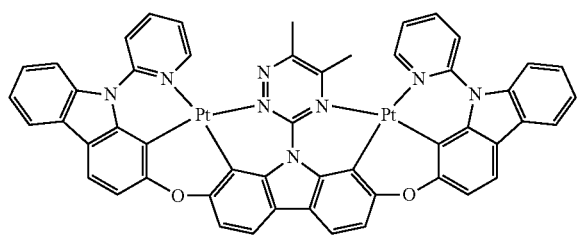
Compound 138
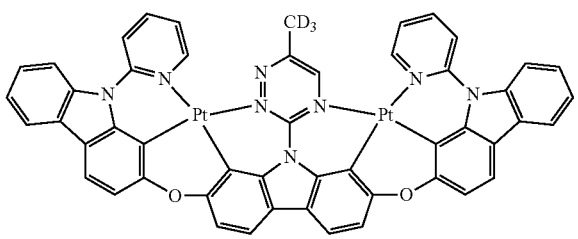
Compound 139
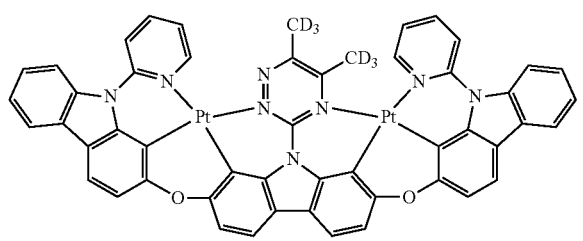
Compound 140
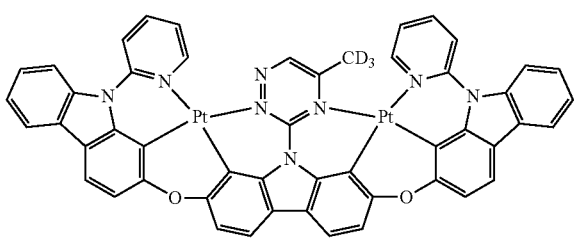
Compound 141
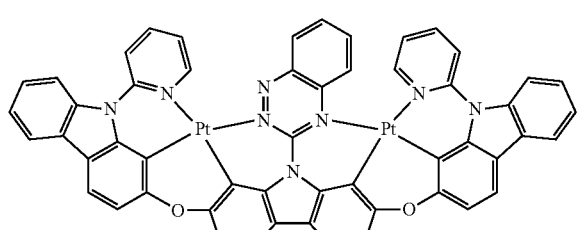
Compound 142
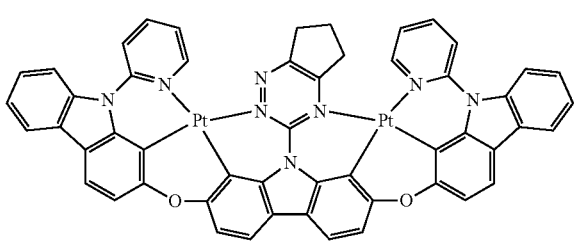
Compound 143
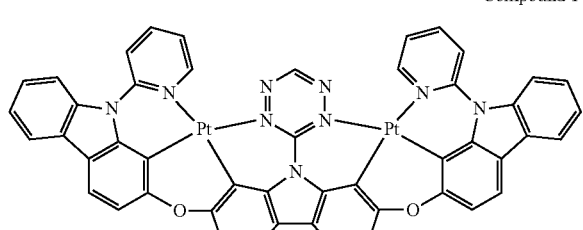
Compound 144
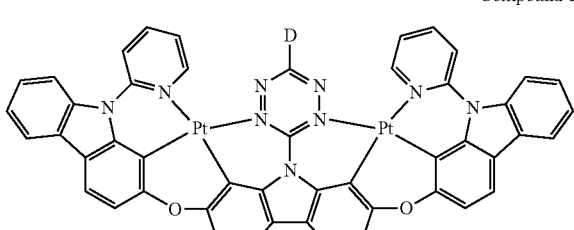

-continued
Compound 145
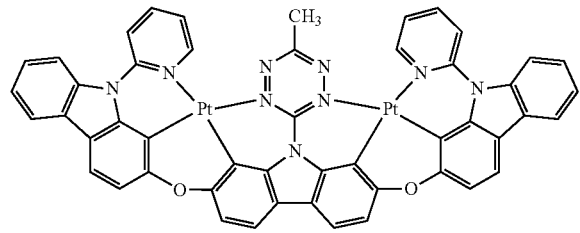
Compound 146
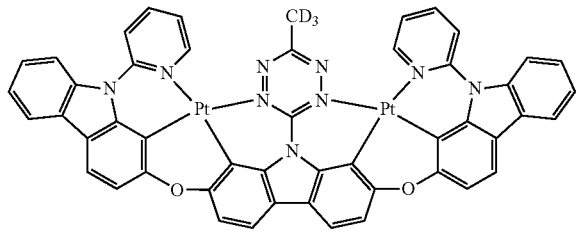
Compound 147
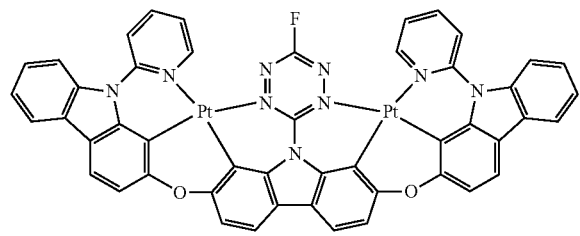
Compound 148
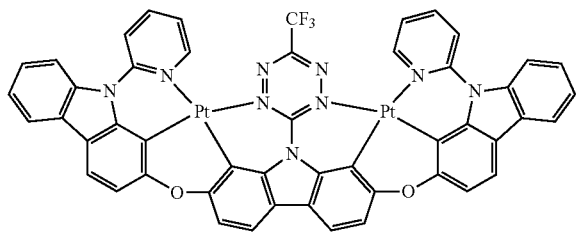
Compound 149
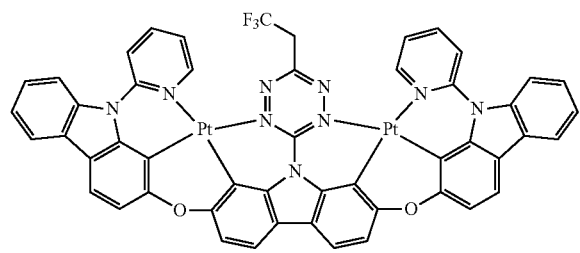
Compound 150
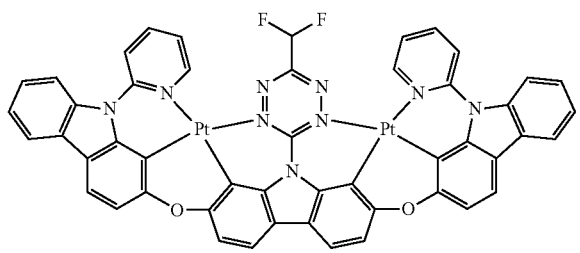
Compound 151
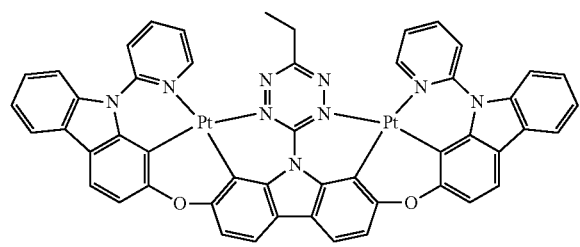
Compound 152
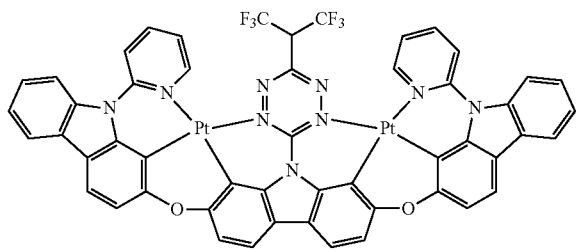
Compound 153
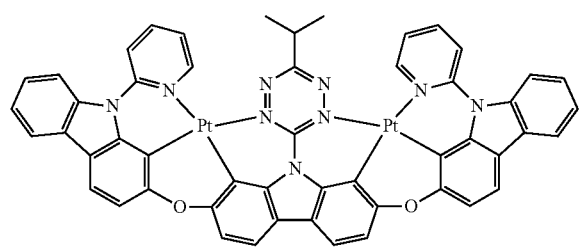
Compound 154
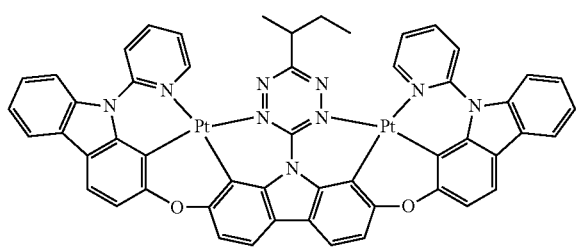
Compound 155
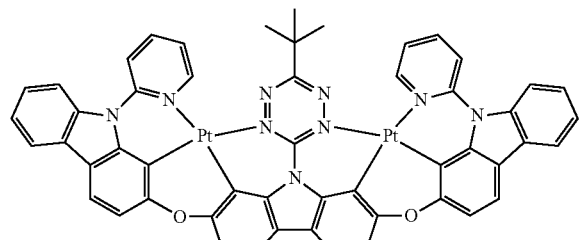
Compound 156
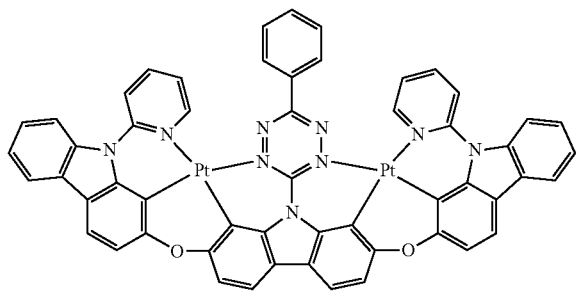

-continued
Compound 157
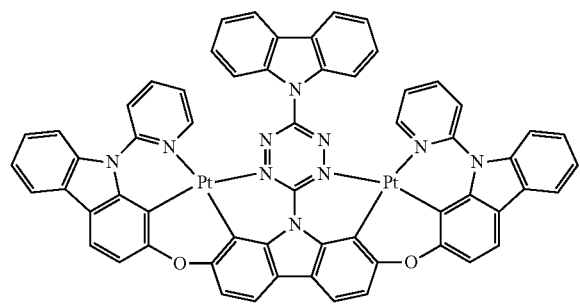
Compound 158
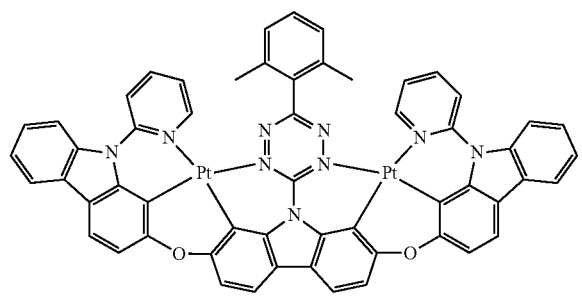
Compound 159
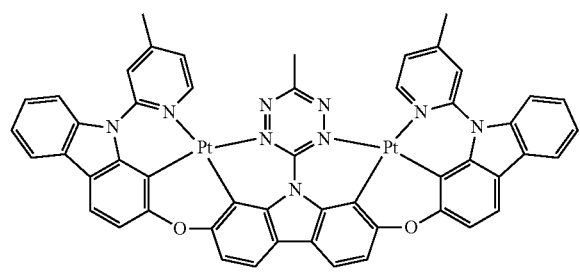
Compound 160
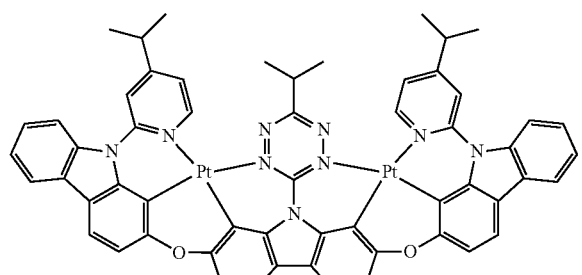
Compound 161
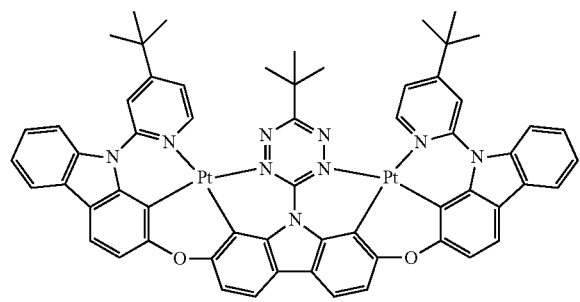
Compound 162
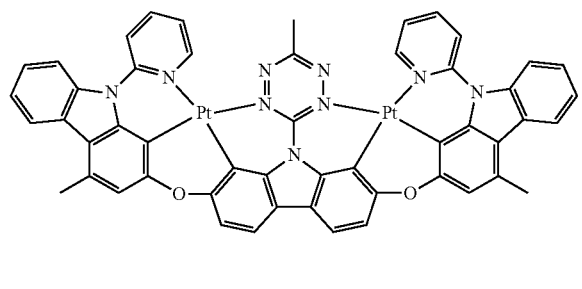
Compound 163
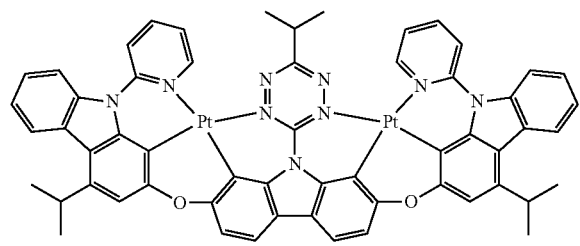
Compound 164
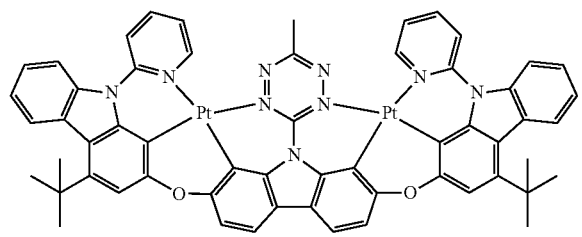
Compound 165
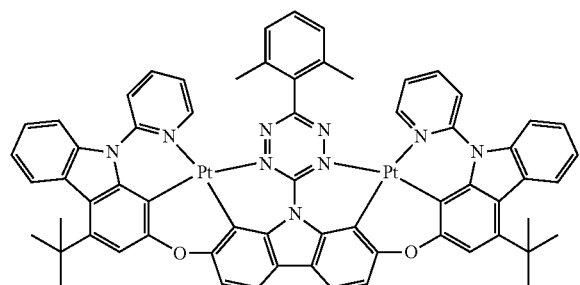
Compound 166
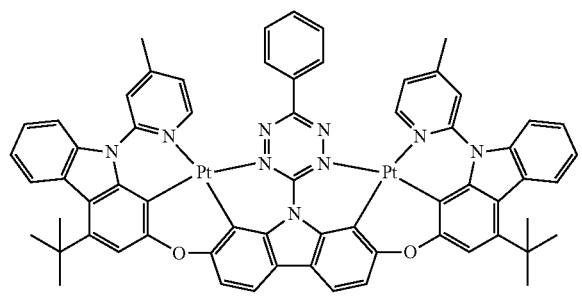

-continued
Compound 167
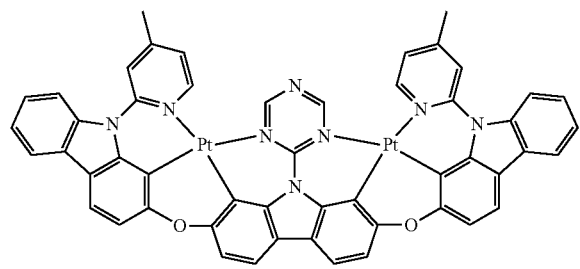
Compound 168
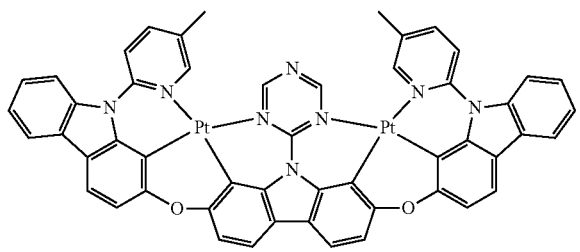
Compound 169
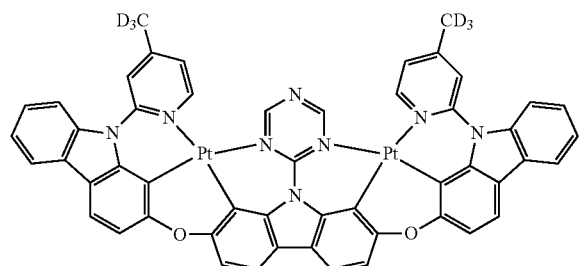
Compound 170
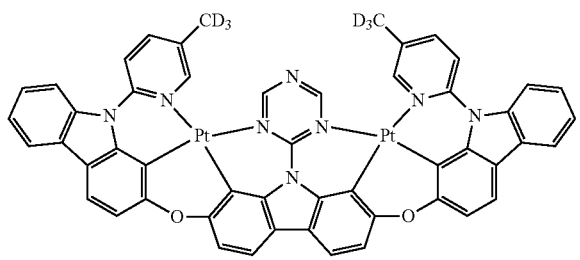
Compound 171
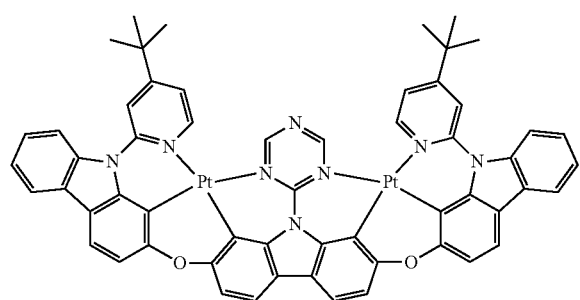
Compound 172
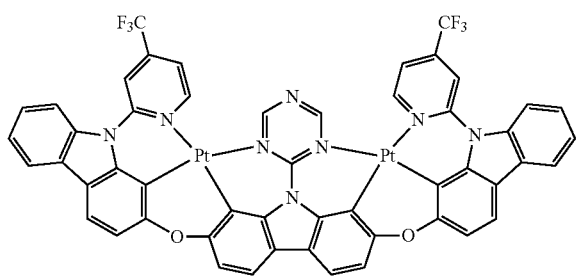
Compound 173
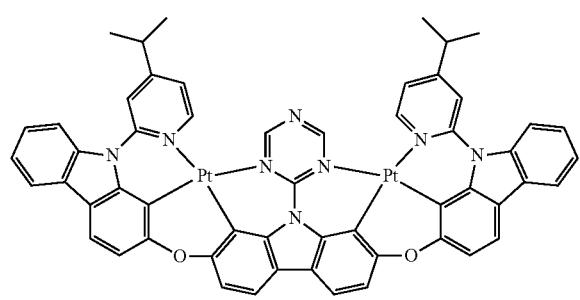
Compound 174
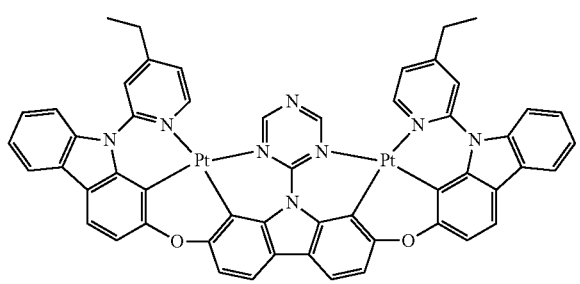
Compound 175
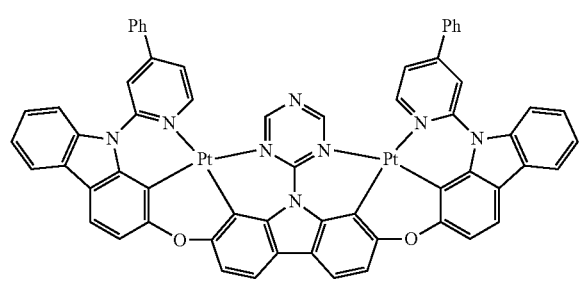
Compound 176
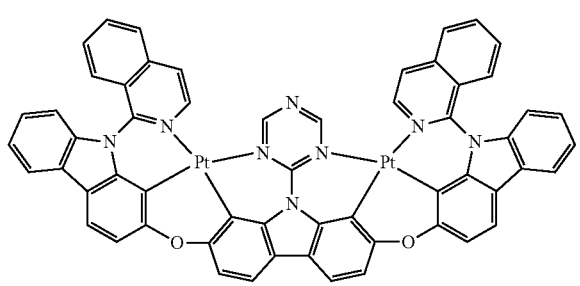

-continued
Compound 177
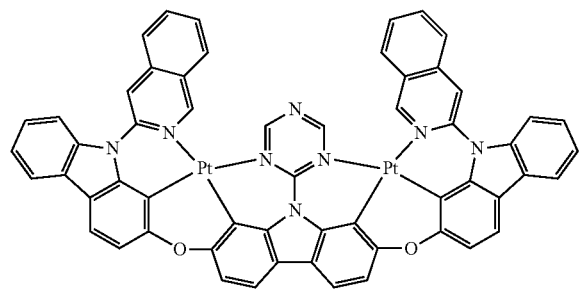
Compound 178
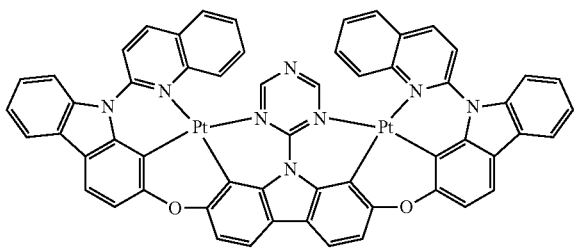
Compound 179
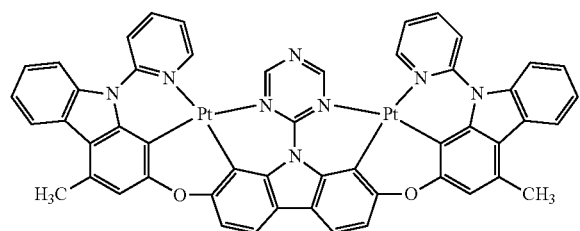
Compound 180
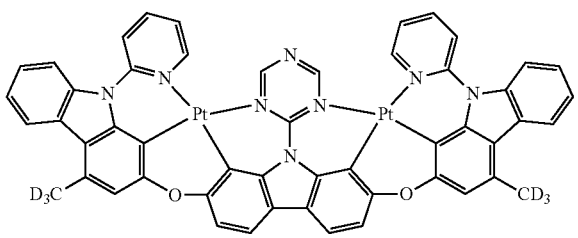
Compound 181
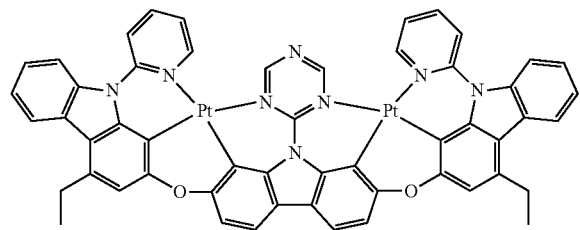
Compound 182
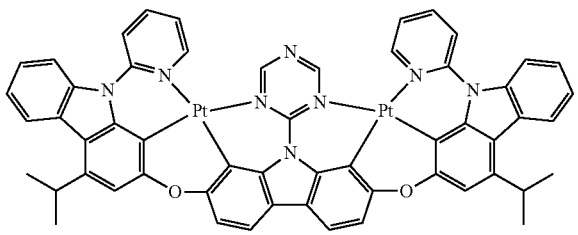
Compound 183
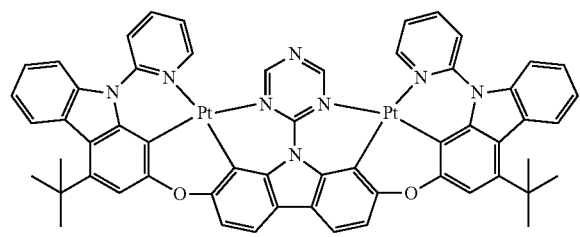
Compound 184
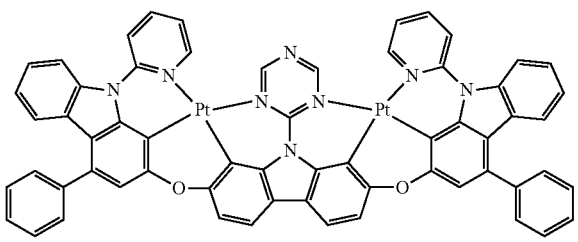
Compound 185
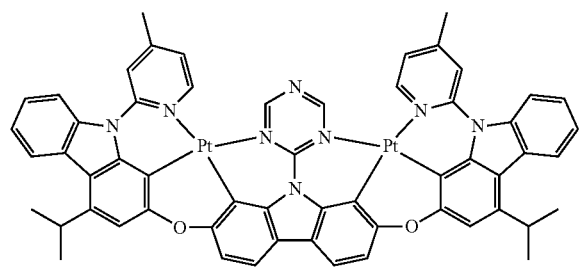
Compound 186
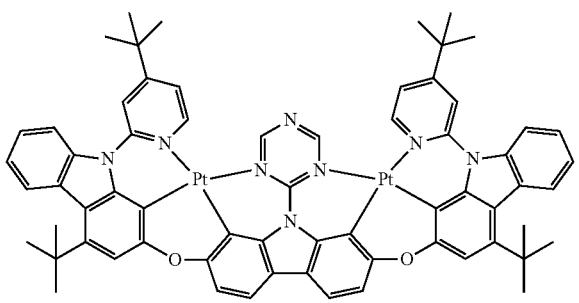

-continued
Compound 187
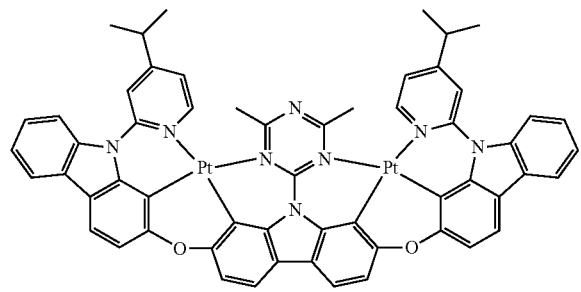
Compound 188
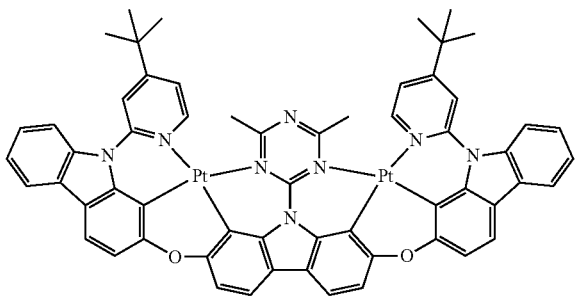
Compound 189
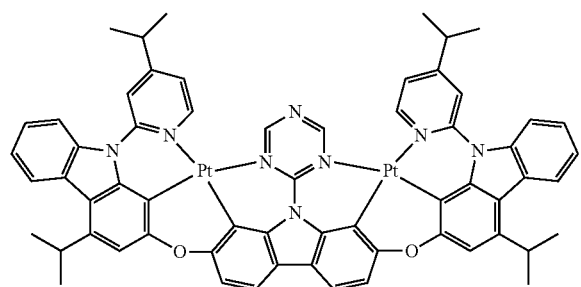
Compound 190
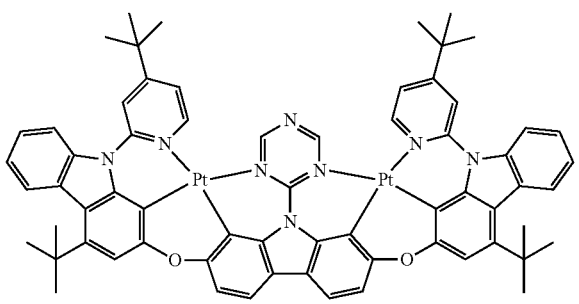
Compound 191
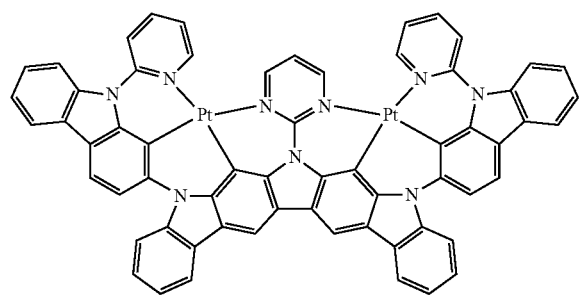
Compound 192
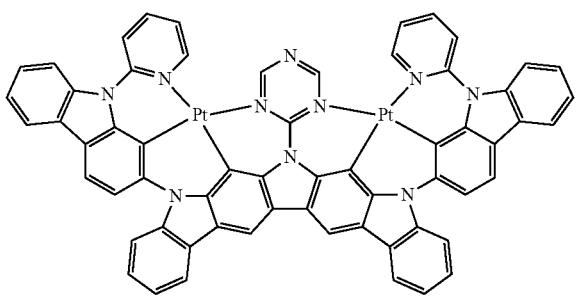
Compound 193
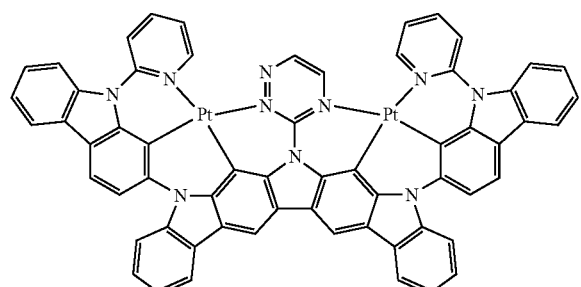
Compound 194
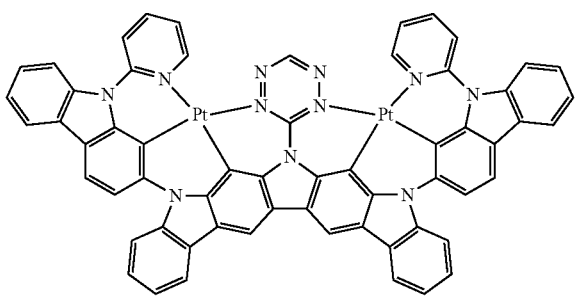
Compound 195
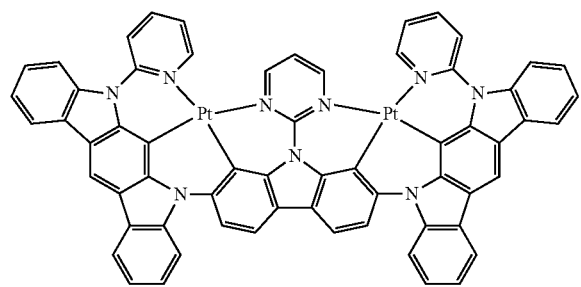
Compound 196
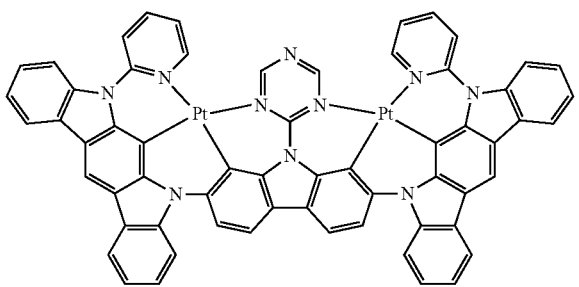

Compound 197
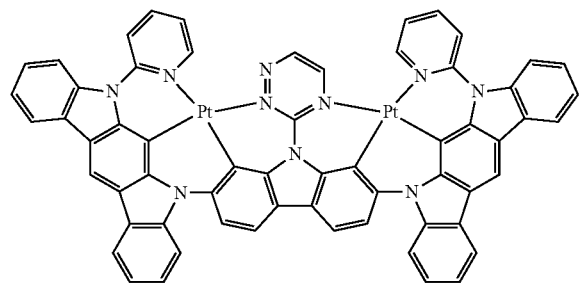
Compound 198
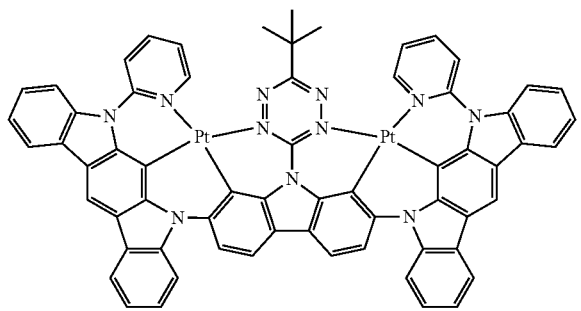
Compound 199
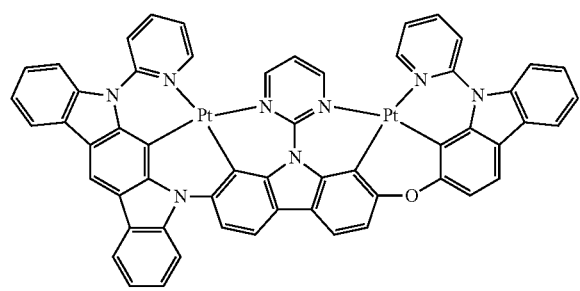
Compound 200
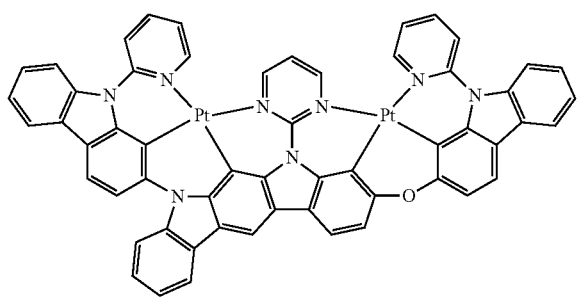
Compound 201
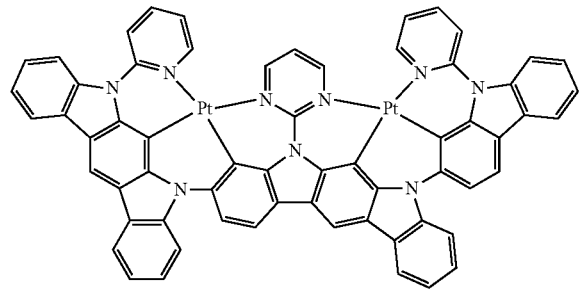
Compound 202
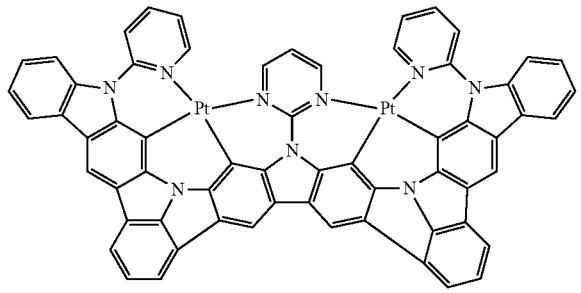
Compound 203
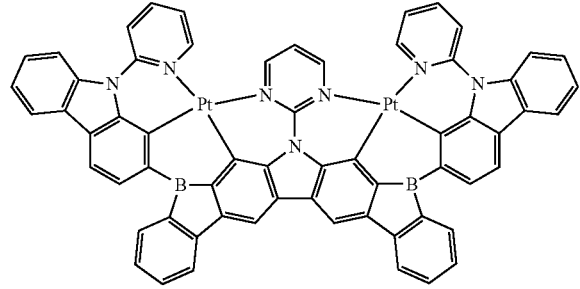
Compound 204
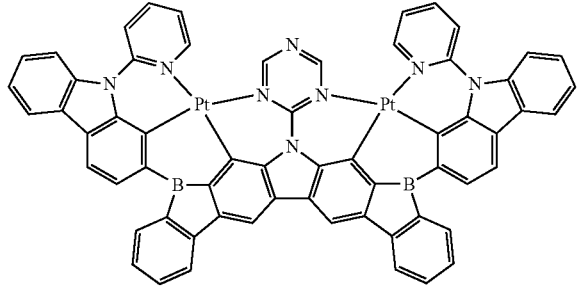
Compound 205
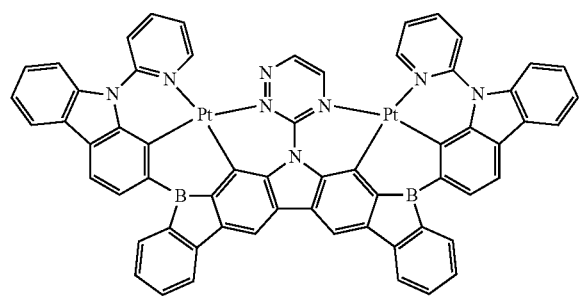
Compound 206
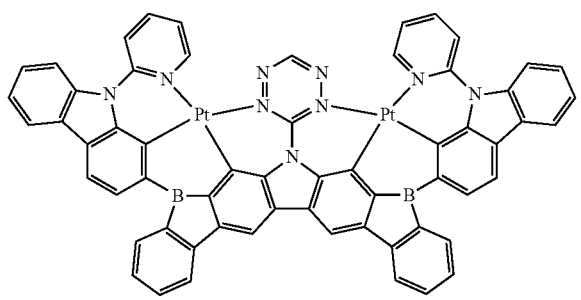

-continued
Compound 207
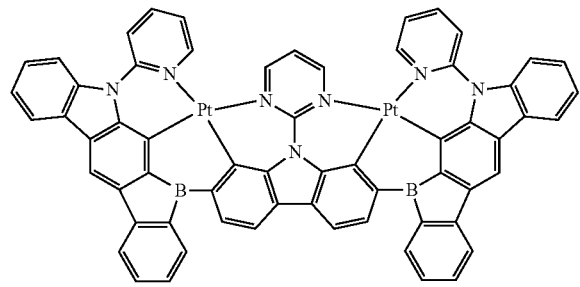
Compound 208
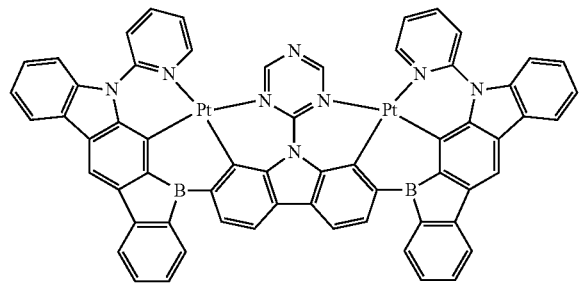
Compound 209
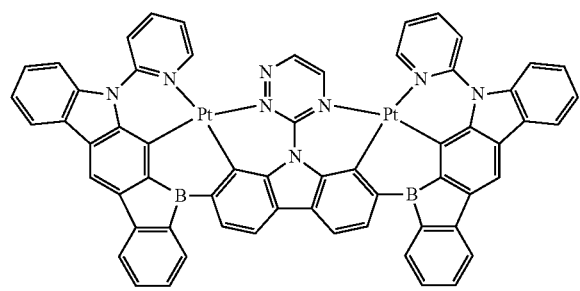
Compound 210
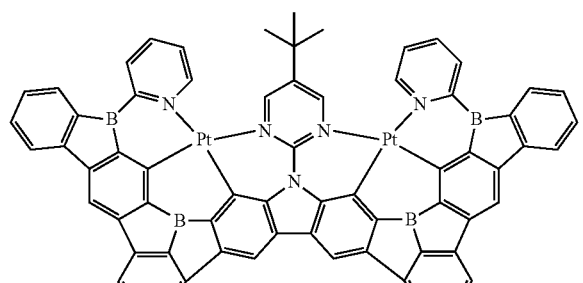
Compound 211
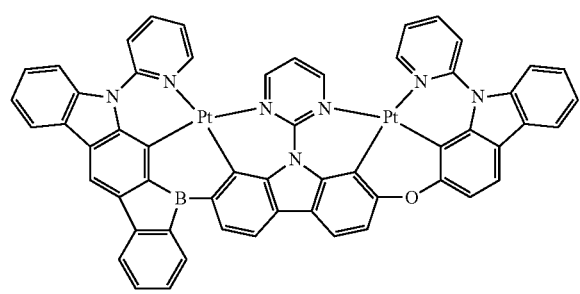
Compound 212
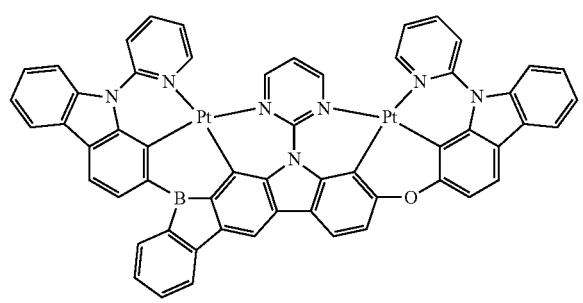
Compound 213
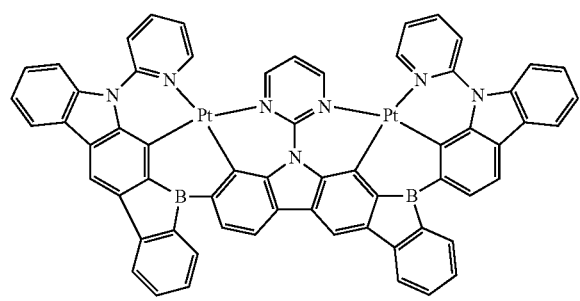
Compound 214
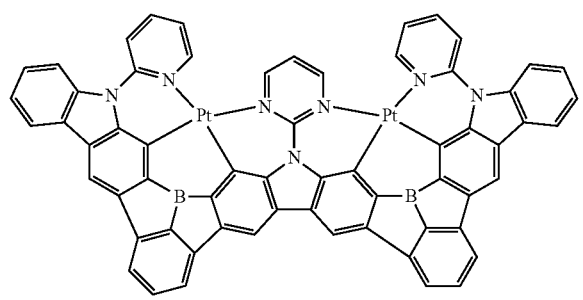
Compound 215
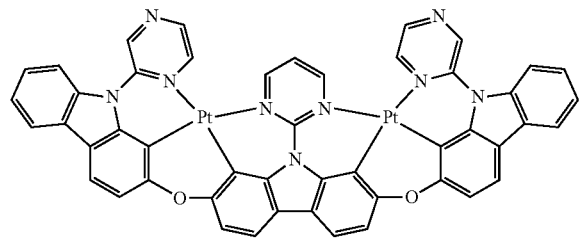
Compound 216
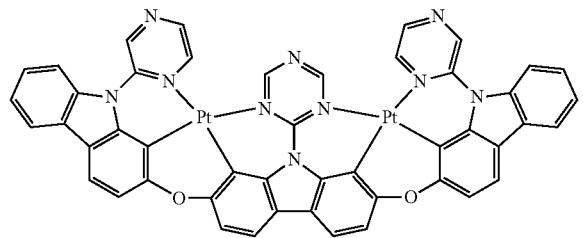

-continued
Compound 217
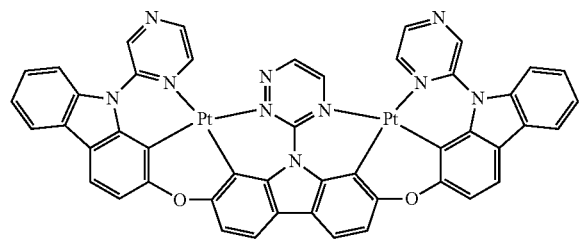
Compound 218
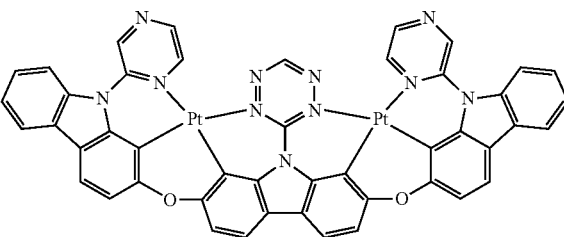
Compound 219
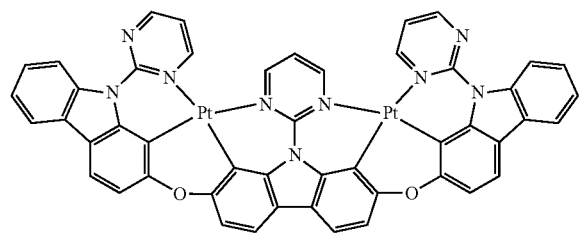
Compound 220
Compound 221
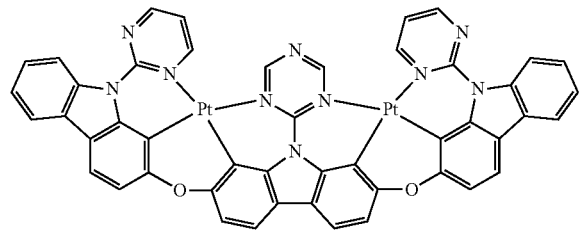
Compound 222
Compound 223
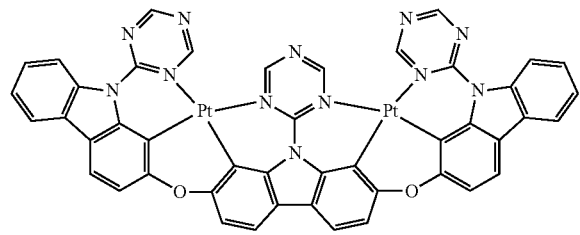
Compound 224
Compound 225
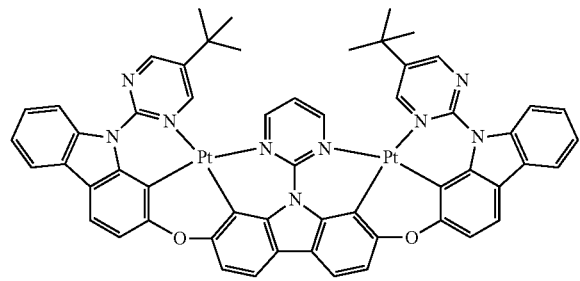
Compound 226
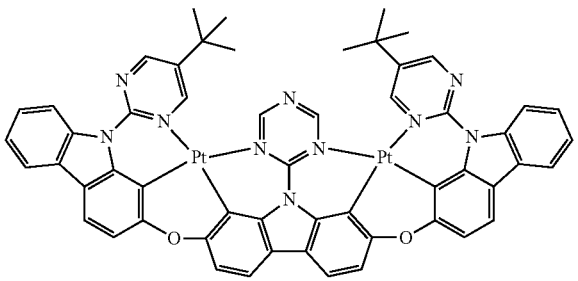

-continued
Compound 227
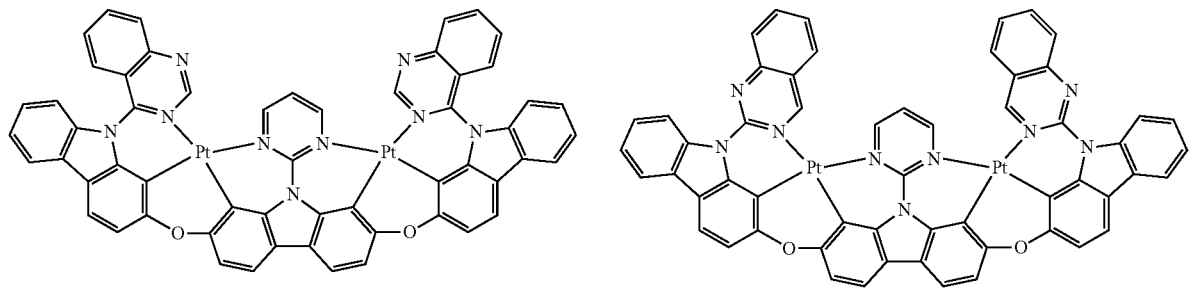
Compound 228
Compound 229
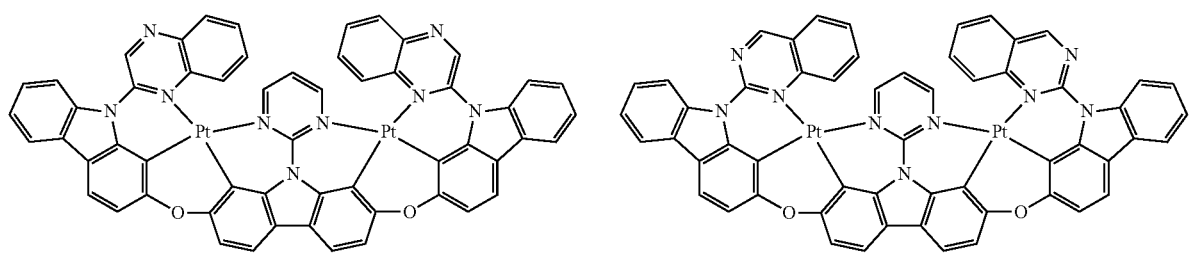
Compound 230
Compound 231
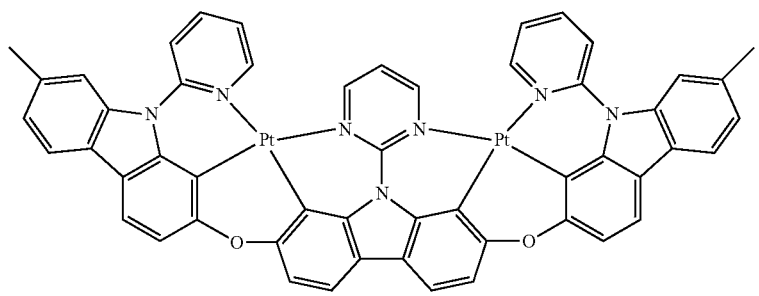
Compound 232
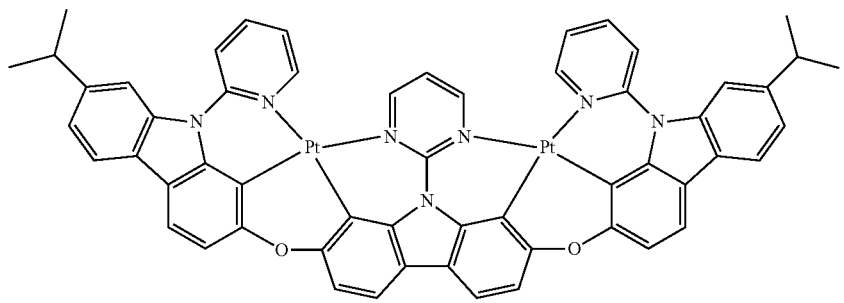
Compound 233
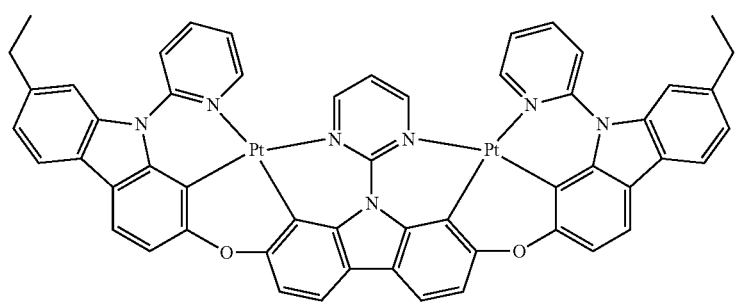

-continued
Compound 234
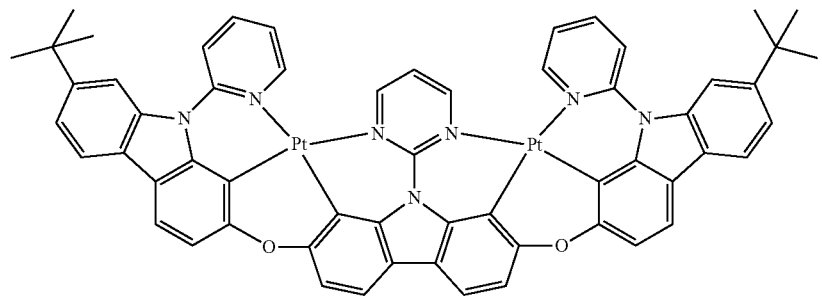
Compound 235
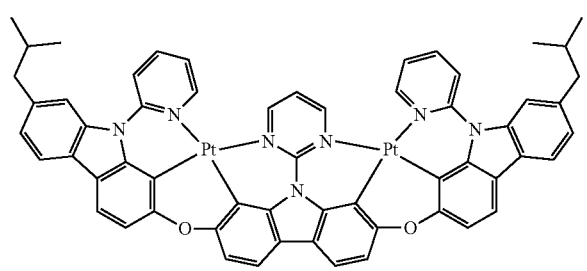
Compound 236
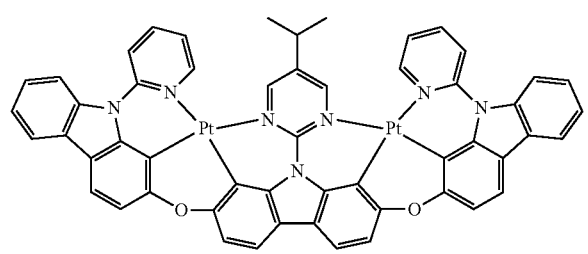
Compound 237
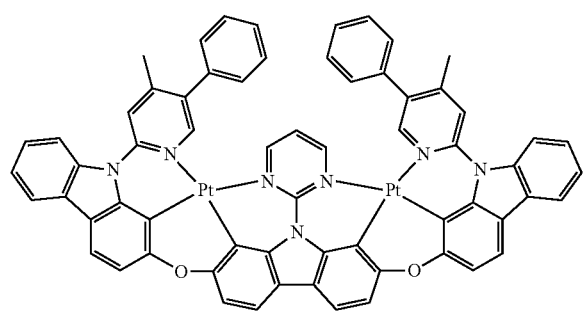
Compound 238
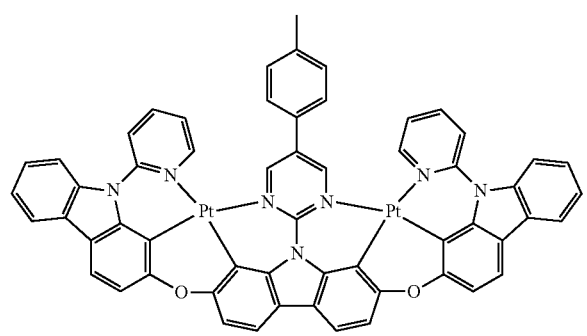
Compound 239
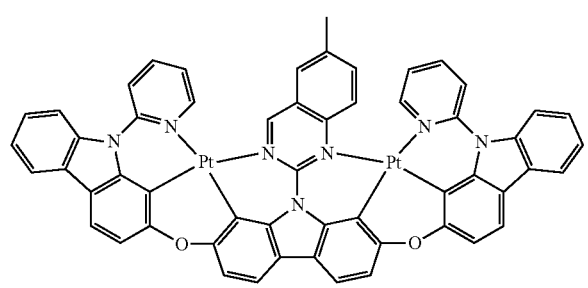
Compound 240
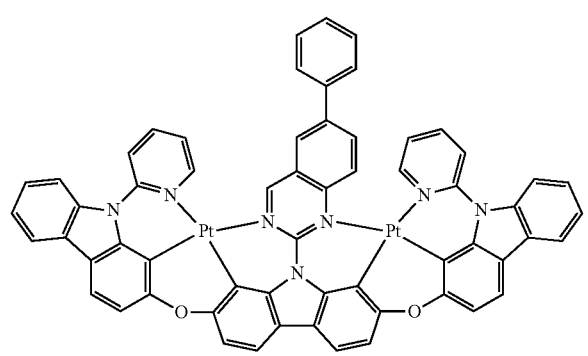

-continued

Compound 241

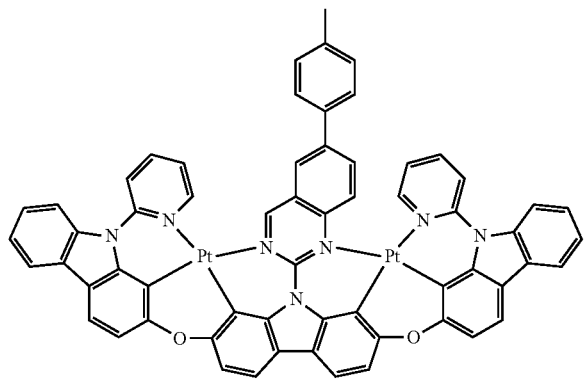

Compound 242

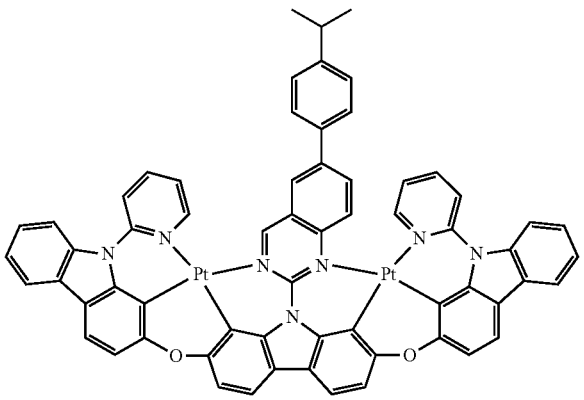

Compound 243

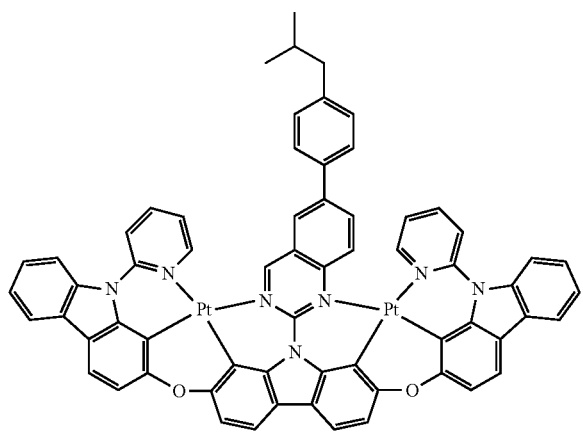

Compound 244

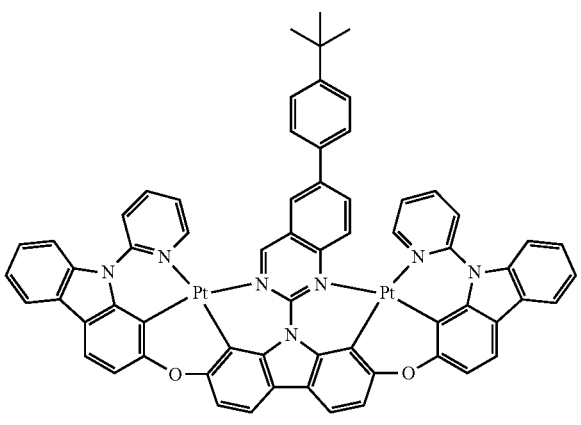

Compound 245

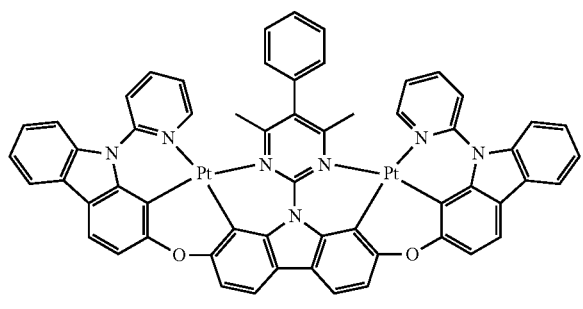

Compound 246

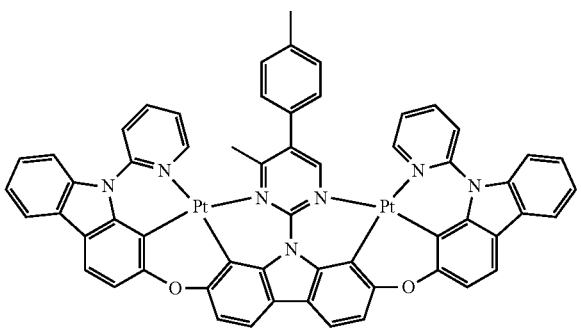

wherein $R^x$ is hydrogen, aryl, cycloalkyl, cycloalkenyl, heterocyclyl, heteroaryl, alkyl, alkenyl, alkynyl, deuterium, halogen, hydroxyl, thiol, nitro, cyano, amino, a mono- or di-alkylamino, a mono- or diaryl amino, alkoxy, aryloxy, haloalkyl, aralkyl, ester, nitrile, isonitrile, heteroary, alkoxycarbonyl, acylamino, alkoxycarbonylamino, aryloxycarbonylamino, sulfonylamino, sulfamoyl, carbamoyl, alkylthio, sulfinyl, ureido, phosphoramide, amercapto, sulfo, carboxyl, hydrzino, substituted silyl, or polymerizable, or any conjugate or combination thereof, 2. Devices Also disclosed herein are devices comprising one or more of the compounds disclosed herein.

The compounds disclosed herein are suited for use in a wide variety of devices, including, for example, optical and electro-optical devices, including, for example, photo-absorbing devices such as solar- and photo-sensitive devices, organic light emitting diodes (OLEDs), photo-emitting devices, or devices capable of both photo-absorption and emission and as markers for bio-applications.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Various methods for the preparation method of the inventive compounds described herein are recited in the examples. These methods are provided to illustrate various methods of preparation, but the present invention is not intended to be limited to any of the methods recited herein. Accordingly, one of skill in the art in possession of this disclosure could readily modify a recited method or utilize a different method to prepare one or more of the inventive compounds. The following aspects are only exemplary and are not intended to limit the scope of the invention. Temperatures, catalysts, concentrations, reactant compositions, and other process conditions can vary, and one of skill in the art, in possession of this disclosure, could readily select appropriate reactants and conditions for a desired complex.

$^1$H spectra were recorded at 400 MHz, $^{13}$C NMR spectra were recorded at 100 MHz on Varian Liquid-State NMR instruments in CDCl$_3$ or DMSO-d$_6$ solutions and chemical shifts were referenced to residual protiated solvent. If CDCl$_3$ was used as solvent, $^1$H NMR spectra were recorded with tetramethylsilane (δ=0.00 ppm) as internal reference; $^{13}$C NMR spectra were recorded with CDCl$_3$ (δ=77.00 ppm) as internal reference. If DMSO-d$_6$ was used as solvent, $^1$H NMR spectra were recorded with residual H$_2$O (δ=3.33 ppm) as internal reference; $^{13}$C NMR spectra were recorded with DMSO-d$_6$ (δ=39.52 ppm) as internal reference. The following abbreviations (or combinations thereof) were used to explain $^1$H NMR multiplicities: s=singlet, d=doublet, t=triplet, q=quartet, p=quintet, m=multiplet, br=broad.

Prophetic Synthetic Routes

A general proposed synthetic route for the compounds disclosed herein includes:

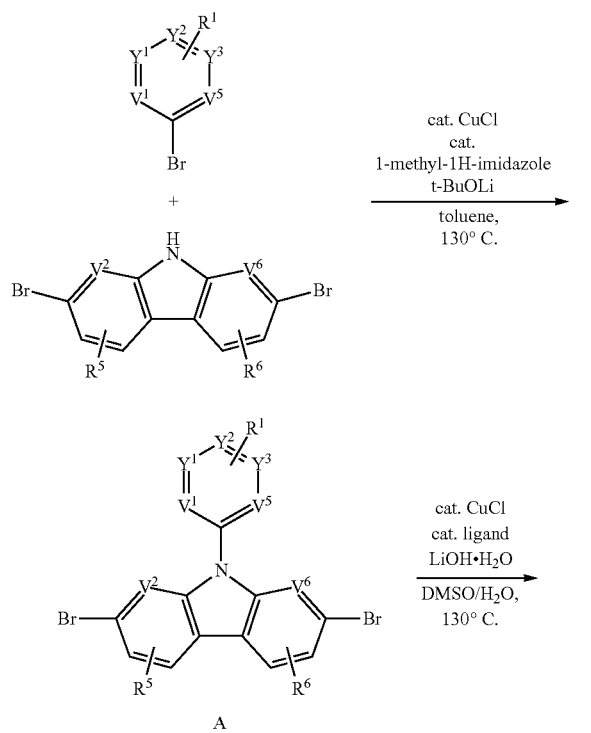

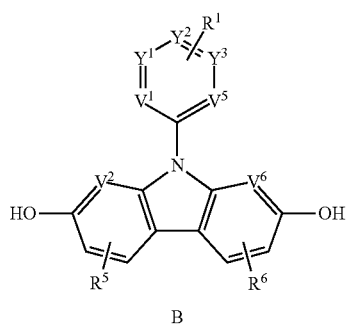

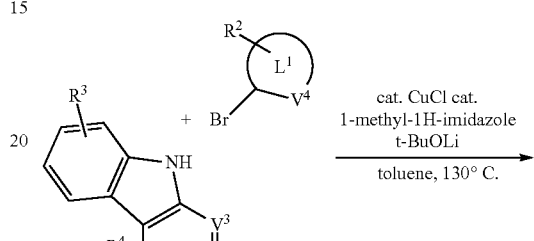

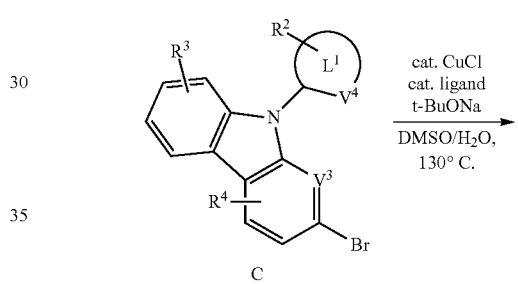

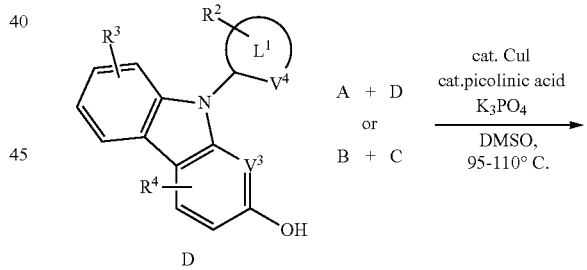

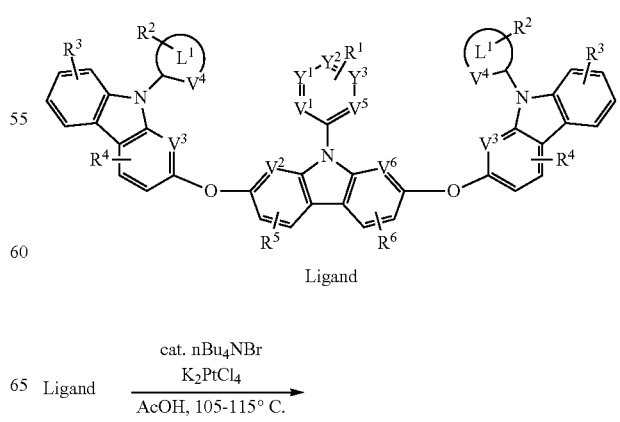

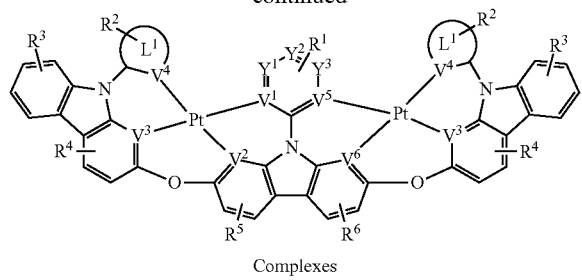

Complexes

1. Example 1

Platinum complex Compound 1 can be prepared according to the following scheme:

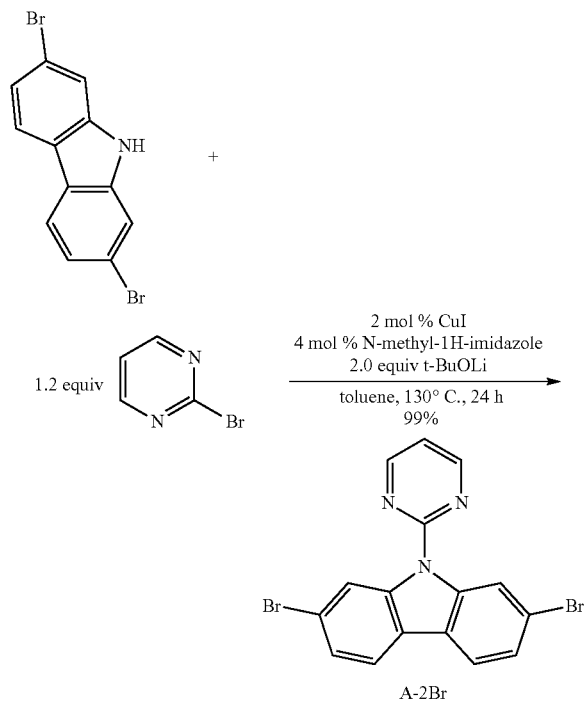

2,7-Dibromocarbazole (1.66 g, 5.10 mmol, 1.0 equiv), 2-bromopyrimidine (0.97 g, 6.10 mmol, 1.2 equiv), CuI (19.4 mg, 0.10 mmol, 0.02 equiv), t-BuOLi (0.82 g, 10.2 mmol, 2.0 equiv) were added to a dry three-necked flask equipped with a magnetic stir bar and a condenser. The flask was then evacuated and backfilled with nitrogen, this evacuation and backfill procedure was repeated twice. Then ligand N-methyl-1H-imidazole (16.0 uL, 0.20 mmol, 0.04 equiv) and solvent toluene (20 mL) were added under nitrogen. The mixture was then stirred at 130° C. for 24 hours until the 2-bromocarbazole was consumed completely monitored by TLC. The reaction mixture was cooled to room temperature and quenched with a solution of Na$_2$SO$_3$, diluted with EtOAc, filtered through a pad of celite and washed with EtOAc. The organic layer was then separated, dried over Na$_2$SO$_4$, filtered, the filtrate was concentrated, and the residue was purified through column chromatography on silica gel using petroleum ether/dichloromethane=5:1-3:2 as eluent to afford A-2Br as a white solid 2.03 g in 99% yield.

mp: 213.5-214.1° C. $^1$H NMR (500 MHz, DMSO-d$_6$): δ 7.47 (t, J=4.5 Hz, 1H), 7.58 (dd, J=8.5, 1.5 Hz, 2H), 8.22 (d, J=3.0 Hz, 2H), 9.02 (d, J=1.5 Hz, 2H), 9.05 (d, J=5.0 Hz, 2H). $^{13}$C NMR (100 MHz, CDCl$_3$): δ 116.66, 119.75, 120.47, 120.59, 124.00, 125.80, 139.81, 158.02, 158.60. HRMS (EI): calcd for C$_{16}$H$_9$N$_3$Br$_2$ [M]$^+$ 400.9163, found 400.9178.

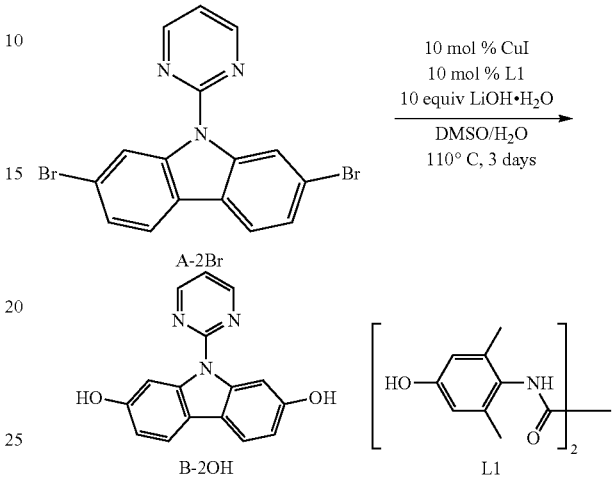

2,7-Dibromo-9-(pyrimidin-2-yl)-9H-carbazole A-2Br (4.0 g, 10.0 mmol, 1.0 eq), CuI (190.5 mg, 1.0 mmol, 0.1 eq), L1 (328.3 mg, 1.00 mmol, 0.10 eq) and LiOH.H$_2$O (4.2 g, 100.0 mmol, 10.0 eq) were added to a dry flask equipped with a magnetic stir bar. The tube was then evacuated and backfilled with nitrogen, this evacuation and backfill procedure was repeated twice. Then DMSO/H$_2$O (70 mL/30 mL) were added into the tube under nitrogen atmosphere. The tube was placed in oil bath (110° C.) and stirred for 3 days until the starting material was consumed completely monitoring by TLC. Then the mixture was cooled down, diluted with ethyl acetate (100 mL) and water (100 mL). The organic layer was then separated, and aqueous layer was extracted with ethyl acetate three times (50 mL×3). The combined organic layer was dried over anhydrous Na$_2$SO$_4$, filtered and concentrated under reduced pressure. The residue was purified through column chromatography on silica gel using petroleum ether/ethyl acetate (5:1-1:1) as eluent to afford the desired product as a gray solid 1.96 g in 71% yield. $^1$H NMR (500 MHz, DMSO-d$_6$): δ 6.77 (dd, J=8.5, 2.0 Hz, 2H), 7.38 (t, J=5.0 Hz, 1H), 7.78 (d, J=8.5 Hz, 2H), 8.19 (d, J=2.0 Hz, 2H), 8.97 (d, J=5.0 Hz, 2H), 9.46 (s, 2H). $^{13}$C NMR (126 MHz. DMSO-d$_6$): δ 102.80, 110.90, 116.71, 117.79, 119.03, 139.62, 115.66, 158.30, 158.44. HRMS (ESI): calcd for C$_{16}$H$_{12}$N$_3$O$_2$ [M+H]$^+$ 278.0924, found 278.0916.

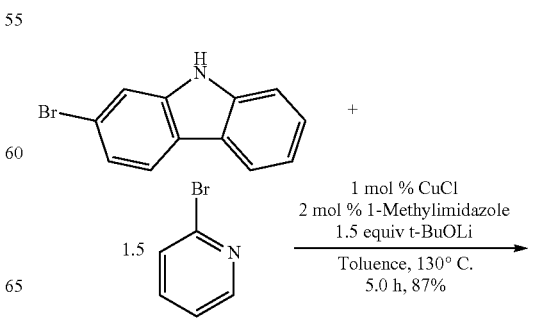

-continued

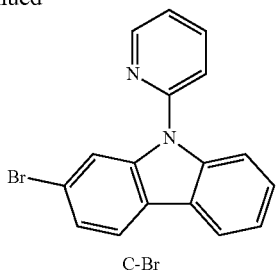
C-Br

2-Bromo-9H-carbazole (14.77 g, 60.0 mmol, 1.0 eq), CuCl (60.0 mg, 0.6 mmol, 0.01 eq) and lithium t-butoxide (7.21 g, 90.0 mmol, 1.5 eq) were added to a 500 mL three-neck bottom flask with magnetic stir bar. Then the flask was evacuated and backfilled with nitrogen. This procedure was repeated for total of three times. Then 2-bromopyridine (8.58 mL, 90.0 mmol, 1.5 eq), 1-methylimidazole (95.1 uL, 1.2 mmol, 0.02 eq) and toluent (240 mL) were added into flask under nitrogen atmosphere. The flask was placed in 130° C. oil bath and stirred for 5.0 h. Cooled down, 100 mL solution of $Na_2SO_3$ was added. Then vacuum filtered and washed with ethyl acetate. The organic layer was separated, and the aqueous layer was extracted with EtOAc (100 mL×3). Then the combined organic phase was washed with 50 mL water, dried over $Na_2SO_4$ and filtered, and the filtrate was concentrated in vacuum. The residue was recrystallized in PE/DCM (40 mL/5 mL) to afford the desired product as a white solid 16.77 g in 87%. $^1$H NMR (500 MHz, CDCl$_3$): δ 7.31-7.34 (m, 2H), 7.42 (dd, J=8.0, 1.5 Hz, 1H), 7.44-7.47 (m, 1H), 7.61 (d, J=8.5 Hz, 1H), 7.77 (d, J=8.0 Hz, 1H), 7.93-7.96 (m, 2H), 8.01 (d, J=1.5 Hz, 1H), 8.08 (d, J=7.5 Hz, 1H), 8.73 (d, J=5.0, 1.5 Hz, 1H).

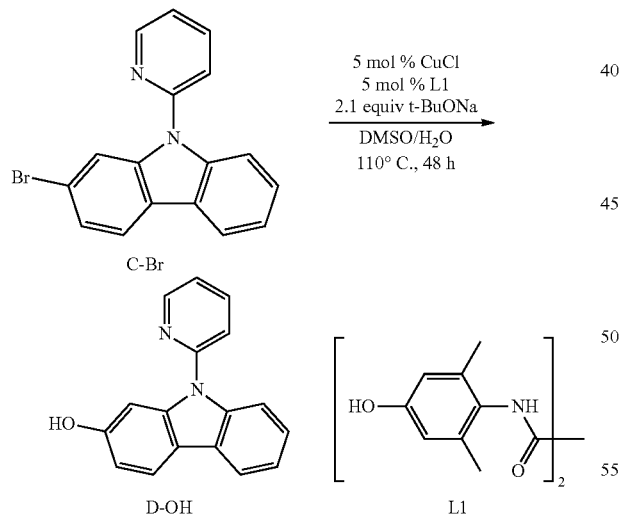

2-Bromo-9-(2-pyridinyl)-carbazole (9.70 g, 30.0 mmol, 1.0 eq), CuCl (148.5 mg, 1.5 mmol, 0.05 eq), L1 (493.0 mg, 1.5 mmol, 0.05 eq) and t-BuONa (6.05 g, 63.0 mmol, 2.1 eq) were added to a dry flask equipped with a magnetic stir bar. The flask was then evacuated and backfilled with nitrogen, this evacuation and backfill procedure was repeated twice. Then DMSO/H$_2$O (37.5 mL/9.5 mL) were added into the tube under nitrogen atmosphere. The tube was placed in oil bath (110° C.) and stirred for 48 h until the starting material was consumed completely monitoring by TLC. Then the mixture was cooled to room temperature, H$_2$O (100 mL) and EtOAc (100 mL) were added, filtered through a pad of celite, and washed with EtOAc three times. The organic layer was then separated, and the aqueous layer was extracted with EtOAc (100 mL×5). The combined organic layer was washed with water (50 mL) and then dried over Na$_2$SO$_4$ and filtered, and the filtrate was concentrated in vacuum. The residue was recrystallized in PE/EtOAc (10 mL/10 mL) to afford the desired product as a gray solid 5.77 g. The mother liquor was concentrated, and the residue was purified through column chromatography on silica gel using PE/DCM=5:1-3:1 as eluent to afford the product as a gray solid 1.5 g. The total yield was 93%. $^1$H NMR (500 MHz, DMSO-d$_6$): δ 6.79 (dd, J=8.5, 2.0 Hz, 1H), 7.18 (d, J=2.0 Hz, 1H), 7.23-7.26 (m, 1H), 7.32 (td, J=8.5, 1.0 Hz, 1H), 7.47 (ddd, J=7.5, 5.0, 1.0 Hz, 1H), 7.69 (d, J=8.0 Hz, 1H), 7.74 (d, J=8.0 Hz, 1H), 7.99 (d, J=8.5 Hz, 1H), 8.06 (d, J=7.5 Hz, 1H), 8.11 (td, J=8.0, 2.0 Hz, 1H), 8.72 (ddd, J=5.0, 2.0, 0.5 Hz, 1H), 9.61 (s, 1H). $^{13}$C NMR (126 MHz, DMSO-d$_6$): δ 97.10, 110.34, 110.77, 115.85, 119.01, 119.12, 120.78, 121.08, 121.80, 124.02, 124.48, 138.79, 139.29, 140.54, 149.45, 150.88, 157.02. HRMS (ESI): calcd for C$_1$H$_{13}$N$_2$O [M+H]$^+$ 261.1022, found 261.1028.

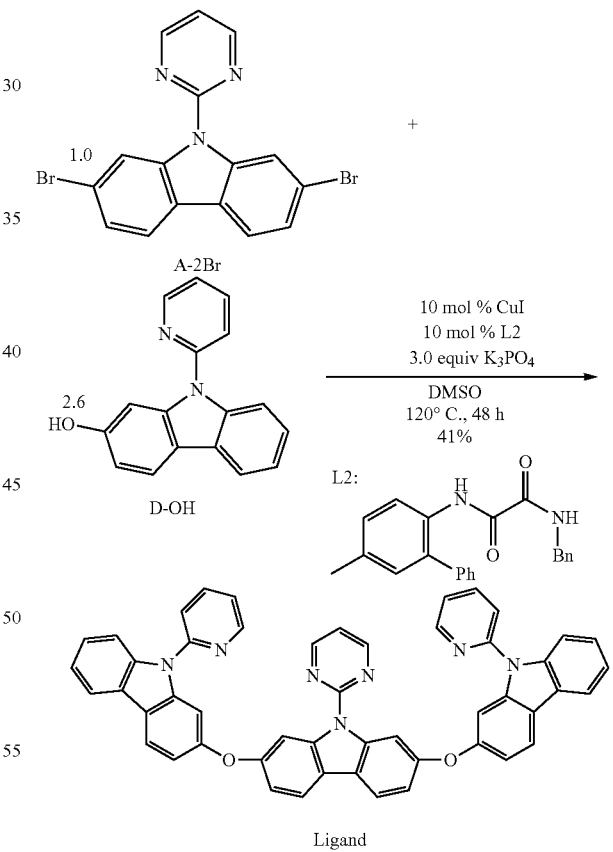

2,7-Dibromo-9-(pyrimidin-2-yl)-9H-carbazole A-2Br (100.0 mg, 0.25 mmol, 1.0 eq), 9-(pyridin-2-yl)-9H-carbazol-2-ol D-OH (169.19 mg, 0.65 mmol, 2.6 eq), CuI (4.76 mg, 0.03 mmol, 0.10 eq), L2 (8.61 mg, 0.03 mmol, 0.10 eq) and K$_3$PO$_4$ (159.20 mg, 0.75 mmol, 3.0 eq) were added to a dry Schlenk tube equipped with a magnetic stir bar. The tube was then evacuated and backfilled with nitrogen, this evacuation and backfill procedure was repeated twice. Then DMSO (1.0 mL) was added into the tube under nitrogen atmosphere. The tube was placed in oil bath (120° C.) and stirred for 48 h. Then the mixture was cooled to room temperature, H₂O (30 mL) and EtOAc (30 mL) were added, filtered through a pad of celite, and washed with EtOAc. The organic layer was then separated, and the aqueous layer was extracted with EtOAc (20 mL×2). The combined organic layer was dried over Na₂SO₄, filtered, and the filtrate was concentrated in vacuum. The residue was purified through column chromatography on silica gel using petroleum ether/ ethyl acetate (4:1-1:1) as eluent to afford the desired product as a white solid 78.3 mg in 41% yield. ¹H NMR (500 MHz, CDCl₃): δ 7.02 (t, J=5.0 Hz, 1H), 7.07 (dd, J=7.5, 2.5 Hz, 2H), 7.09 (dd, J=7.5, 2.5 Hz, 2H), 7.24-7.27 (m, 2H), 7.30-7.33 (m, 2H), 7.39-7.43 (m, 2H), 7.60 (d, J=2.0 Hz, 2H), 7.62 (td, J=8.0, 1.0 Hz, 2H), 7.82 (d, J=8.0 Hz, 2H), 7.85-7.88 (m, 2H), 7.92 (d, J=8.5 Hz, 2H), 8.04-8.07 (m, 4H), 8.65 (d, J=2.5 Hz, 2H), 8.66 (ddd, J=5.0, 2.0, 1.0 Hz, 2H), 8.68 (d, J=5.0 Hz, 2H).

J=8.5 Hz, 2H), 9.04 (dd, J=6.0, 1.5 Hz, 2H), 9.55 (d, J=5.5 Hz, 2H). HRMS (MALDI_DART Positive): calcd for C₅₀H₂₇N₇O₂Pt₂ [M]⁺ 1147.1522, found 1147.1526.

What is claimed is:

1. A compound of Formula I:

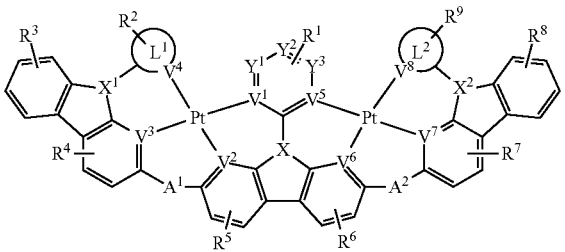

Formula I

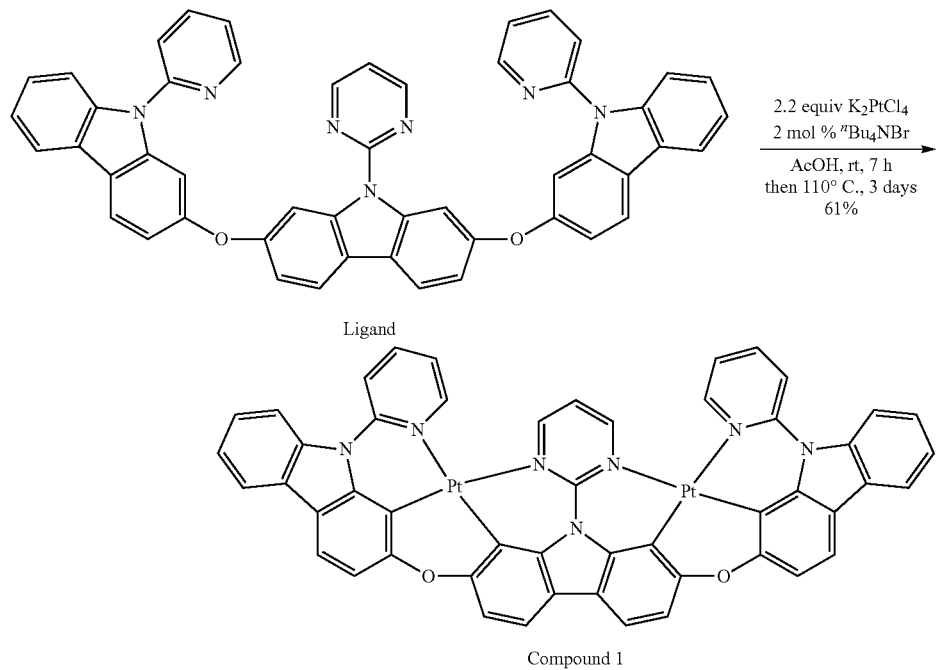

The ligand (78.3 mg, 0.11 mmol, 1.0 eq), K₂PtCl₄ (93.9 mg, 0.23 mmol, 2.2 eq), ⁿBu₄NBr (7.1 mg, 0.022 mmol, 0.2 eq) were added to a dry Schlenk tube equipped with a magnetic stir bar. The tube was then evacuated and backfilled with nitrogen, this evacuation and backfill procedure was repeated twice. Then AcOH (14 mL) were added into the tube under nitrogen atmosphere. The mixture was stirred at room temperature for 7 h. Then it was placed in oil bath (110° C.) and stirred for 3 days. The mixture was cooled down and the solvent was evaporated under reduced pressure. The residue was purified through column chromatography on silica gel using petroleum ether/dichloromethane (1:3-0:1) as eluent to afford the desired product as a yellow solid 77.8 mg in 610 yield. ¹H NMR (500 MHz, DMSO-d₆): δ 7.04 (t, J=5.5 Hz, 1H), 7.22 (d, J=8.0 Hz, 2H), 7.31 (d, J=8.0 Hz, 2H), 7.37-7.40 (m, 2H), 7.42-7.45 (m, 2H), 7.50-7.53 (m, 2H), 7.87 (d, J=8.5 Hz, 2H), 7.95 (d, J=8.0 Hz, 2H), 8.10 (d, J=8.0 Hz, 2H), 8.17-8.21 (m, 4H), 8.26 (d, wherein each of L¹ and L² is independently a six-membered carbocyclic, heterocyclic, heteroaryl ring;

wherein each of Y¹, Y², Y³ independently comprises N and C;

wherein V¹, V², V³, V⁴, V⁵, V⁶, V⁷ and V⁸ are coordinated with M¹ or M² and each independently comprises N and C; and at least two of V¹, V², V³ and V⁴ are N, at least two of V⁵, V⁶, V⁷ and V⁸ are N;

wherein each of A¹ and A² is independently selected from the group consisting O, S, CH₂, CD₂, CRᵃRᵇ, C=O, SiRᵃRᵇ, GeH₂, GeRᵃRᵇ, NH, NRᶜ, PH, PRᶜ, RᶜP=O, AsRᶜ, RᶜAs=O, S=O, SO₂, Se, Se=O, SeO₂, BH, BRᶜ, RᶜBi=O, BiH, or BiRᶜ;

wherein each of X, X¹ and X² is independently selected from the group consisting N, B, CH, CD, CRᵃ, SiH, SiD, SiRᵃ, GeH, GeD, GeRᵈ, P, P=O, As, As=O, Bi or Bi=O;

wherein R¹, R², R³, R⁴, R⁵, R⁶, R⁷, R⁸ and R⁹ may represent mono-, di, tri, tetra-substitutions, or no substitution, and R¹, R², R³, R⁴, R⁵, R⁶, R⁷, R⁸, R⁹, $R^a$, $R^b$, $R^c$ and $R^d$ are independently selected from the group consisting hydrogen, deuterium, aryl, cycloalkyl, cycloalkenyl, heterocyclyl, heteroaryl, alkyl, alkenyl, alkynyl, halogen, hydroxyl, thiol, nitro, cyano, amino, a mono- or di-alkylamino, a mono- or diaryl amino, alkoxy, aryloxy, haloalkyl, aralkyl, ester, nitrile, isonitrile, heteroary, alkoxycarbonyl, acylamino, alkoxycarbonylamino, aryloxycarbonylamino, sulfonylamino, sulfamoyl, carbamoyl, alkylthio, sulfinyl, ureido, phosphoramide, amercapto, sulfo, carboxyl, hydrzino, substituted silyl, or any conjugate or combination thereof; Two or more adjacent R¹, R², R³, R⁴, R⁵, R⁶, R⁷, R⁸ and R⁹ are optionally joined to form a fused ring;

wherein $R^a$, $R^b$, $R^c$ and $R^d$ may represent mono-, di, tri, tetra-substitutions, or no substitution, and $R^a$, $R^b$, $R^c$ and $R^d$ are independently selected from the group consisting hydrogen, deuterium, aryl, cycloalkyl, cycloalkenyl, heterocyclyl, heteroaryl, alkyl, alkenyl, alkynyl, halogen, hydroxyl, thiol, nitro, cyano, amino, a mono- or di-alkylamino, a mono- or diaryl amino, alkoxy, aryloxy, haloalkyl, aralkyl, ester, nitrile, isonitrile, heteroary, alkoxycarbonyl, acylamino, alkoxycarbonylamino, aryloxycarbonylamino, sulfonylamino, sulfamoyl, carbamoyl, alkylthio, sulfinyl, ureido, phosphorannide, annercapto, sulfo, carboxyl, hydrzino, substituted silyl, or any conjugate or combination thereof.

2. The compound as described in claim 1, wherein

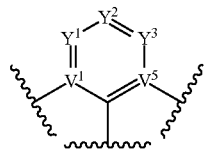

is selected from the group consisting

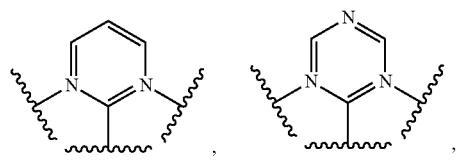

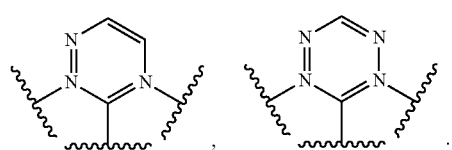

3. The compound as described in claim 1, wherein the compound has the structure of Formula III, Formula IV, Formula V, or Formula VI:

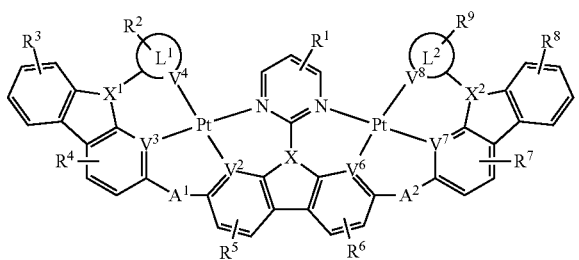

Formula II

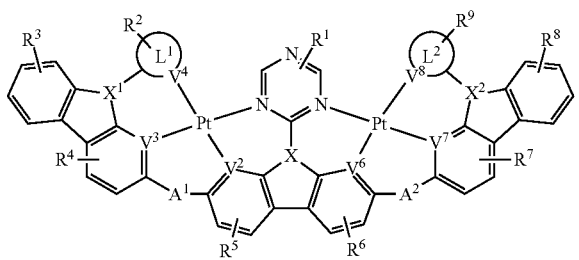

Formula III

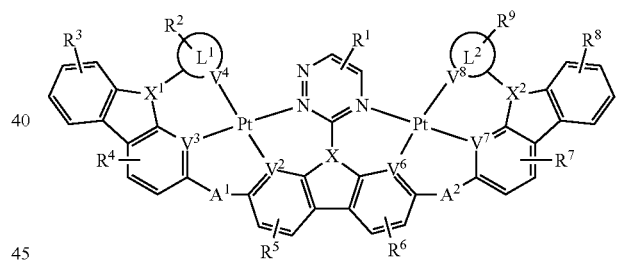

Formula IV

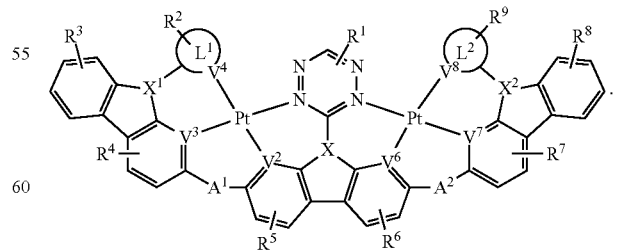

Formula V

4. The compound as described in claim 1, wherein the compound has the structure of from Compound 1-Compound 246:

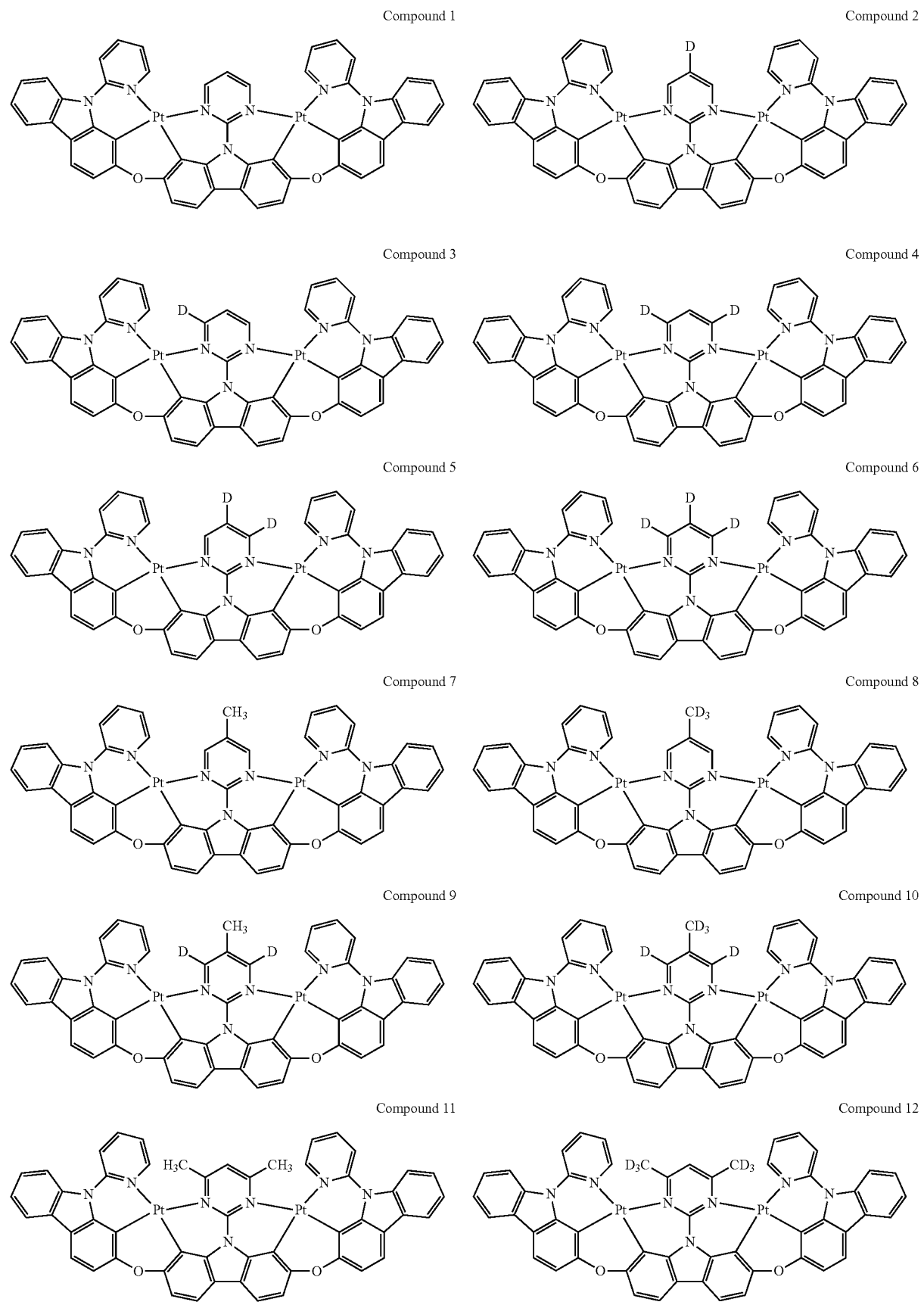

-continued
Compound 13
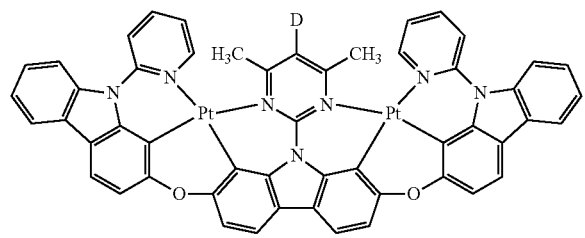
Compound 14
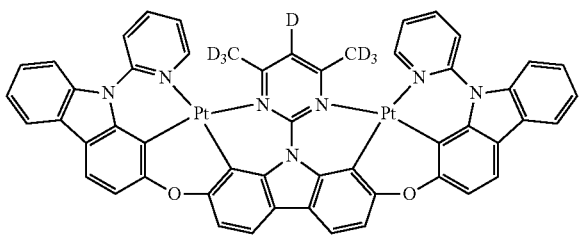
Compound 15
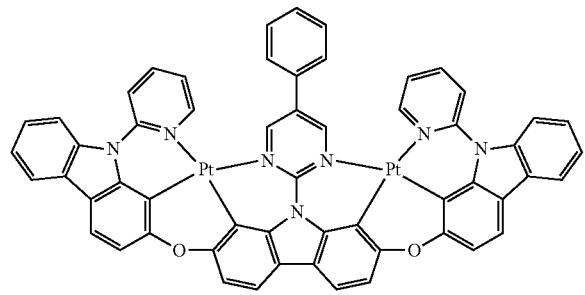
Compound 16
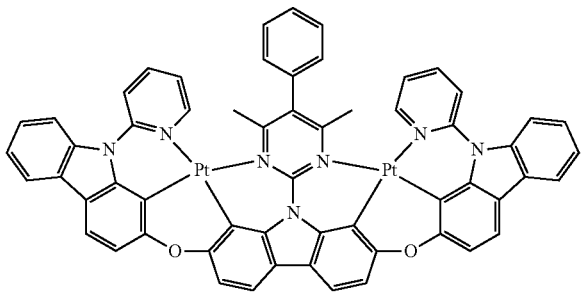
Compound 17
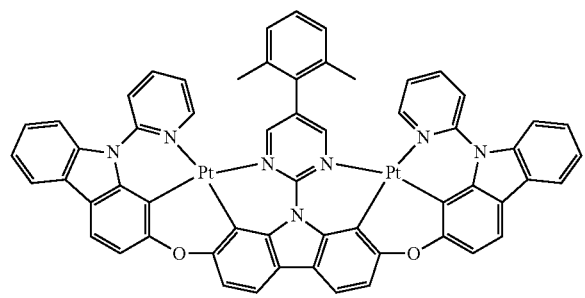
Compound 18
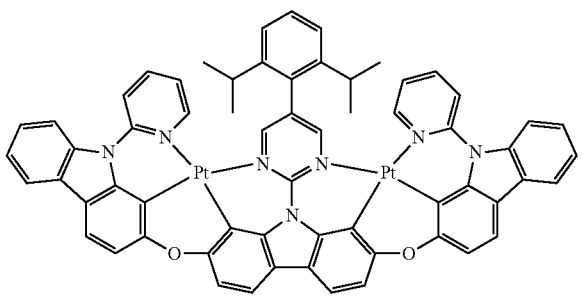
Compound 19
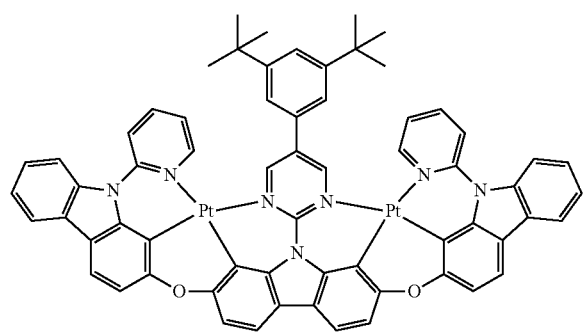
Compound 20
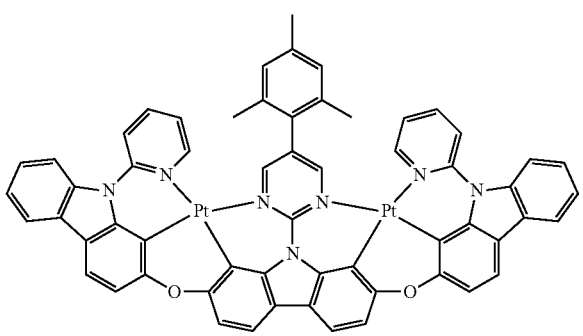
Compound 21
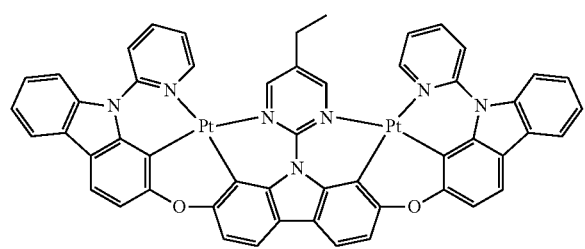
Compound 22
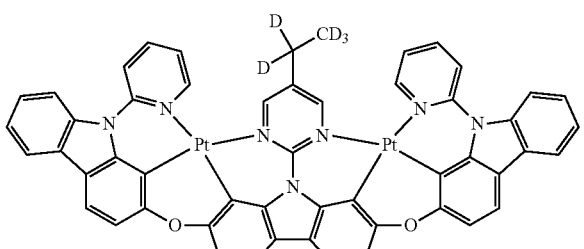

-continued
Compound 23
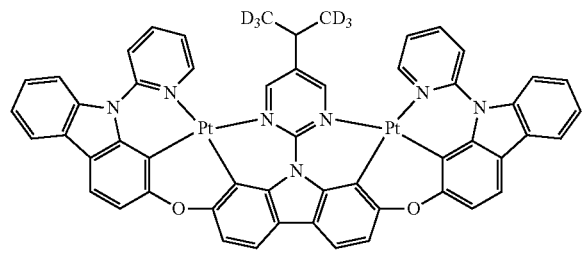
Compound 24
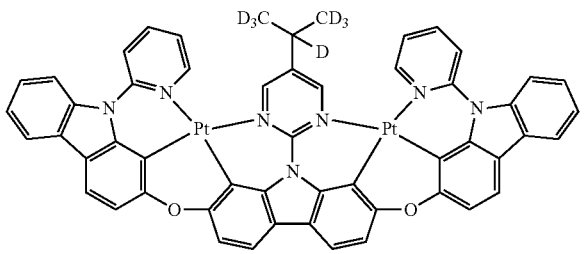
Compound 25
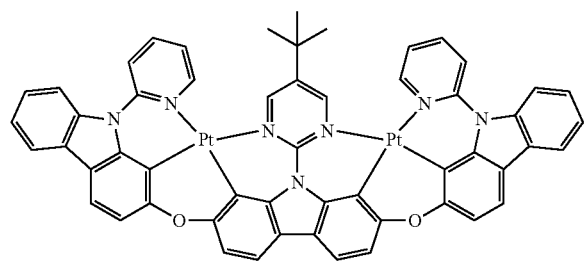
Compound 26
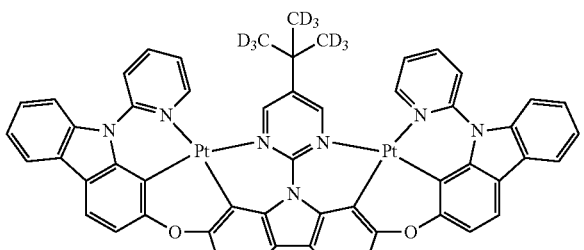
Compound 27
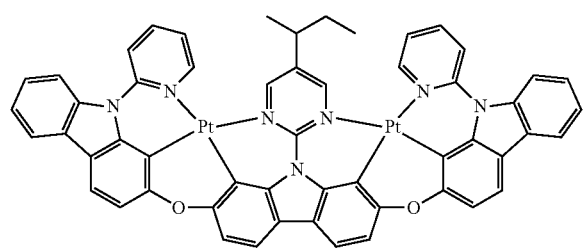
Compound 28
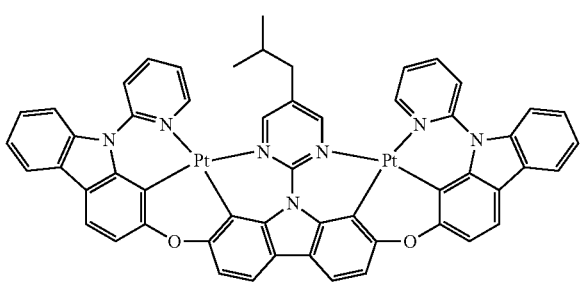
Compound 29
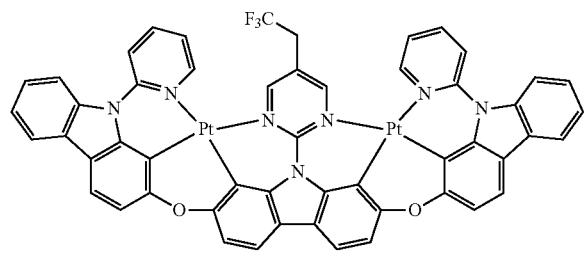
Compound 30
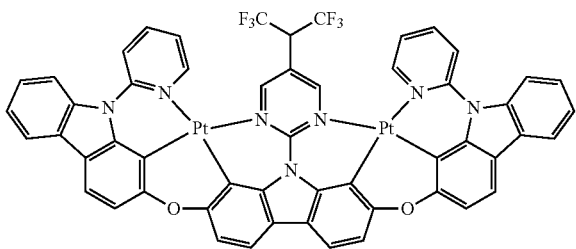
Compound 31
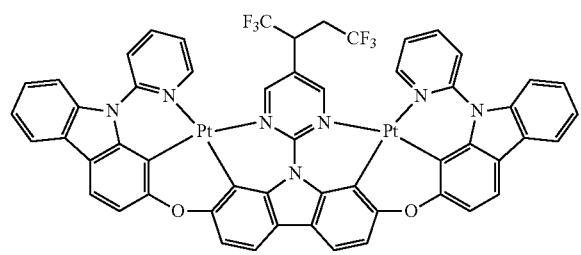
Compound 32
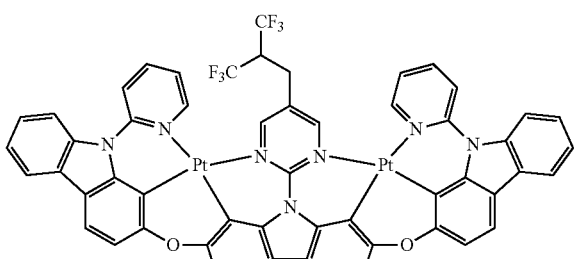

-continued
Compound 33
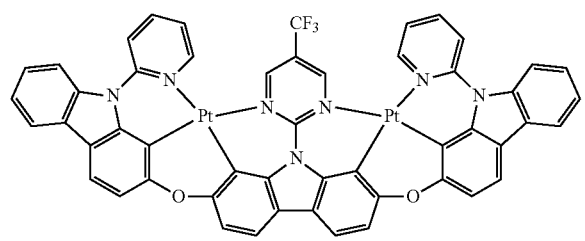
Compound 34
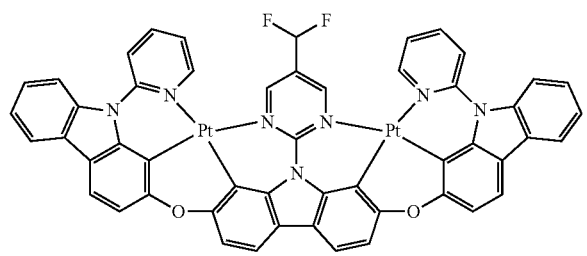
Compound 35
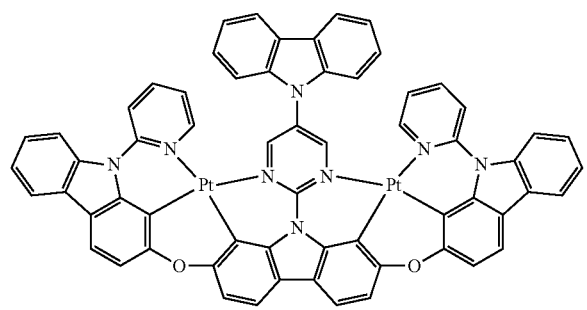
Compound 36
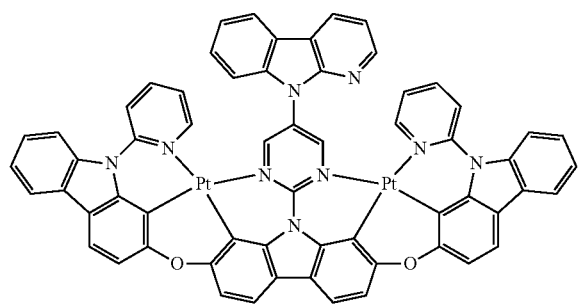
Compound 37
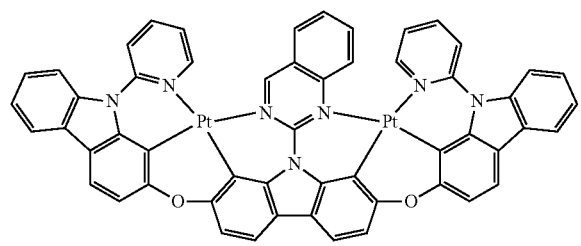
Compound 38
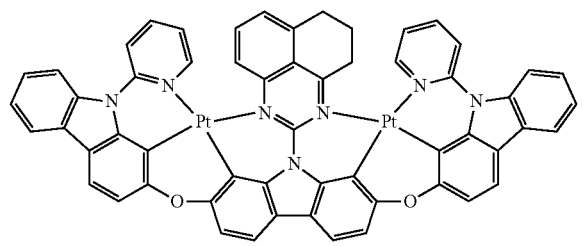
Compound 39
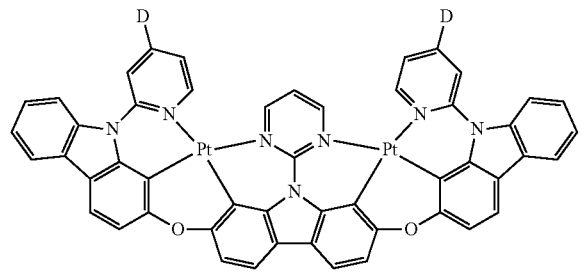
Compound 40
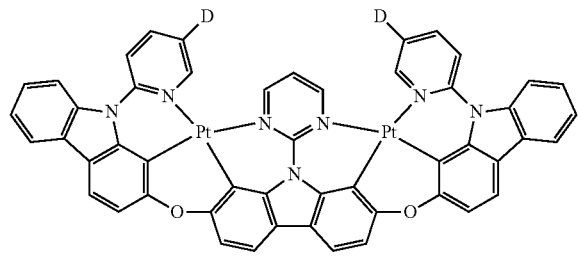
Compound 41
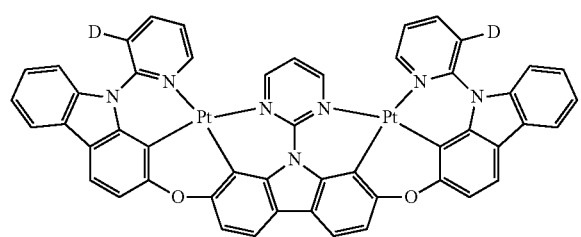
Compound 42
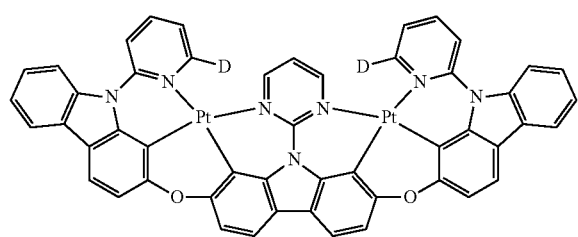

-continued
Compound 43
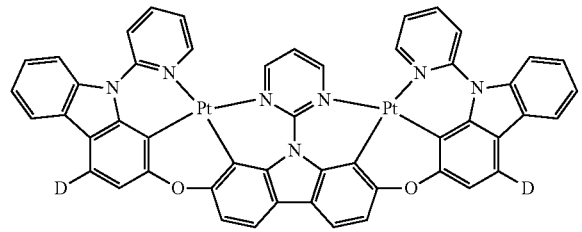
Compound 44
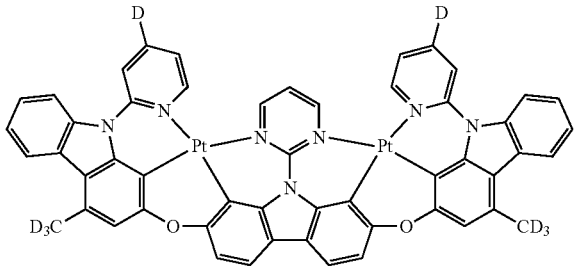
Compound 45
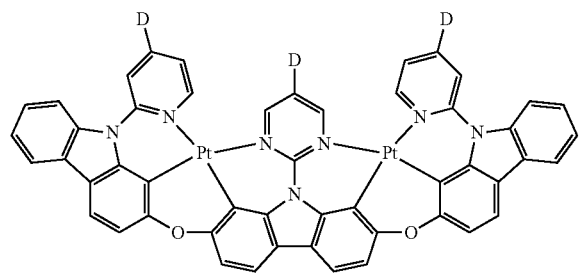
Compound 46
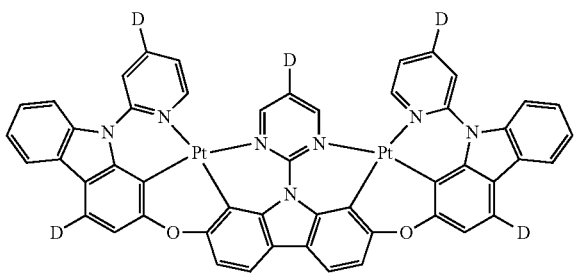
Compound 47
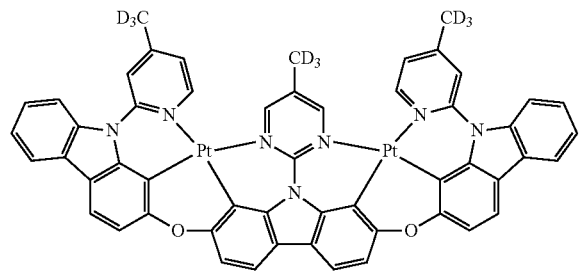
Compound 48
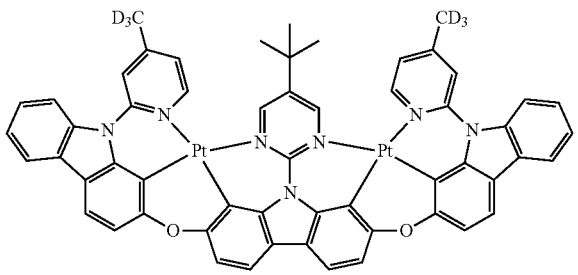
Compound 49
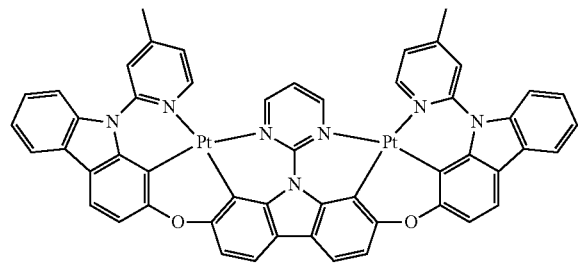
Compound 50
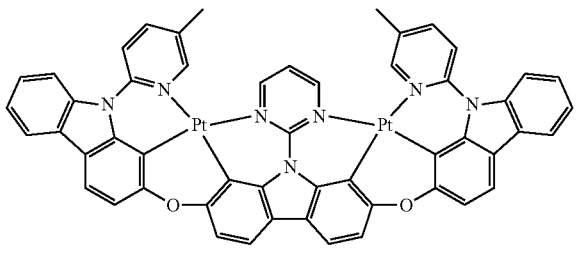
Compound 51
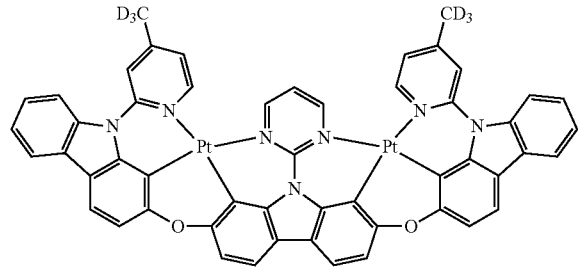
Compound 52
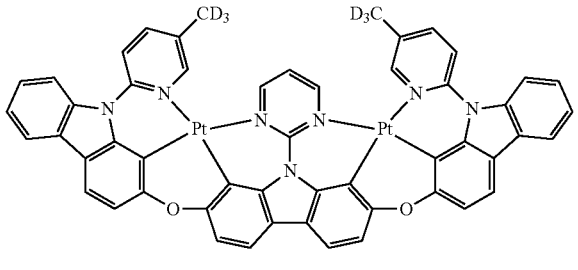

-continued
Compound 53
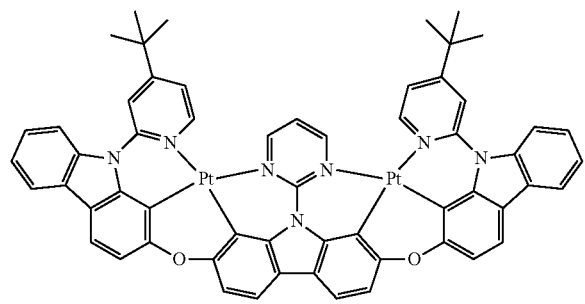
Compound 54
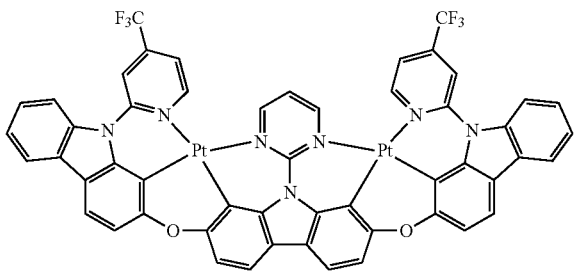
Compound 55
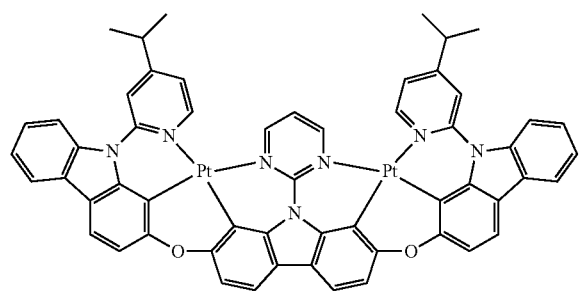
Compound 56
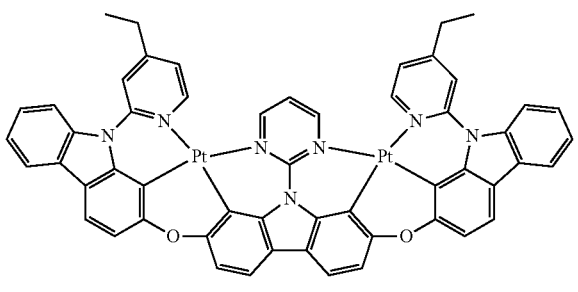
Compound 57
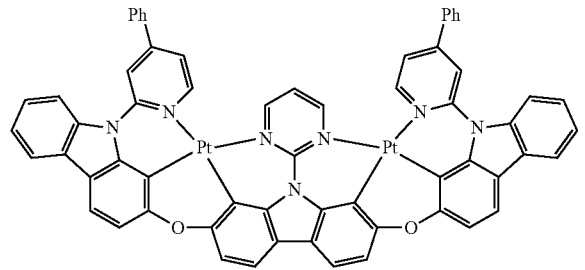
Compound 58
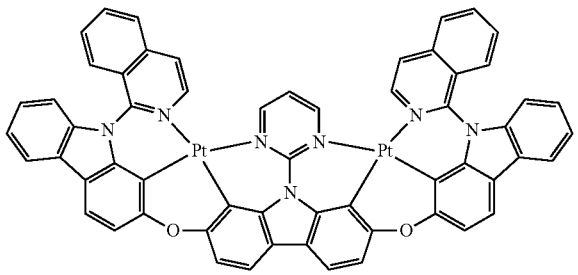
Compound 59
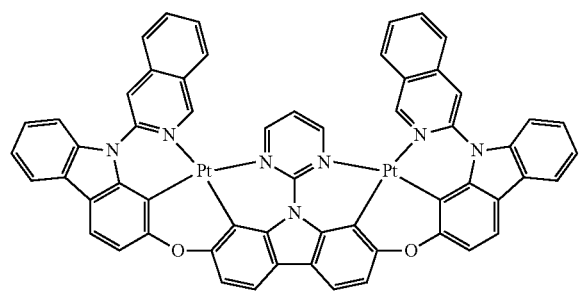
Compound 60
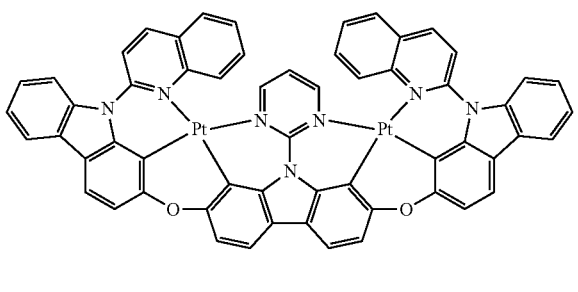
Compound 61
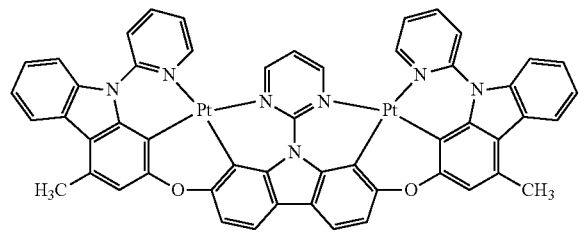
Compound 62
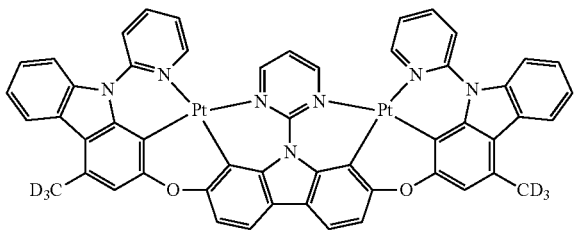

-continued
Compound 63
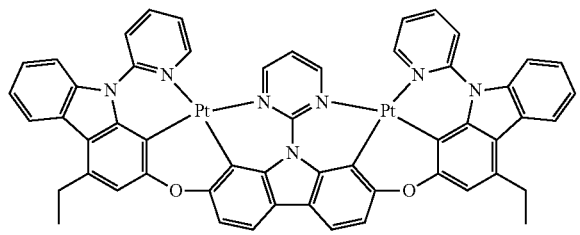
Compound 64
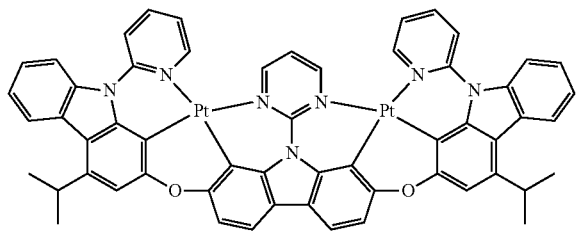
Compound 65
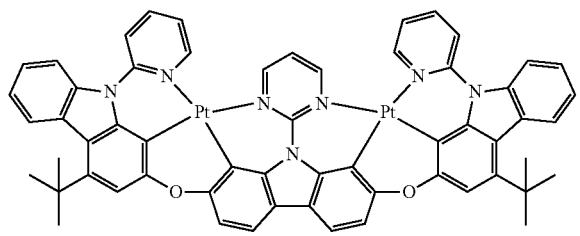
Compound 66
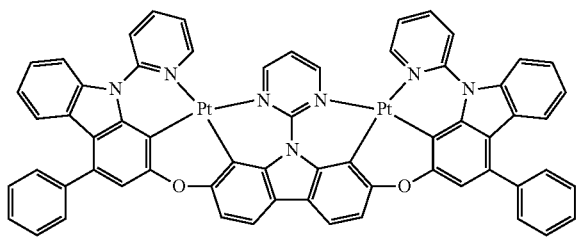
Compound 67
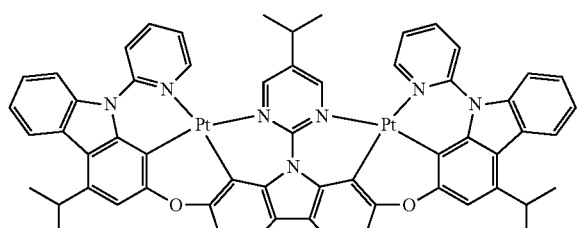
Compound 68
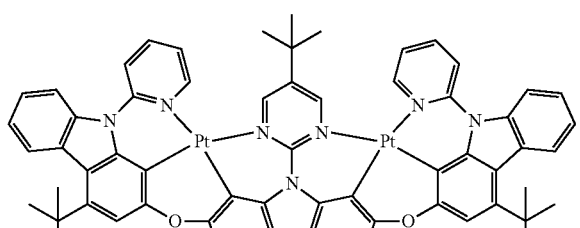
Compound 69
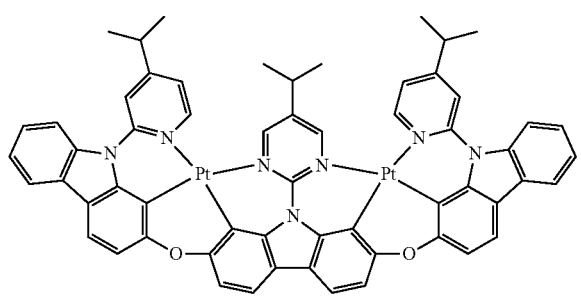
Compound 70
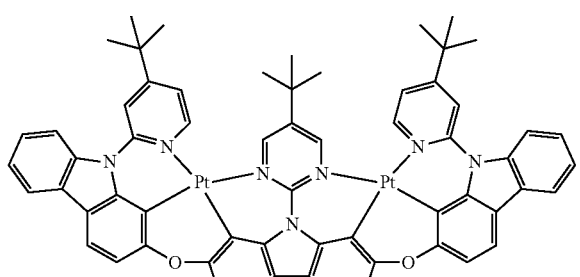
Compound 71
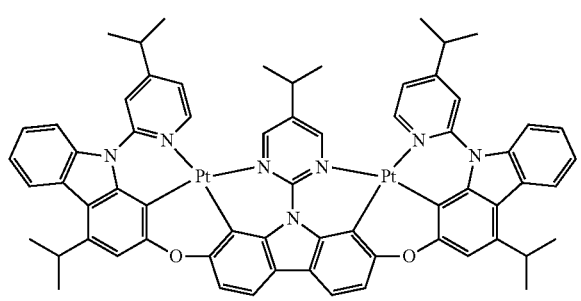
Compound 72
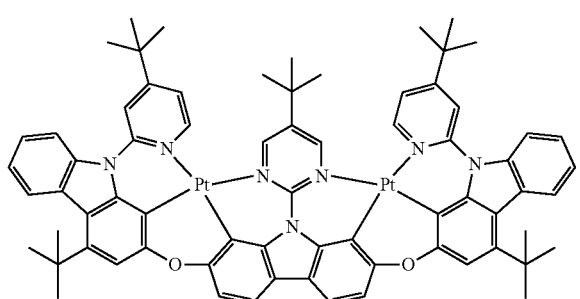

-continued
Compound 73
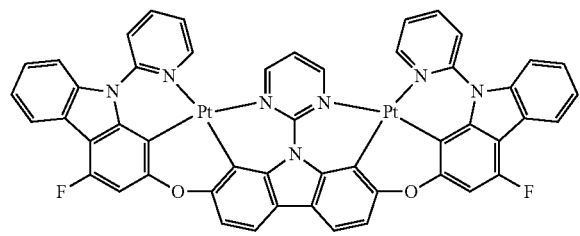
Compound 74
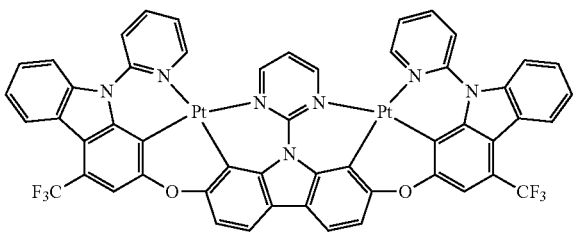
Compound 75
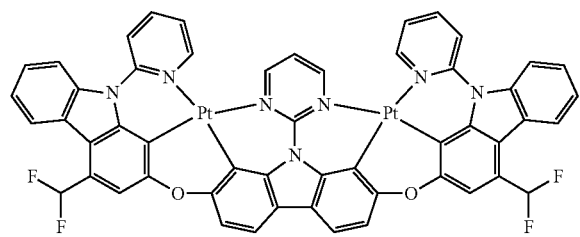
Compound 76
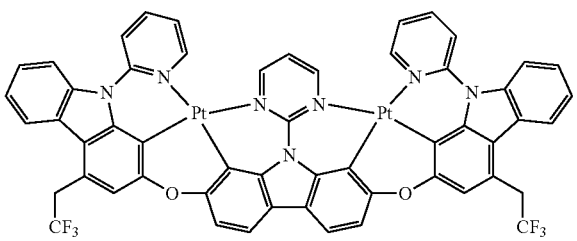
Compound 77
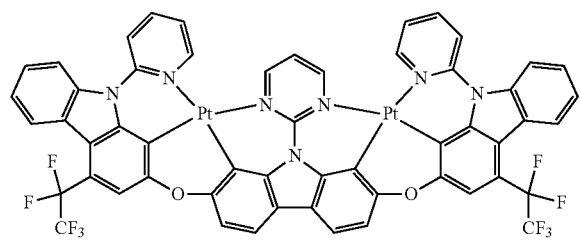
Compound 78
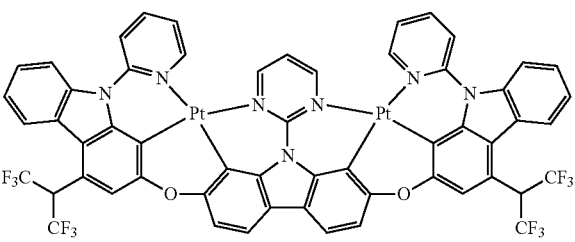
Compound 79
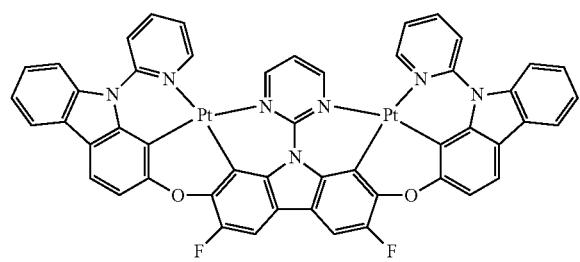
Compound 80
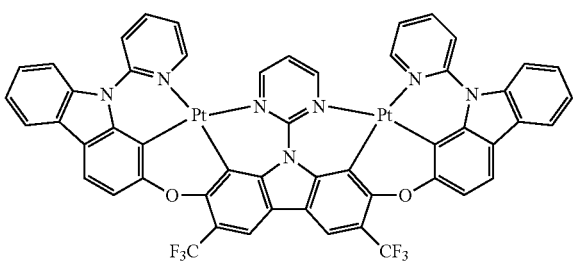
Compound 81
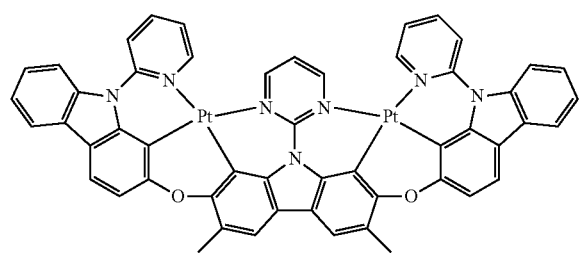
Compound 82
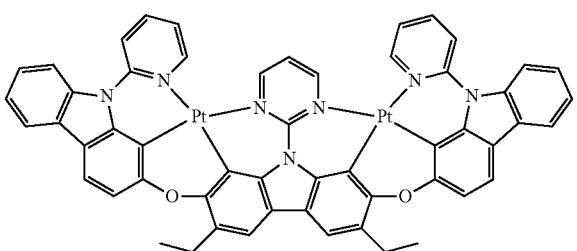

Compound 83
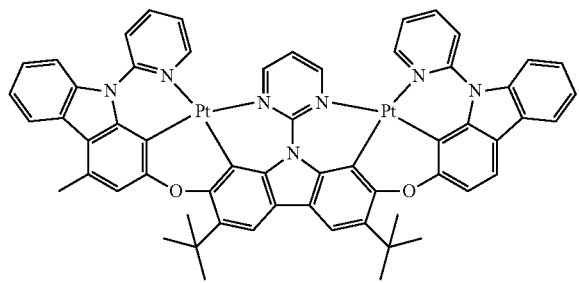
Compound 84
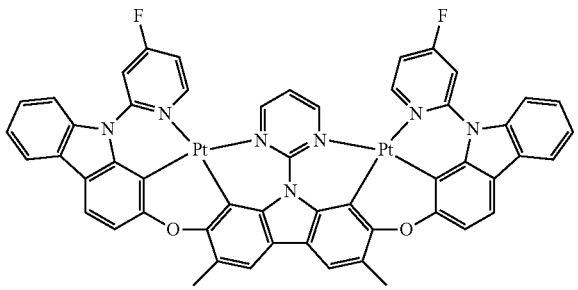
Compound 85
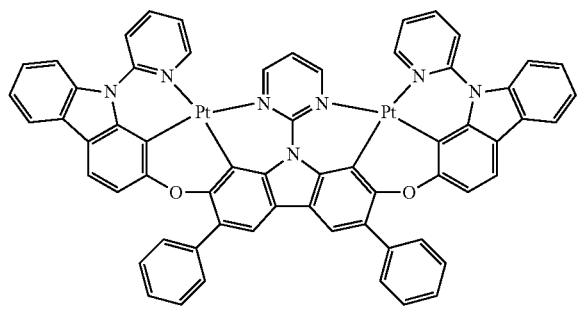
Compound 86
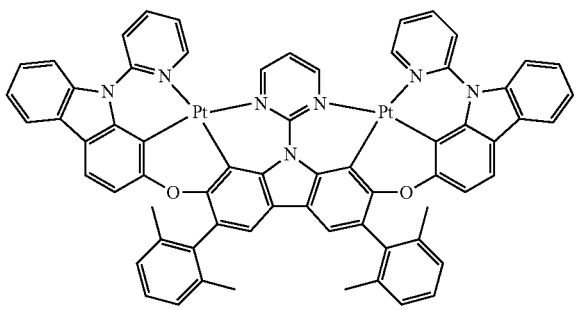
Compound 87
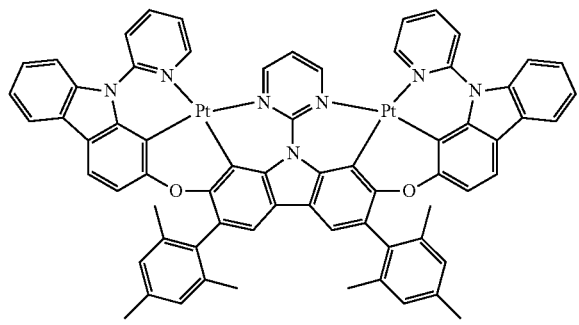
Compound 88
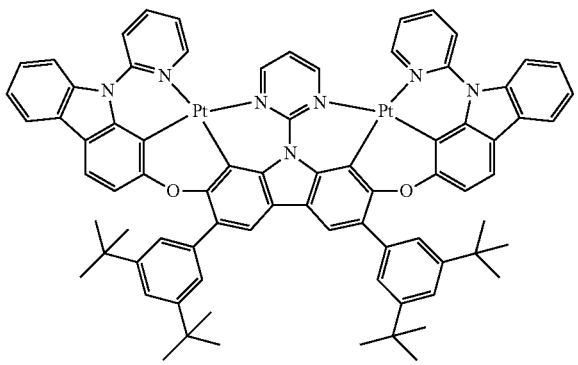
Compound 89
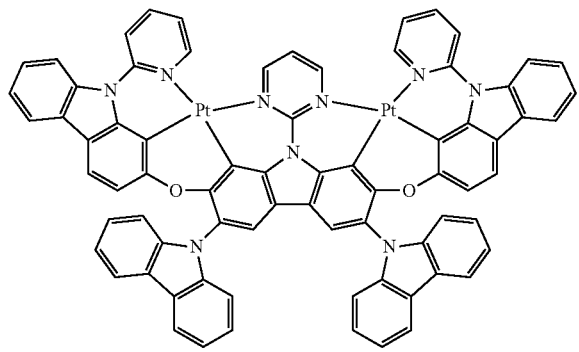
Compound 90
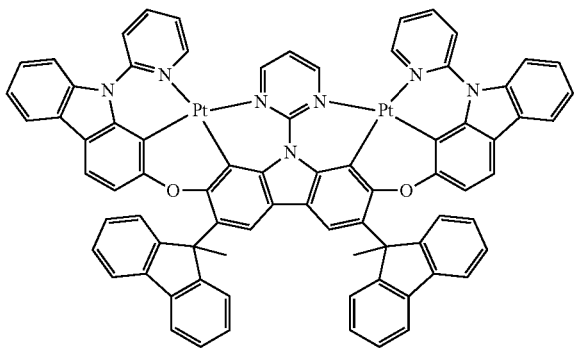

-continued
Compound 91
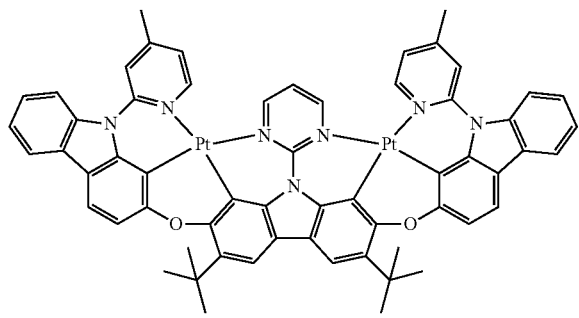
Compound 92
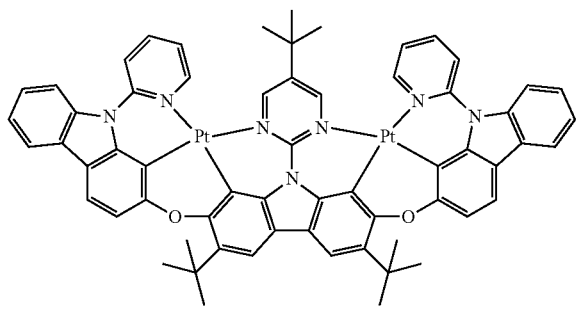
Compound 93
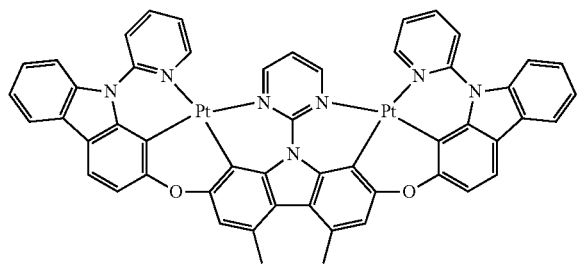
Compound 94
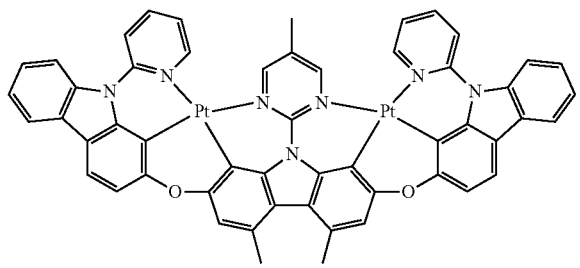
Compound 95
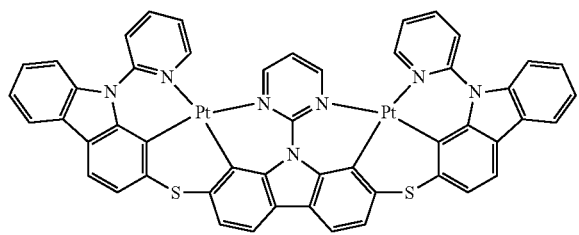
Compound 96
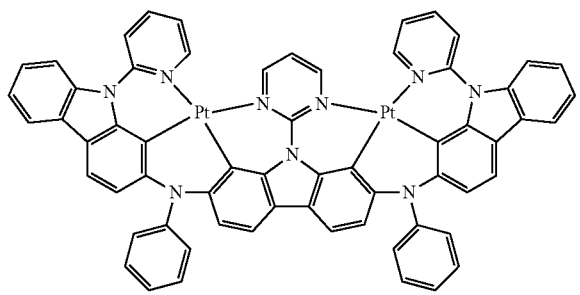
Compound 97
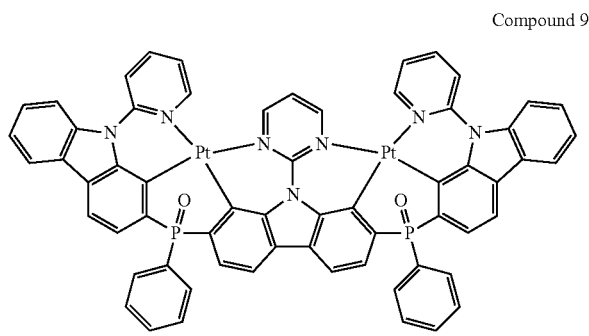
Compound 98
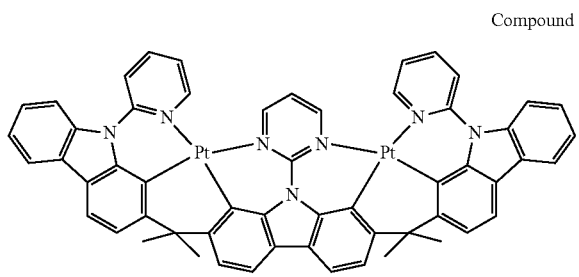
Compound 99
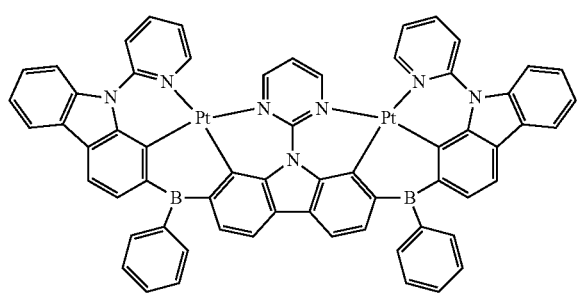
Compound 100
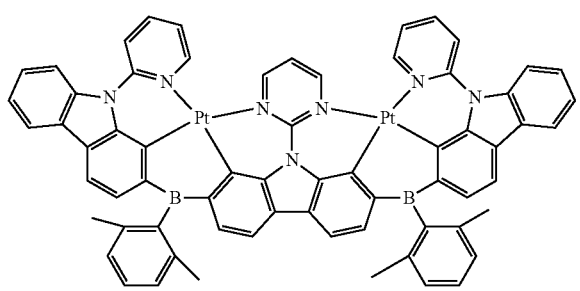

-continued
Compound 101
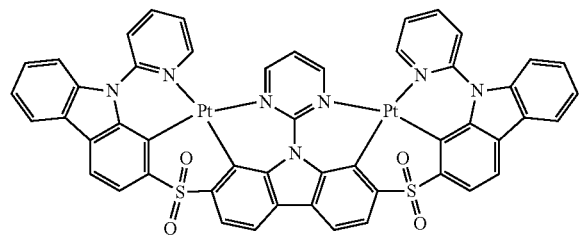
Compound 102
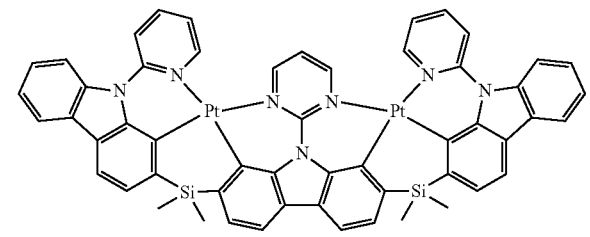
Compound 103
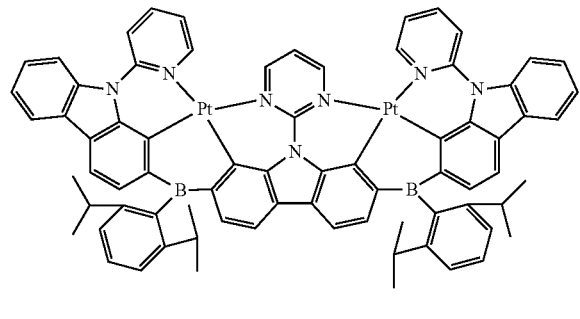
Compound 104
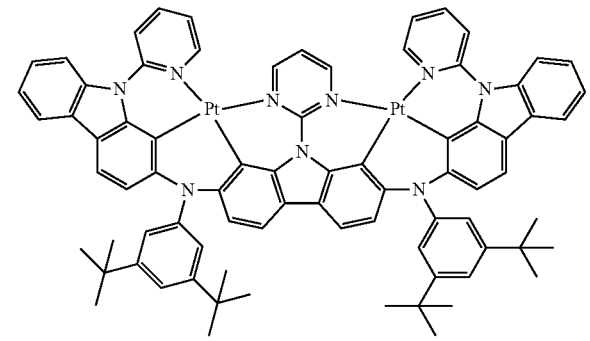
Compound 105
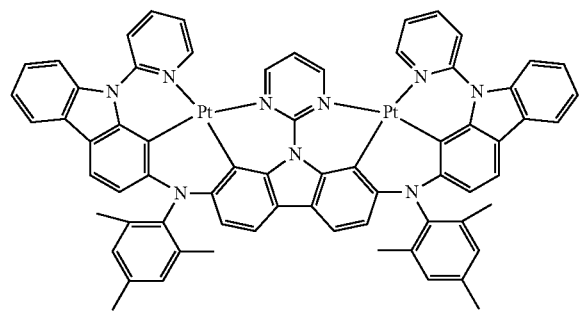
Compound 106
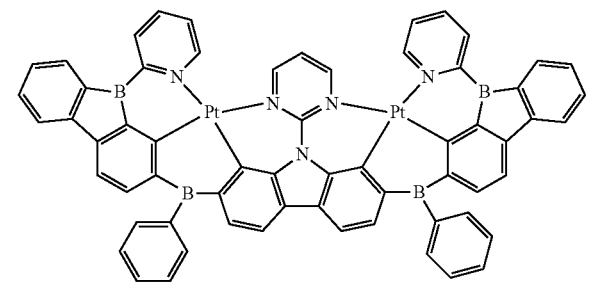
Compound 107
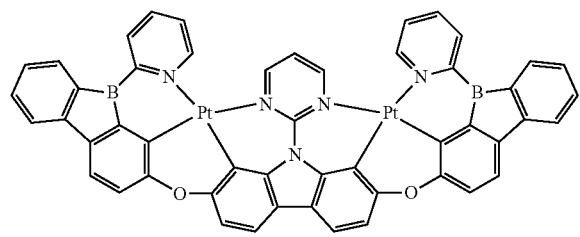
Compound 108
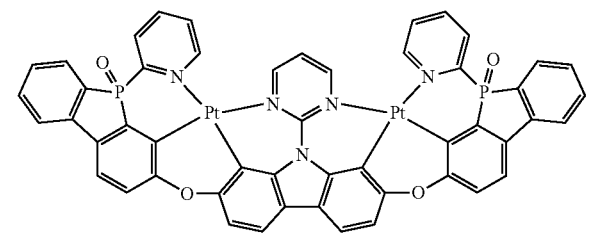
Compound 109
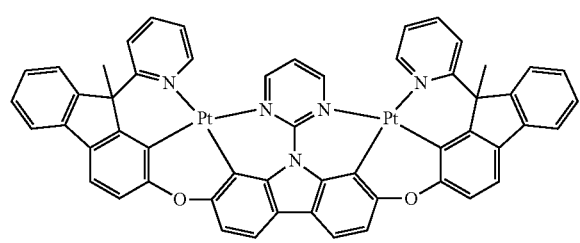
Compound 110
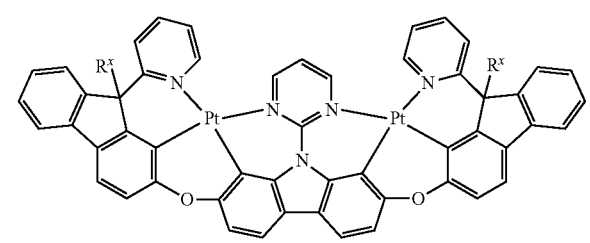

-continued
Compound 111
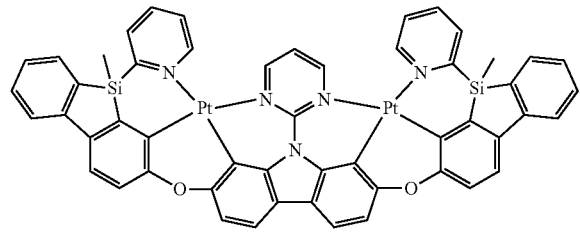
Compound 112
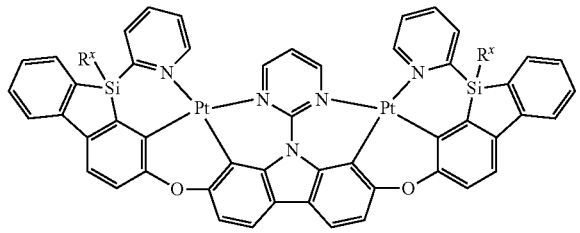
Compound 113
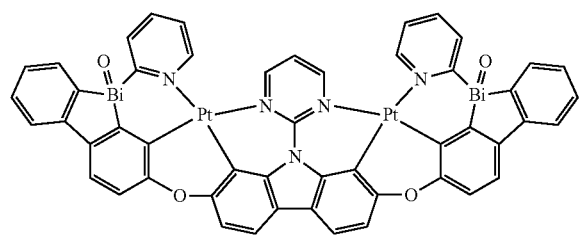
Compound 114
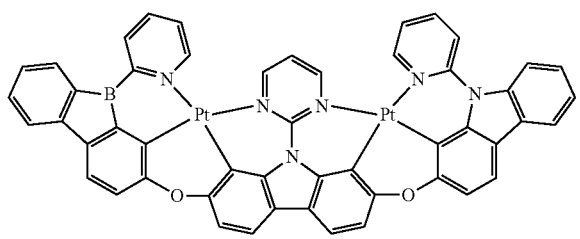
Compound 115
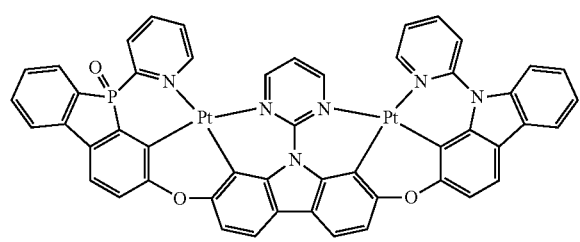
Compound 116
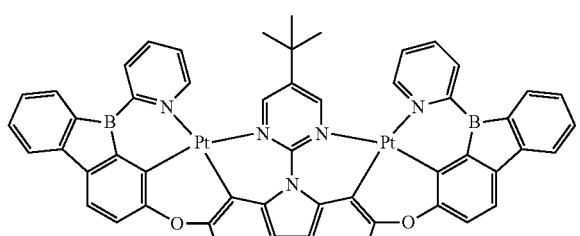
Compound 117
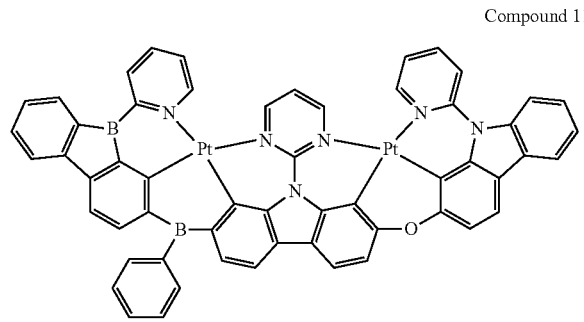
Compound 118
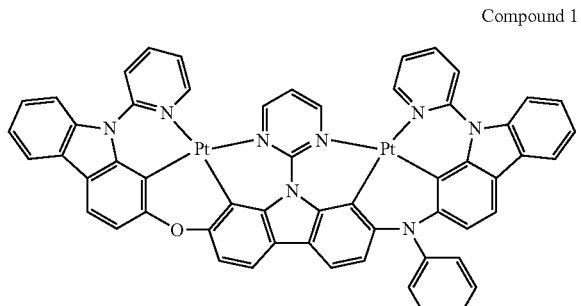
Compound 119
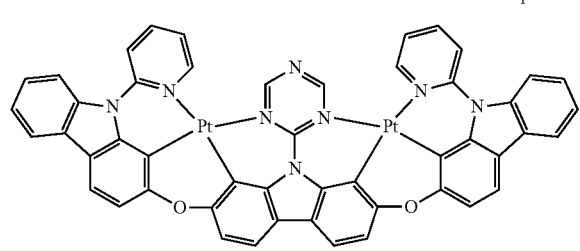
Compound 120
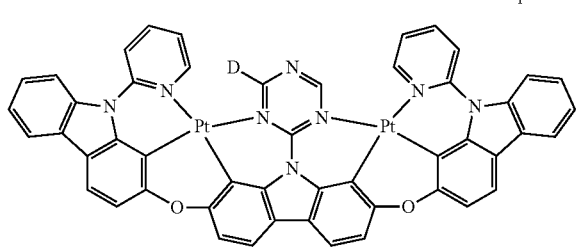
Compound 121
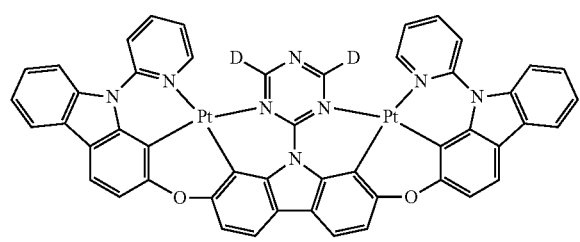
Compound 122
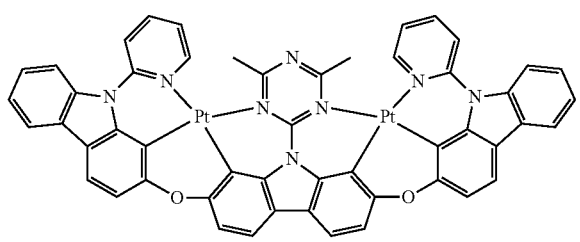

-continued
Compound 123
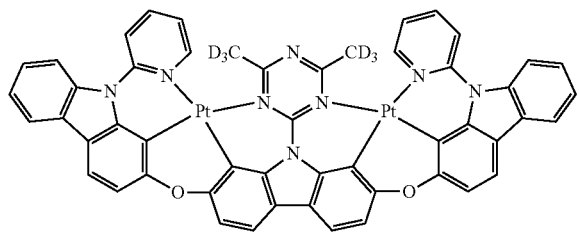
Compound 124
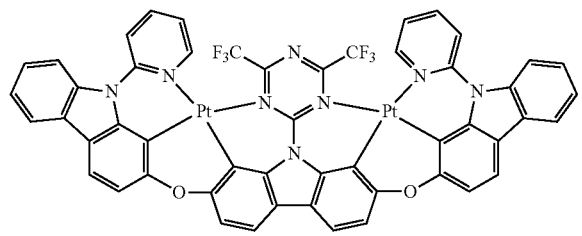
Compound 125
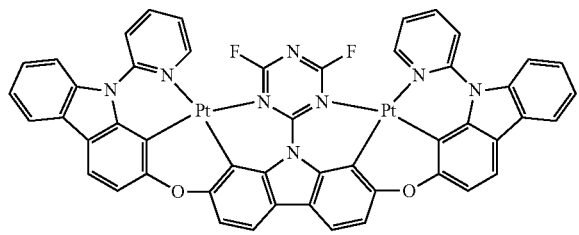
Compound 126
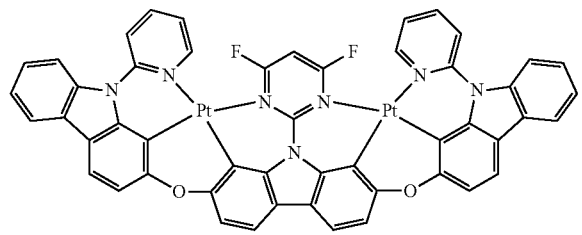
Compound 127
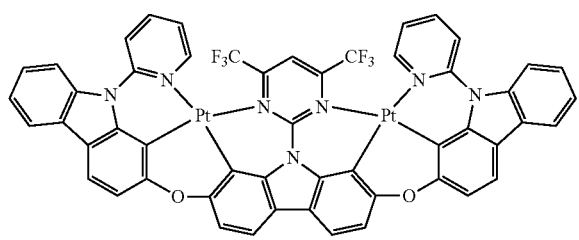
Compound 128
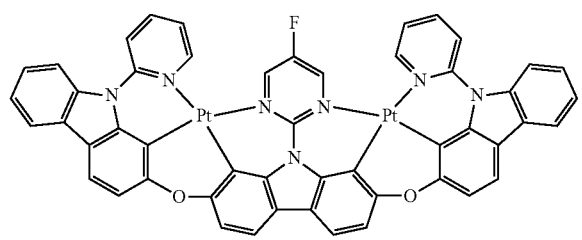
Compound 129
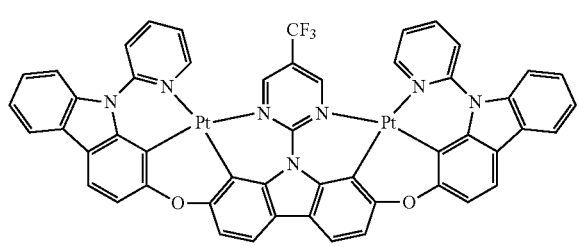
Compound 130
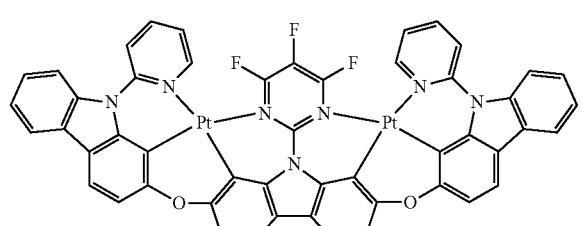
Compound 131
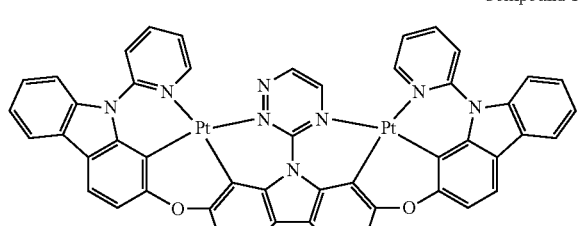
Compound 132
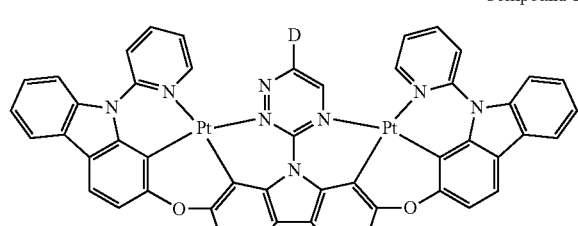
Compound 133
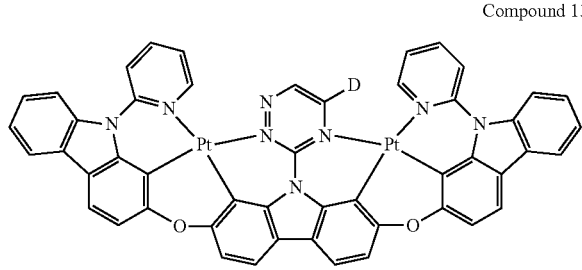
Compound 134
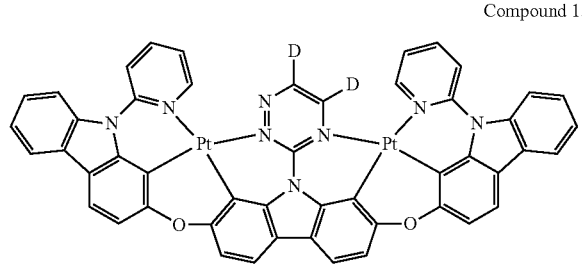

-continued
Compound 135
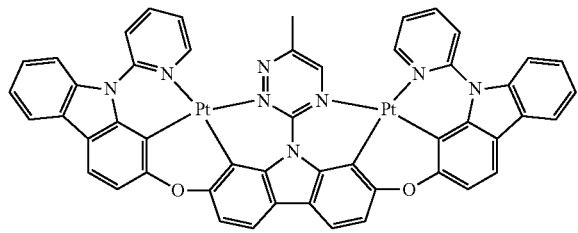
Compound 137
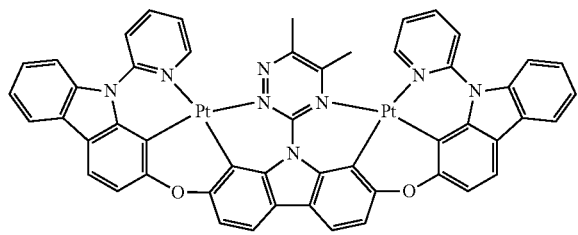
Compound 139
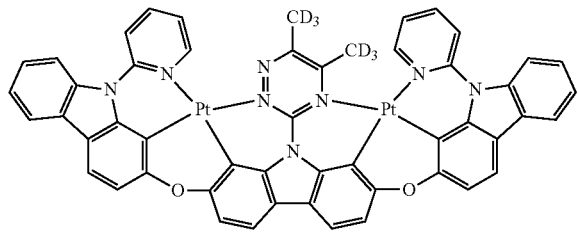
Compound 141
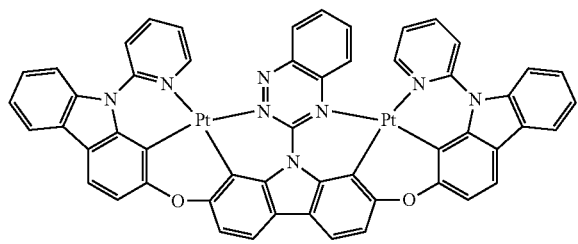
Compound 143
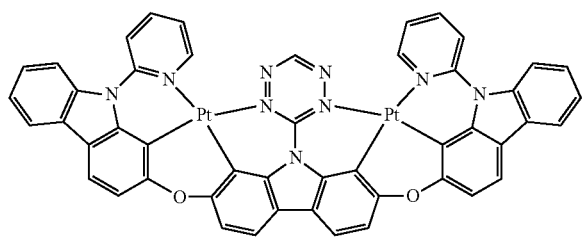
Compound 145
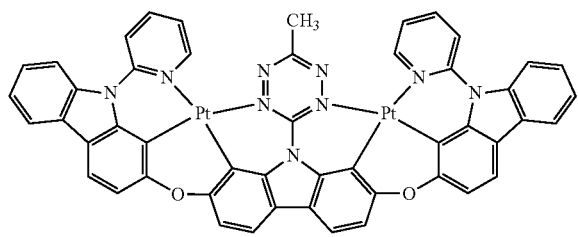
Compound 136
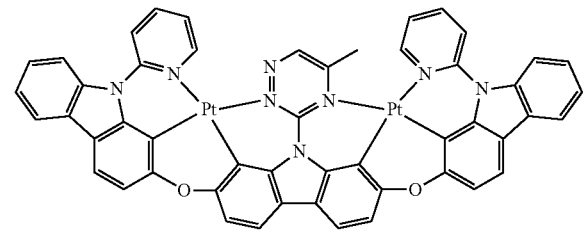
Compound 138
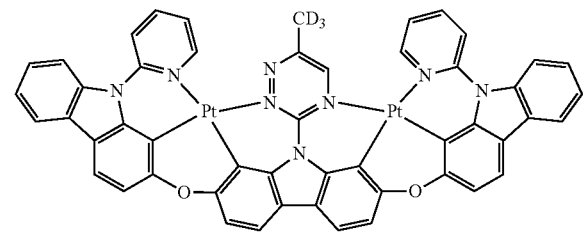
Compound 140
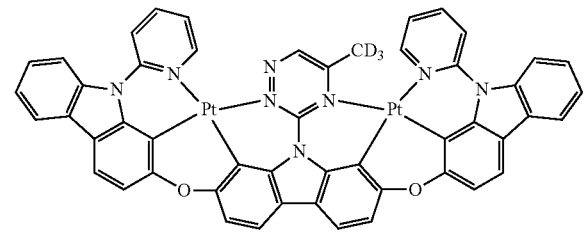
Compound 142
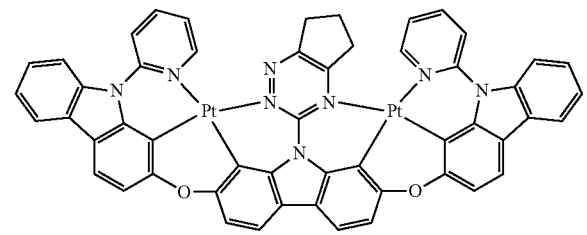
Compound 144
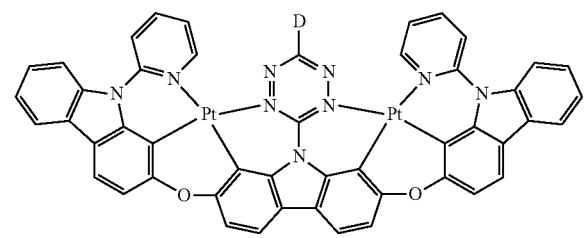
Compound 146
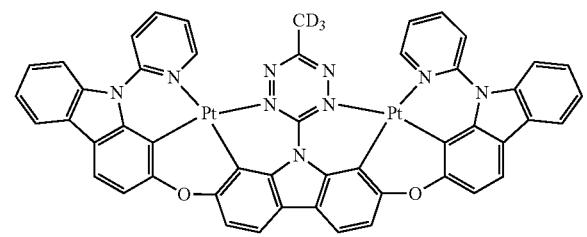

-continued
Compound 147
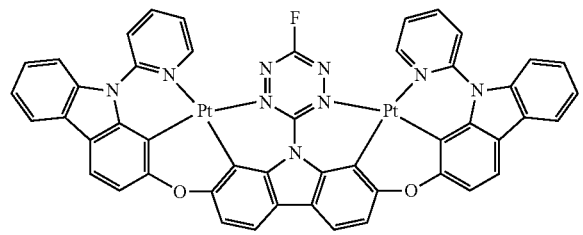
Compound 148
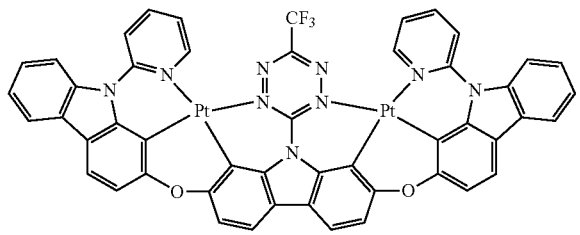
Compound 149
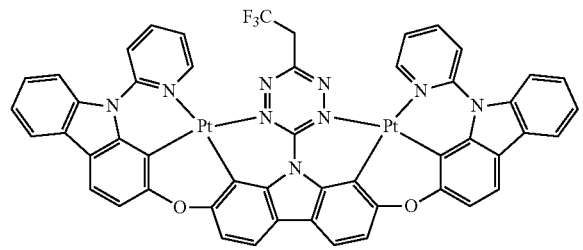
Compound 150
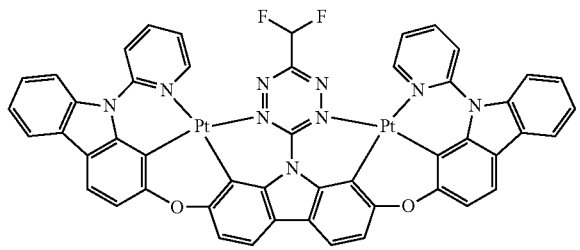
Compound 151
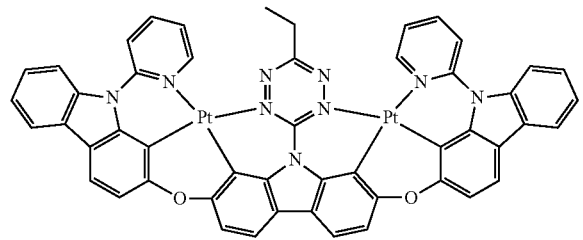
Compound 152
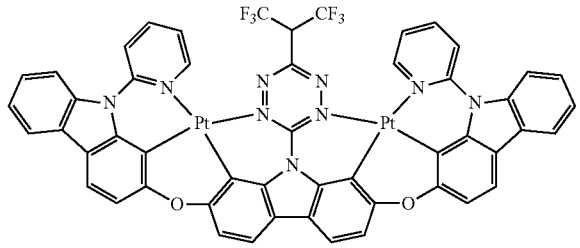
Compound 153
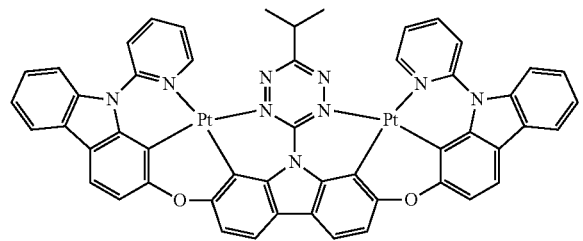
Compound 154
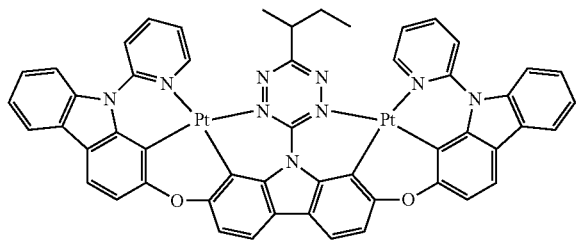
Compound 155
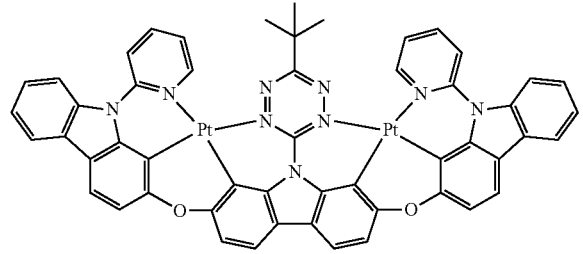
Compound 156
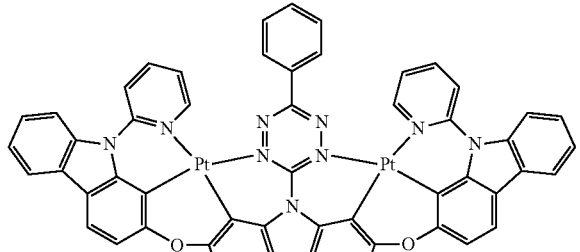

-continued
Compound 157
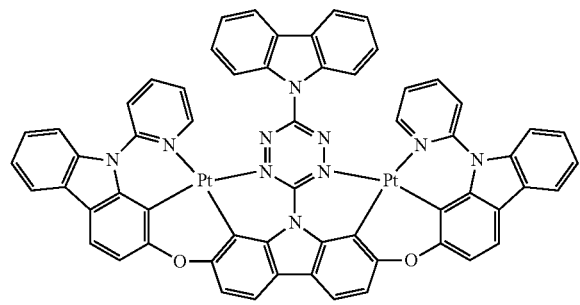
Compound 158
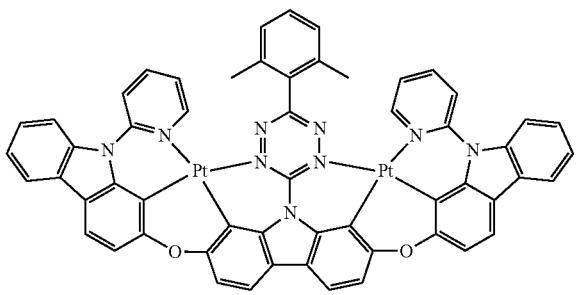
Compound 159
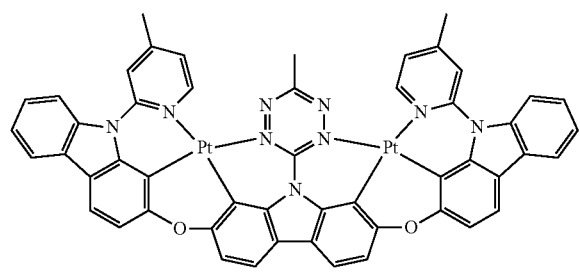
Compound 160
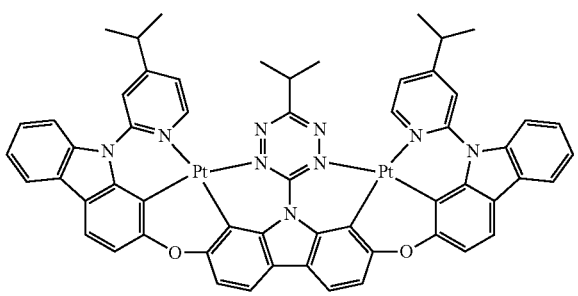
Compound 161
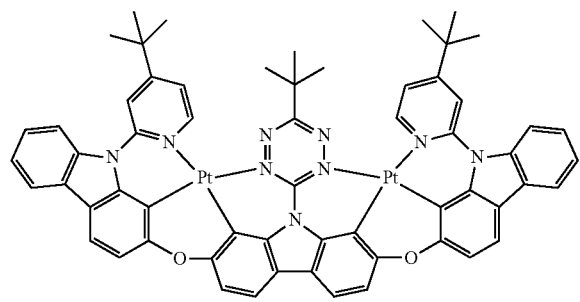
Compound 162
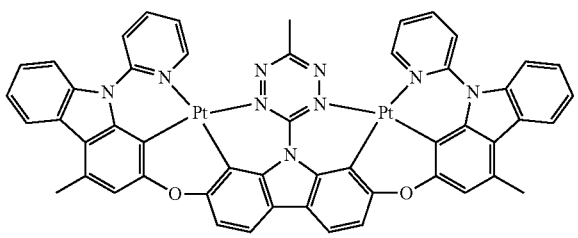
Compound 163
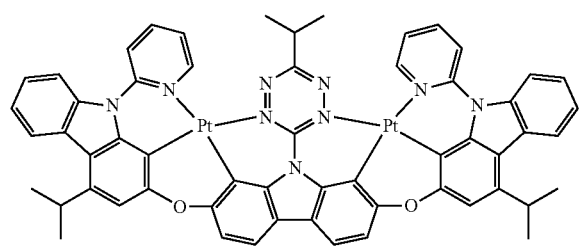
Compound 164
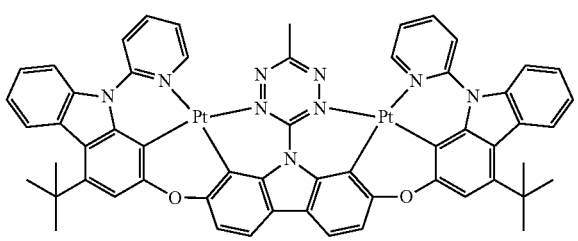
Compound 165
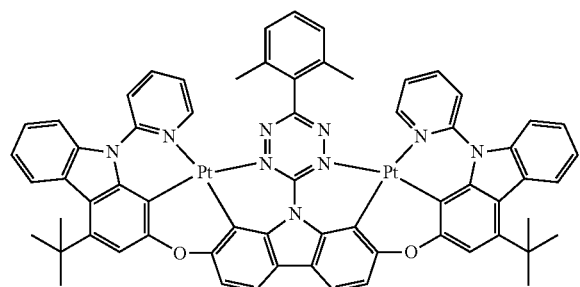
Compound 166
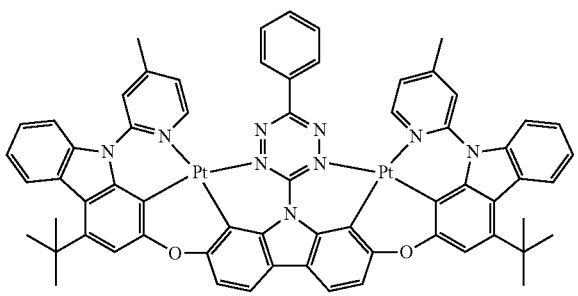

-continued
Compound 167
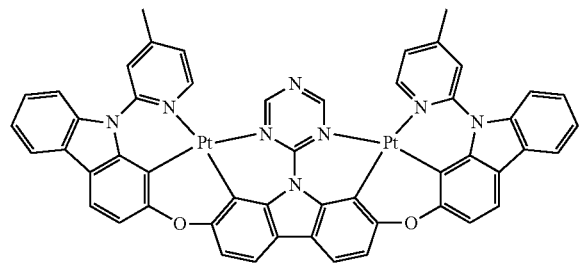
Compound 168
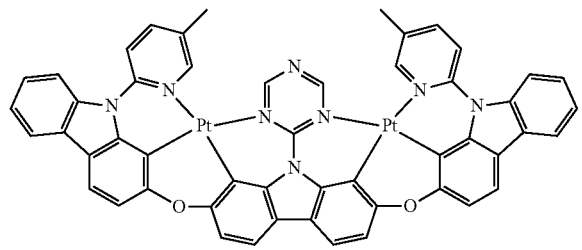
Compound 169
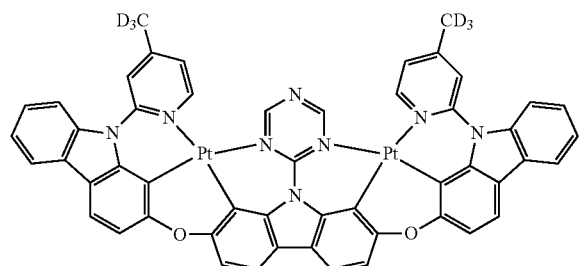
Compound 170
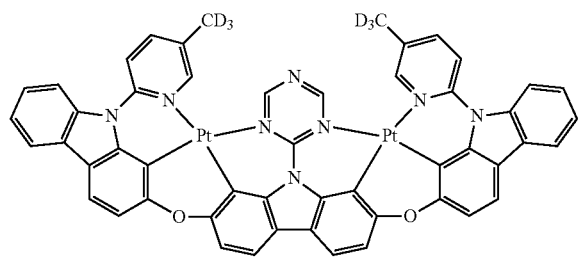
Compound 171
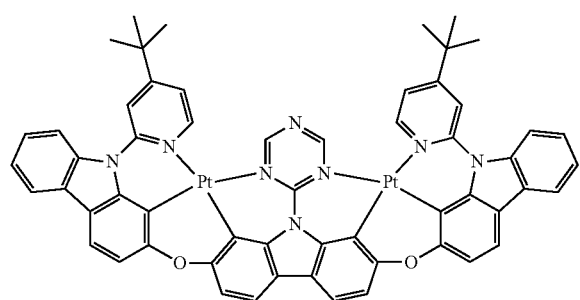
Compound 172
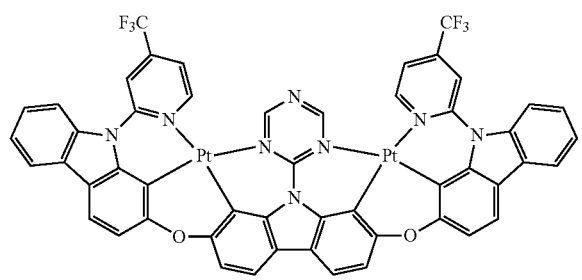
Compound 173
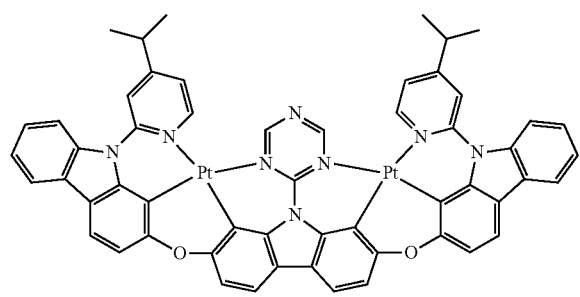
Compound 174
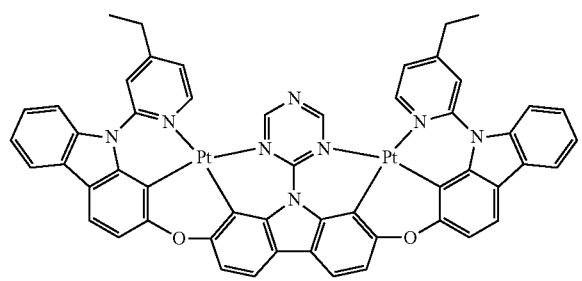
Compound 175
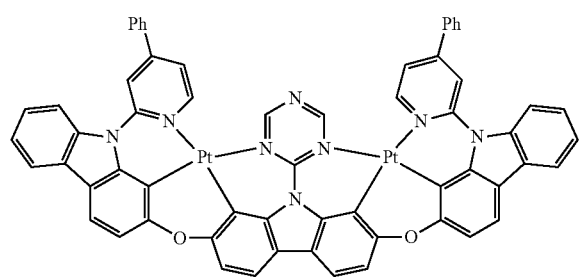
Compound 176
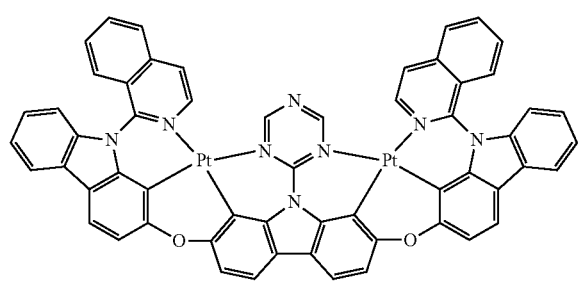

-continued
Compound 177
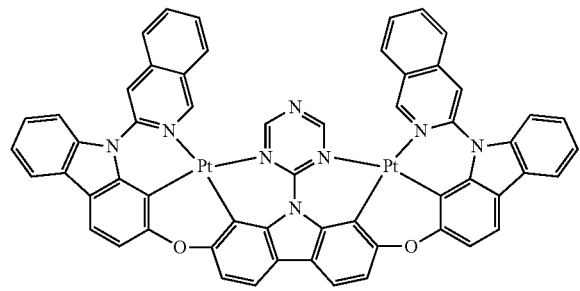
Compound 179
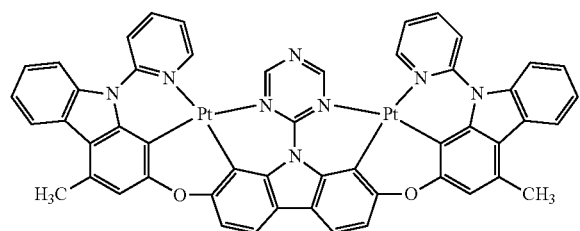
Compound 181
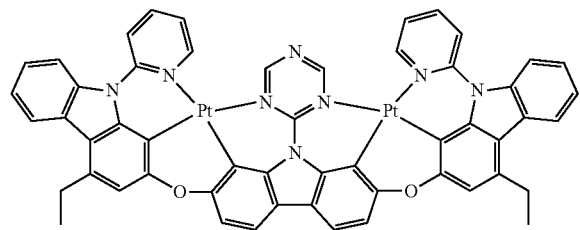
Compound 183
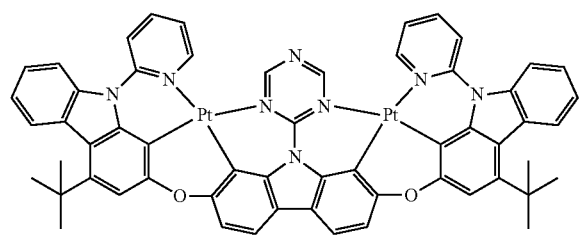
Compound 185
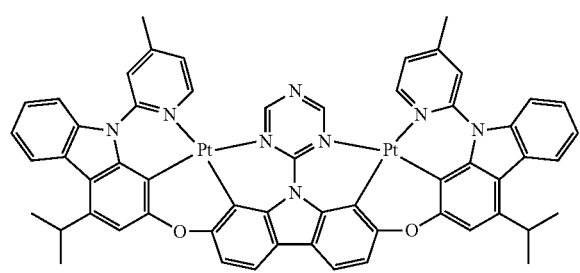
Compound 178
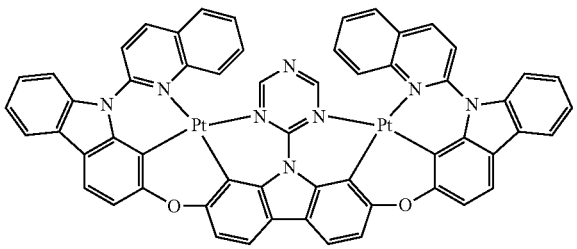
Compound 180
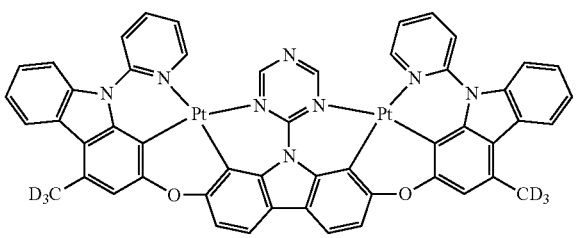
Compound 182
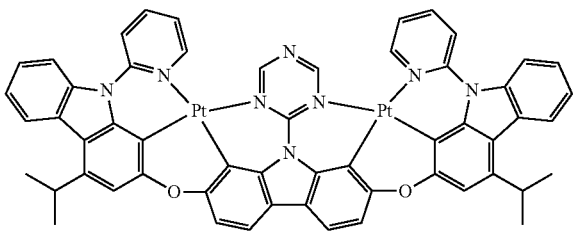
Compound 184
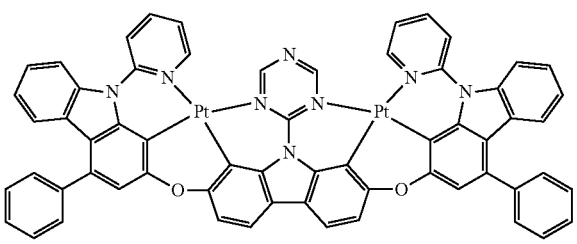
Compound 186
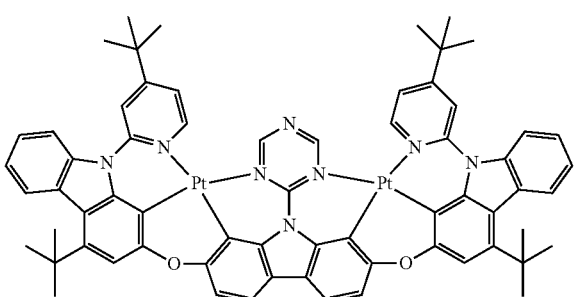

-continued
Compound 187
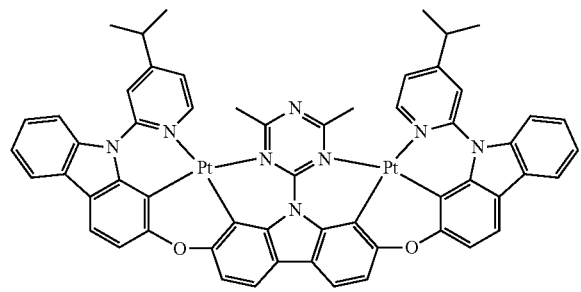
Compound 188
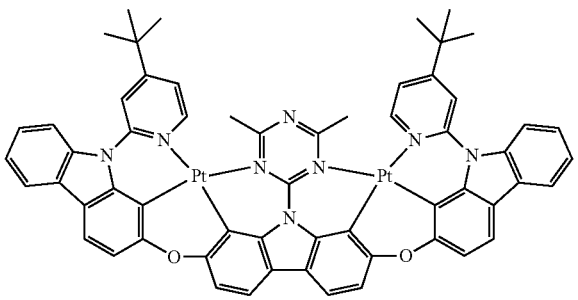
Compound 189
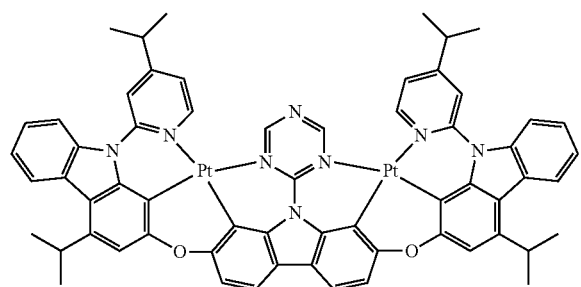
Compound 190
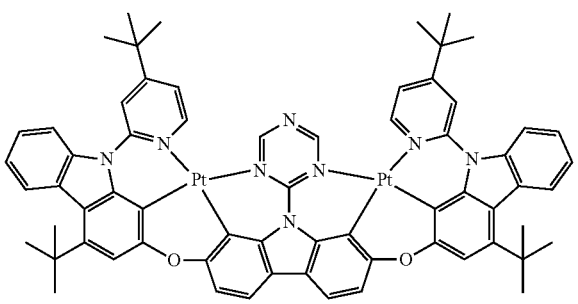
Compound 191
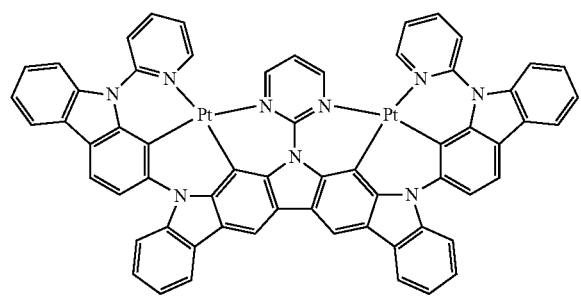
Compound 192
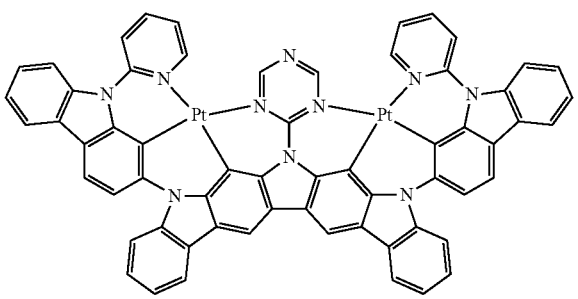
Compound 193
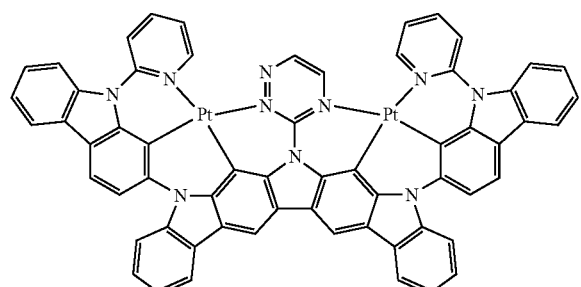
Compound 194
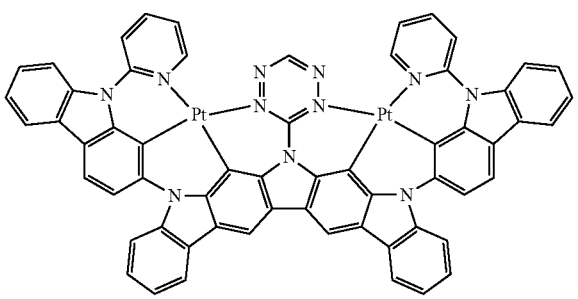
Compound 195
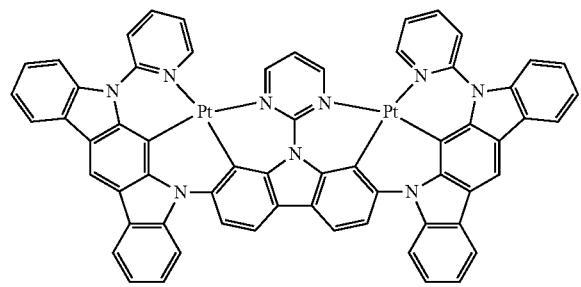
Compound 196
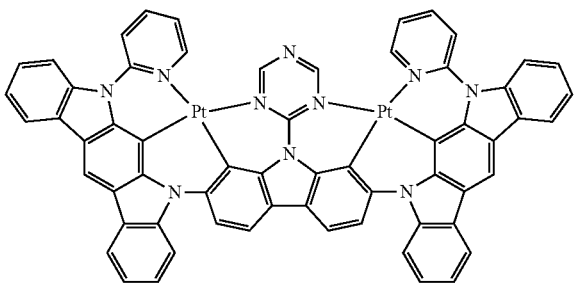

-continued
Compound 197
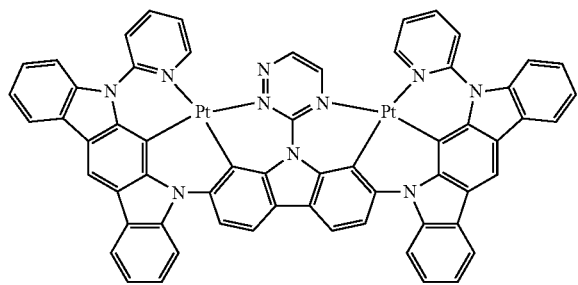
Compound 198
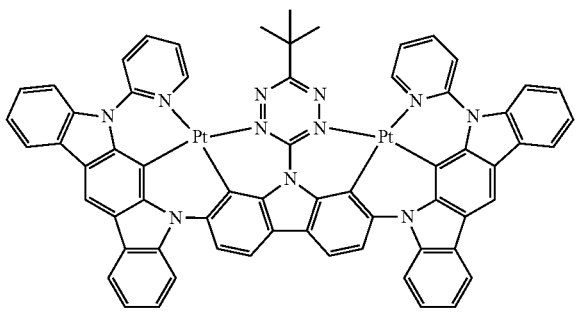
Compound 199
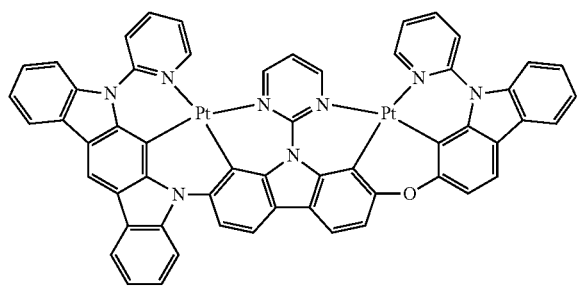
Compound 200
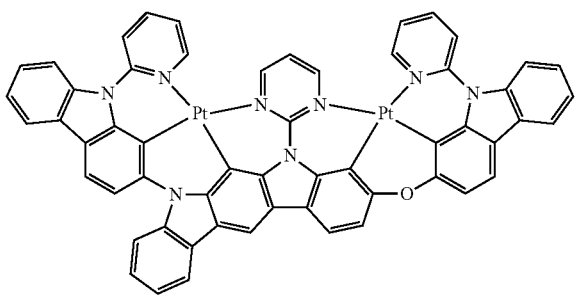
Compound 201
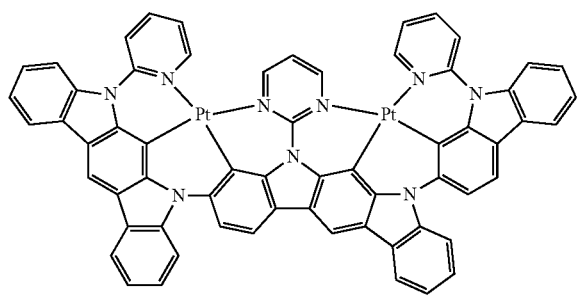
Compound 202
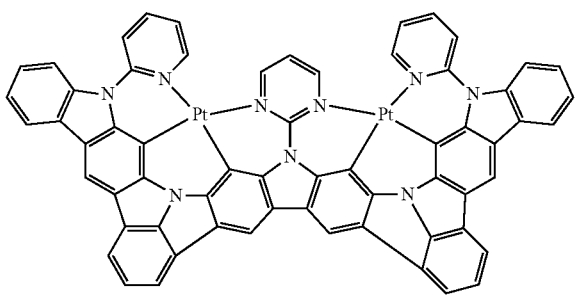
Compound 203
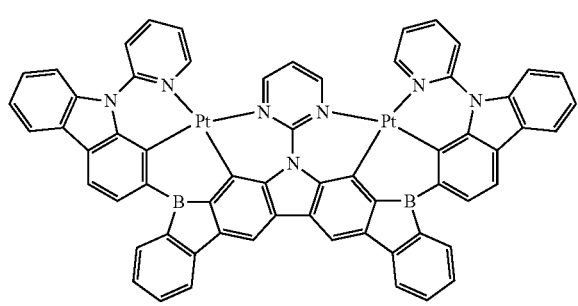
Compound 204
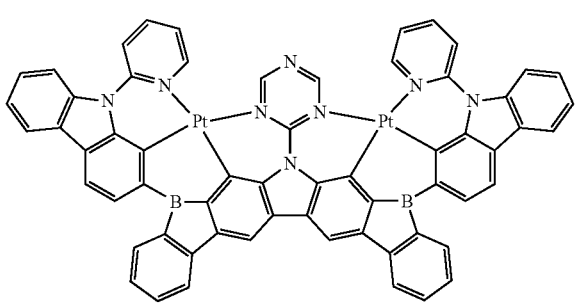
Compound 205
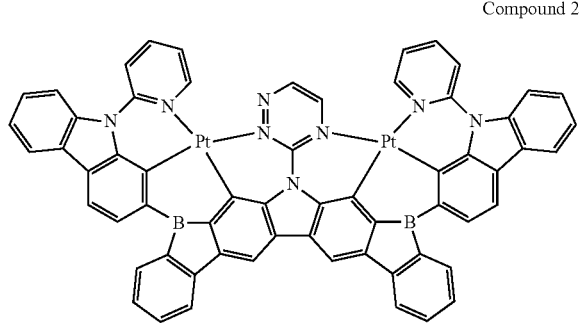
Compound 206
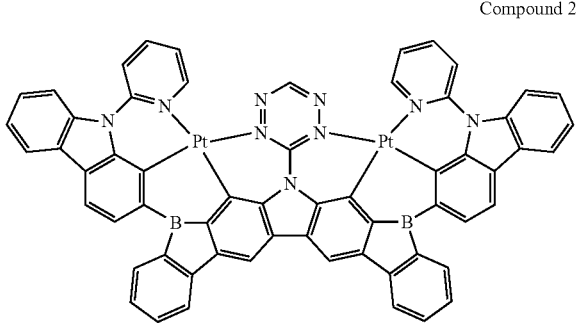

-continued
Compound 207
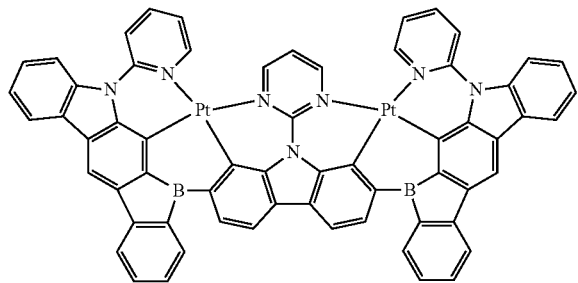
Compound 208
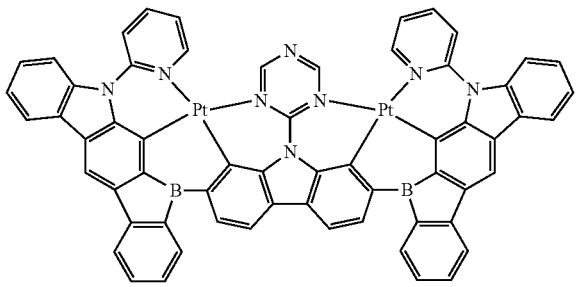
Compound 209
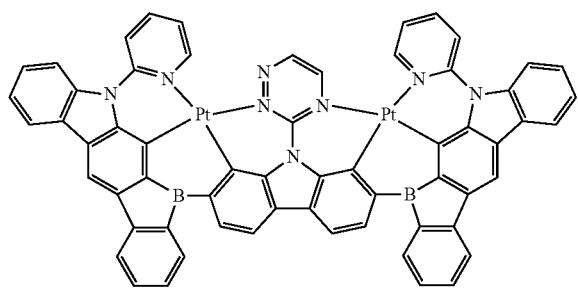
Compound 210
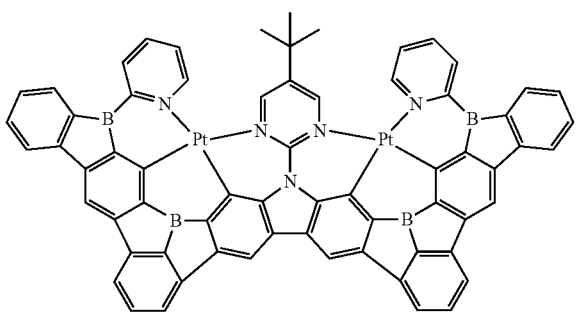
Compound 211
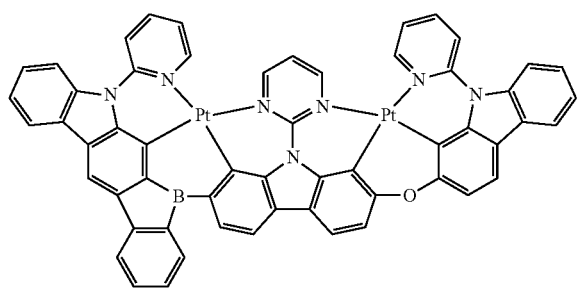
Compound 212
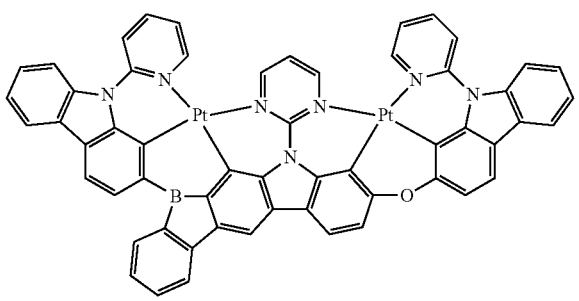
Compound 213
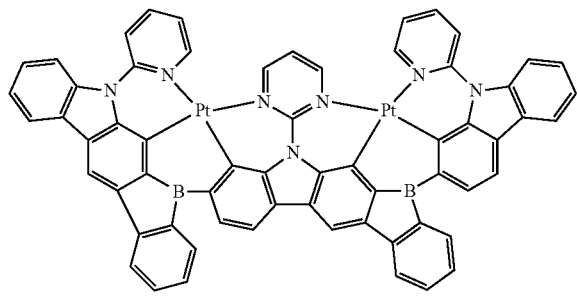
Compound 214
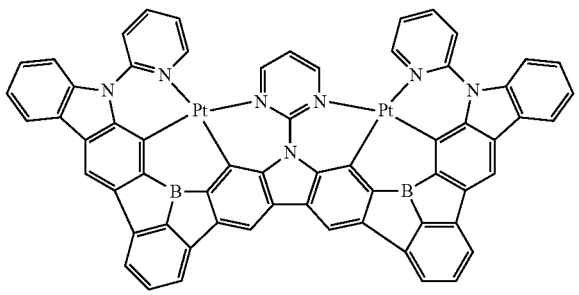
Compound 215
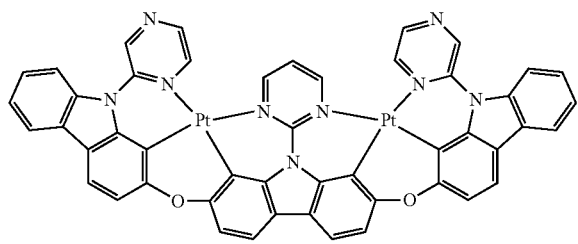
Compound 216
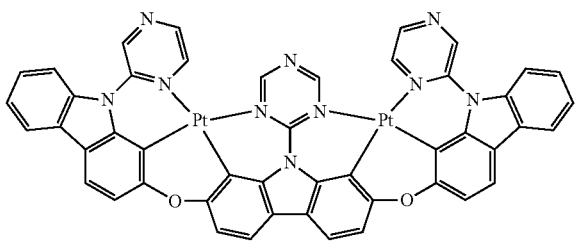

-continued
Compound 217
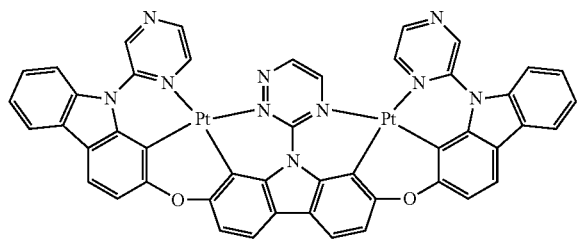
Compound 218
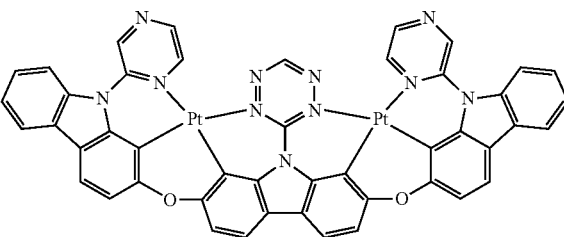
Compound 219
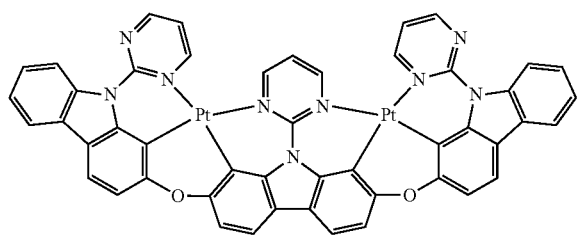
Compound 220
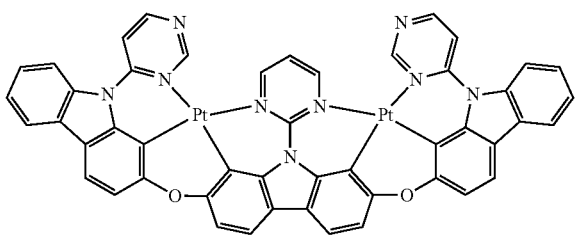
Compound 221
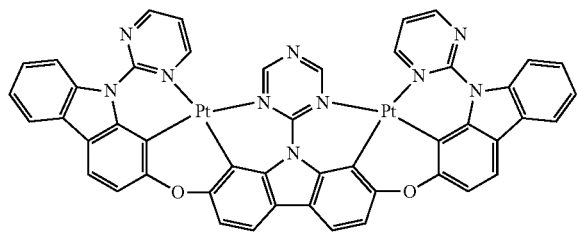
Compound 222
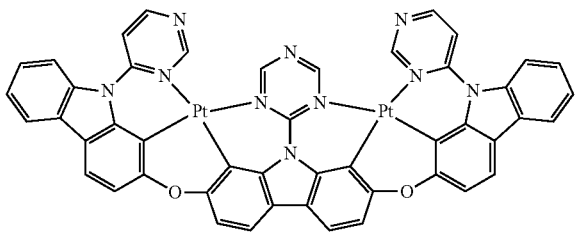
Compound 223
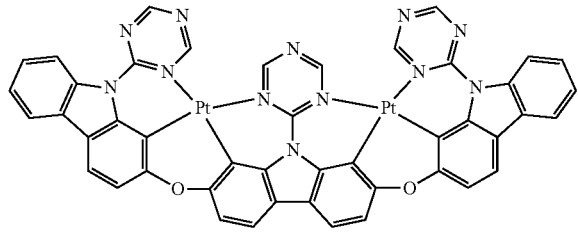
Compound 224
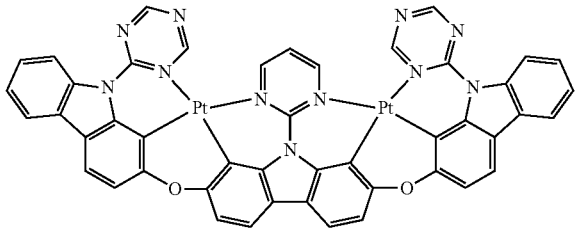
Compound 225
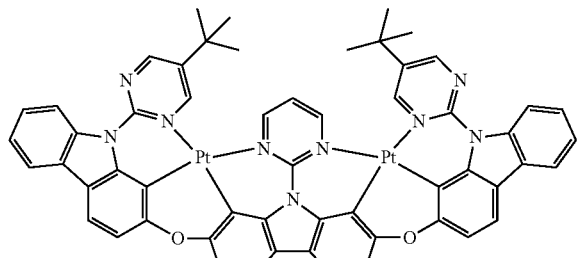
Compound 226
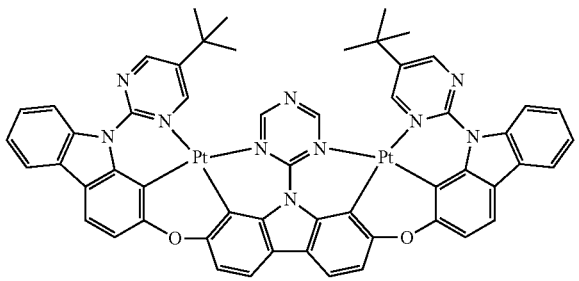

Compound 227
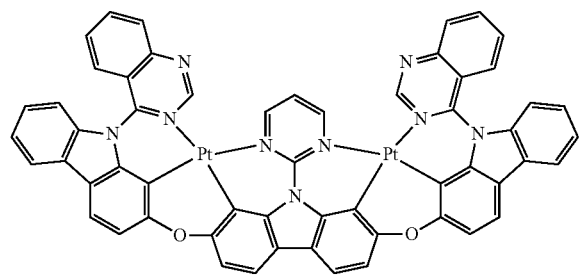
Compound 228
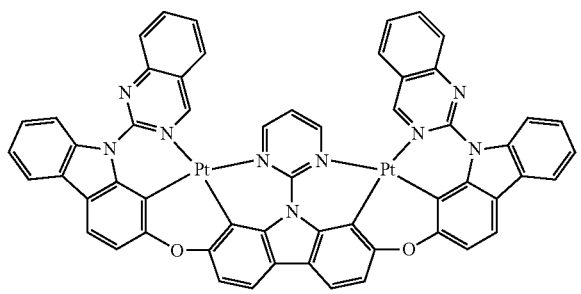
Compound 229
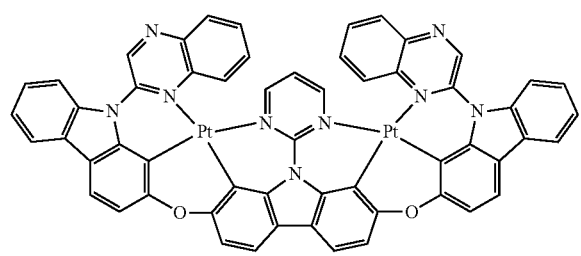
Compound 230
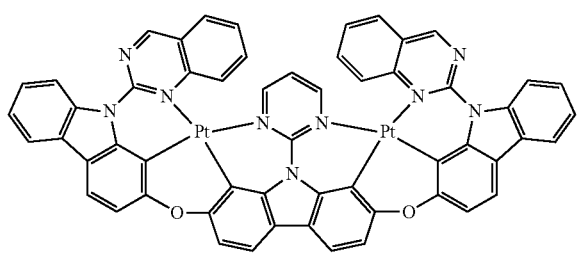
Compound 231
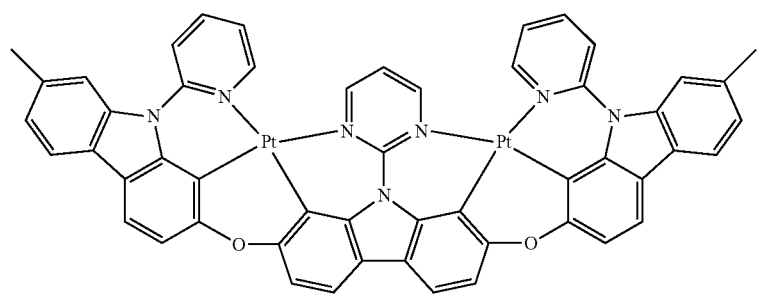
Compound 232
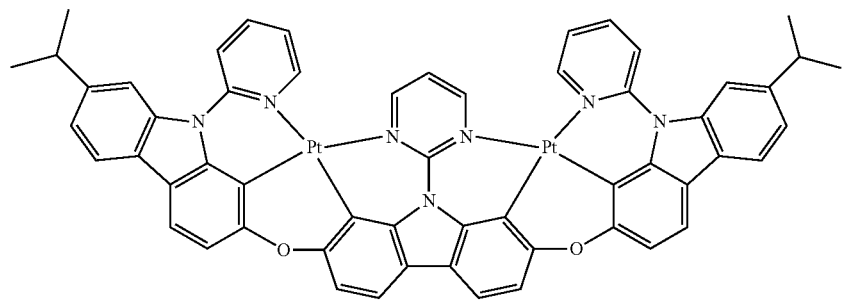
Compound 233
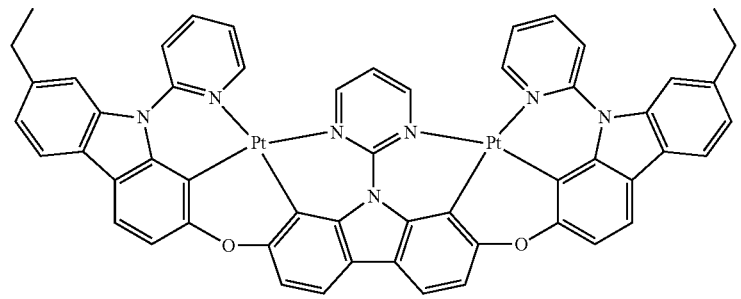

-continued
Compound 234
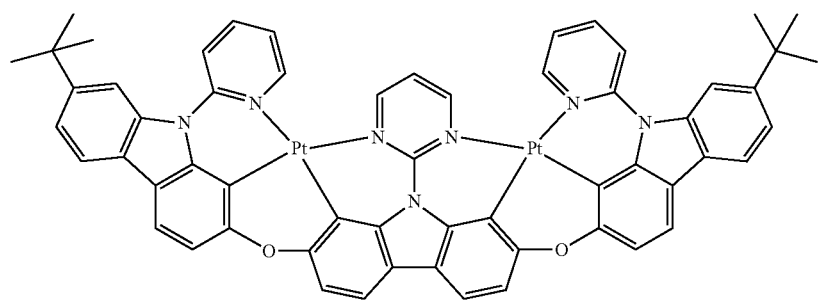
Compound 235
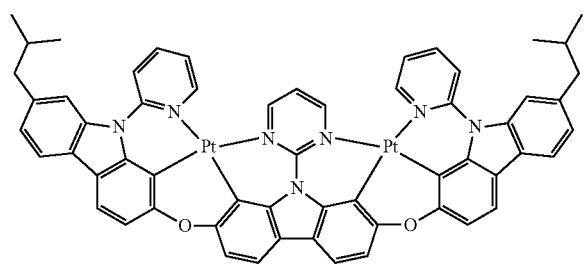
Compound 236
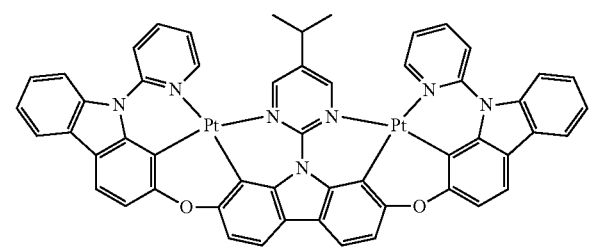
Compound 237
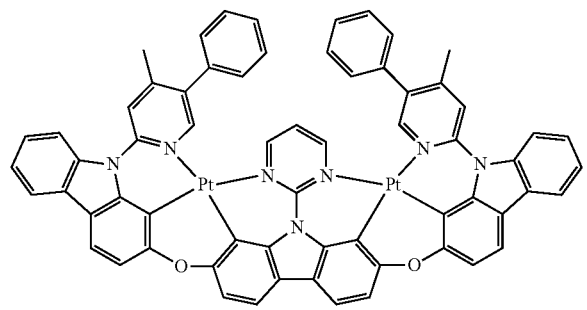
Compound 238
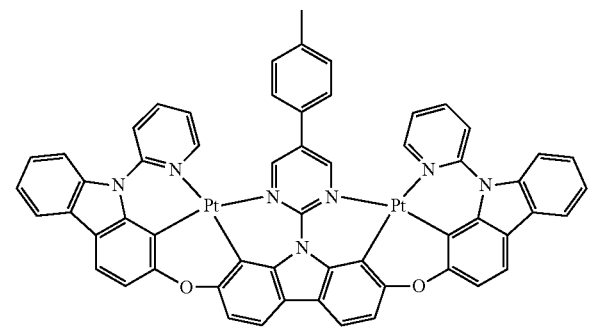
Compound 239
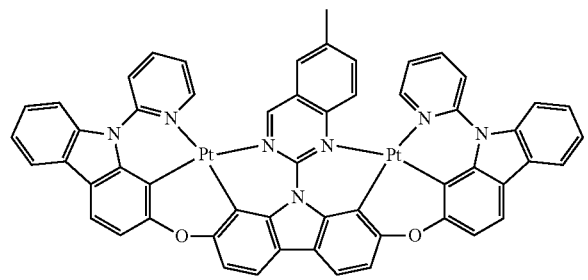
Compound 240
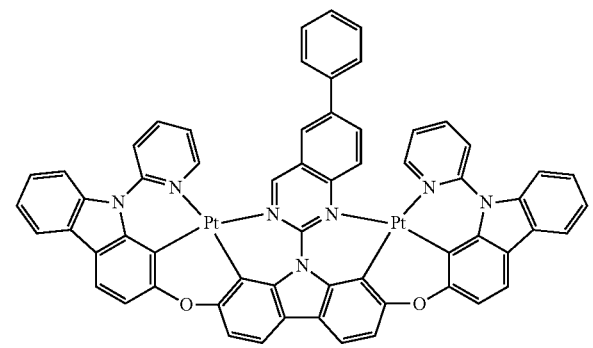

-continued

Compound 241

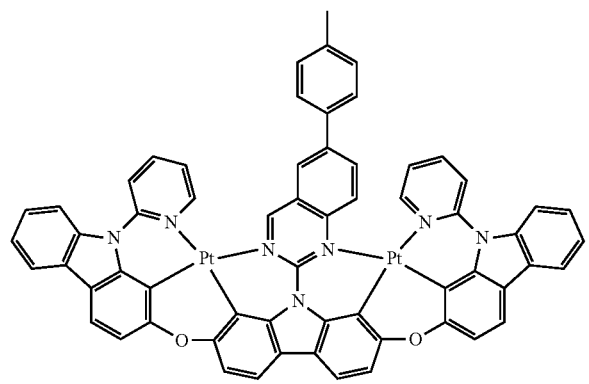

Compound 242

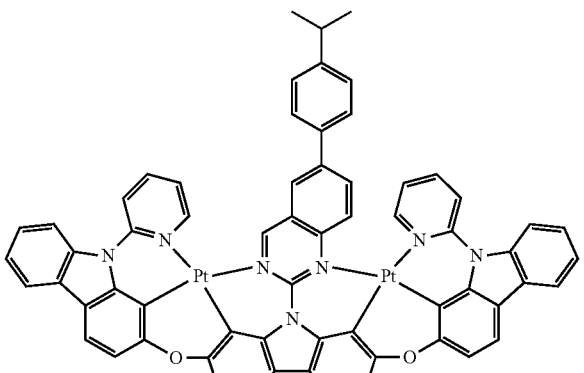

Compound 243

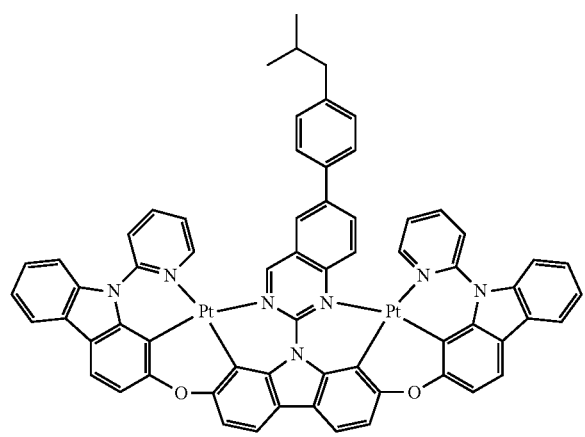

Compound 244

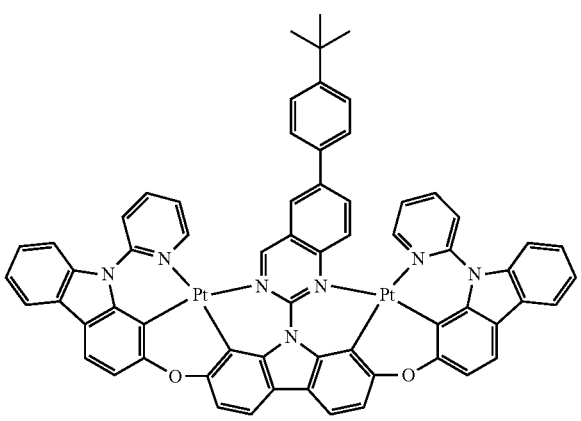

Compound 245

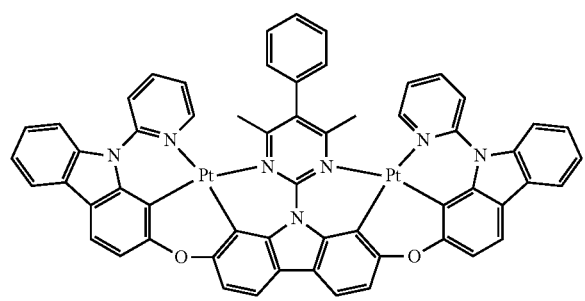

Compound 246

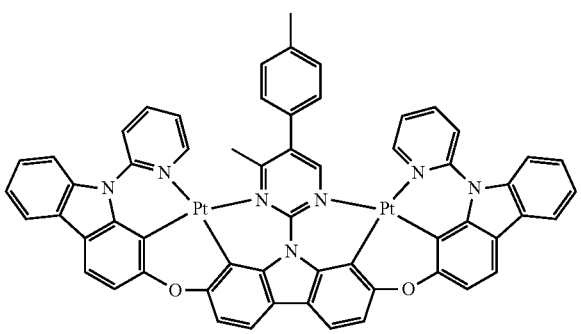

5. A device comprising the composition as described in claim 1.

6. The device as described in claim 5, wherein the device comprises a full color display.

7. The device as described in claim 5, wherein the device is a photovoltaic device.

8. The device as described in claim 5, wherein the device is a luminescent display device.

9. The device as described in claim 5, wherein the device comprises an organic light emitting diode (OLED).

10. The device as described in claim 9, wherein the device comprises a phosphorescent organic light emitting diode.

11. The device as described in claim 9, wherein the device is a phosphorescent organic light emitting diode.

12. A light emitting device comprising the composition as described in claim 1.

13. The device as described in claim 4, wherein the compound is selected to have 100% internal quantum efficiency in the device settings.

* * * * *